(12) United States Patent
Eberle et al.

(10) Patent No.: US 7,368,479 B2
(45) Date of Patent: May 6, 2008

(54) ALPHA-SULFONYLAMINO-ACETONITRILES

(75) Inventors: Martin Eberle, Bottmingen (CH); Daniel Stierli, Basel (CH); Urs Müller, Basel (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 393 days.

(21) Appl. No.: 10/517,977

(22) PCT Filed: Jun. 18, 2003

(86) PCT No.: PCT/EP03/06482

§ 371 (c)(1),
(2), (4) Date: Dec. 15, 2004

(87) PCT Pub. No.: WO04/000797

PCT Pub. Date: Dec. 31, 2003

(65) Prior Publication Data

US 2005/0234125 A1   Oct. 20, 2005

(30) Foreign Application Priority Data

Jun. 19, 2002 (GB) ................................. 0214116.6

(51) Int. Cl.
*A61K 31/275* (2006.01)
*C07C 255/00* (2006.01)

(52) U.S. Cl. ...................... 514/520; 558/410; 548/203; 548/260; 548/129; 546/329; 544/298; 514/269; 514/345; 514/362; 514/365

(58) Field of Classification Search ................ 558/410; 548/203, 260, 129; 546/329; 544/298; 514/520, 514/269, 345, 362, 365, 383, 396
See application file for complete search history.

(56) References Cited

U.S. PATENT DOCUMENTS 5,317,005 A * 5/1994 Jones .......................... 504/239

7,132,567 B2 * 11/2006 Alberte et al. .............. 564/153

FOREIGN PATENT DOCUMENTS

DE   2854932   7/1979
EP   0176327   4/1986

* cited by examiner

Primary Examiner—Rei-tsang Shiao
(74) Attorney, Agent, or Firm—Thomas Hamilton

(57) ABSTRACT

The invention relates to α-sulfonylamino-acetonitrile derivatives of the general formula (I) including the optical isomers thereof and mixtures of such isomers, wherein $Ar_1$, and $Ar_2$ independently of each other stand for an optionally substituted aryl or heteroaryl group, $R_1$, and $R_2$ stand independently of each other for hydrogen, optionally substituted $C_1$-$C_5$alkyl, optionally substituted $C_2$-$C_5$alkenyl, $C_2$-$C_5$alkynyl or optionally substituted $C_3$-$C_6$cycloalkyl; $R_3$ designates hydrogen, $C_3$-$C_5$alkenyl, $C_3$-$C_5$alkynyl or optionally substituted $C_1$-$C_5$alkyl; $R_4$ is optionally substituted $C_1$-$C_5$alkyl, optionally substituted $C_2$-$C_5$alkenyl, $C_2$-$C_5$alkynyl or optionally substituted $C_3$-$C_6$cycloalkyl; $R_5$ and $R_6$ are independently of each other hydrogen or optionally substituted $C_1$-$C_5$alkyl, optionally substituted $C_2$-$C_5$alkenyl, $C_2$-$C_5$alkynyl or optionally substituted $C_3$-$C_6$cycloalkyl; $R_7$, and $R_8$ are independently of each other hydrogen or optionally substituted $C_1$-$C_5$alkyl, optionally substituted $C_2$-$C_5$alkenyl, $C_2$-$C_5$alkynyl or optionally substituted $C_3$-$C_6$cycloalkyl; W designates a bridge selected from —O— —S(O)m— or —$NR_3$—; X designates a direct bond or a bridge selected from —O—, —S(O)m— or —$NR_3$—; a and b independently of each other stand for a number 1, 2 or 3; and c and m independently of each other stand for a number zero, 1 or 2. These compounds possess useful plant protecting properties and may advantageously be employed in agricultural practice for controlling or preventing the infestation of plants by phytopathogenic microorganisms, especially fungi.

11 Claims, No Drawings

ALPHA-SULFONYLAMINO-ACETONITRILES

This application is a 371 of PCT/EP03/06482 filed on Jun. 18, 2003.

The present invention relates to novel α-sulfonylamino-acetonitrile derivatives of formula I. It further encompasses the preparation of the novel active compounds and to agrochemical compositions comprising at least one of these novel compounds as active ingredient. The invention further relates to the preparation of the said compositions and to the use of the compounds or of the compositions for controlling or preventing the infestation of plants by phytopathogenic microorganisms, especially fungi.

The α-sulfonylamino-acetonitrile derivatives according to the present invention correspond to the general formula I

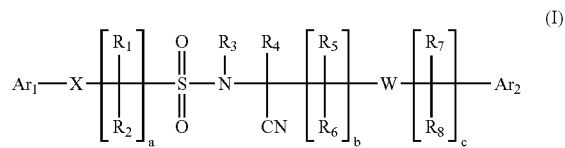

(I)

including the optical isomers thereof and mixtures of such isomers, wherein $Ar_1$ and $Ar_2$ independently of each other stand for an optionally substituted aryl or heteroaryl group, $R_1$ and $R_2$ stand independently of each other for hydrogen, optionally substituted $C_1$-$C_5$alkyl, optionally substituted $C_2$-$C_5$alkenyl, $C_2$-$C_5$alkynyl or optionally substituted $C_3$-$C_6$cycloalkyl;

$R_3$ designates hydrogen, $C_3$-$C_5$alkenyl, $C_3$-$C_5$alkynyl or optionally substituted $C_1$-$C_5$alkyl;

$R_4$ is optionally substituted $C_1$-$C_5$alkyl, optionally substituted $C_2$-$C_5$alkenyl, $C_2$-$C_5$alkynyl or optionally substituted $C_3$-$C_6$cycloalkyl;

$R_5$ and $R_6$ are independently of each other hydrogen or optionally substituted $C_1$-$C_5$alkyl, optionally substituted $C_2$-$C_5$alkenyl, $C_2$-$C_5$alkynyl or optionally substituted $C_3$-$C_6$cycloalkyl;

$R_7$ and $R_8$ are independently of each other hydrogen or optionally substituted $C_1$-$C_5$alkyl, optionally substituted $C_2$-$C_5$alkenyl, $C_2$-$C_5$alkynyl or optionally substituted $C_3$-$C_6$cycloalkyl;

W designates a bridge selected from —O—, —S(O)$_m$' or —NR$_3$—;

X designates a direct bond or a bridge selected from —O—, —S(O)$_m$— or —NR$_3$—;

a and b independently of each other stand for a number 1, 2 or 3; and c and m independently of each other stand for a number zero, 1 or 2.

More specifically the present invention refers to the α-sulfonylamino-acetonitrile derivatives of formula I wherein $Ar_1$ stands for an aryl group which is optionally substituted with n radicals independently selected from $R_9$; or stands for a 5-ring-membered heteroaryl group comprising as ring members 1 to 4 heteroatoms selected from nitrogen, oxygen or sulfur and being optionally substituted with n radicals independently selected from $R_{11}$; or stands for a 6-ring-membered heteroaryl group comprising as ring members 1 to 4 heteroatoms selected from nitrogen, oxygen or sulfur and being optionally substituted with n radicals independently selected from $R_{11}$; or $Ar_2$ stands for an aryl group which is optionally substituted with n radicals independently selected from R'$_9$ and from one radical $R_{10}$; or stands for a 5-ring-membered heteroaryl group comprising as ring members 1 to 4 heteroatoms selected from nitrogen, oxygen or sulfur and being optionally substituted with n radicals independently selected from $R_{11}$; or stands for a 6-ring-membered heteroaryl group comprising as ring members 1 to 4 heteroatoms selected from nitrogen, oxygen or sulfur, and being optionally substituted with n radicals independently selected from $R_{11}$; or stands for a fused bicyclic heteroaryl group comprising as ring members 1 to 4 heteroatoms selected from nitrogen, oxygen or sulfur, and being composed from the 5-ring- or 6-ring-membered heteroaryl groups as defined for $Ar_2$ with an annellated phenyl ring or with an annellated second 6-ring-membered heteroaryl, each ring and the bicyclic heteroaryl being optionally substituted with n radicals independently selected from $R_{11}$;

$R_1$ and $R_2$ stand independently of each other for hydrogen or $C_1$-$C_5$alkyl optionally substituted by halogen, $C_1$-$C_3$alkoxy or —NR$_{12}$R$_{13}$; or stand for $C_2$-$C_5$alkenyl optionally substituted by halogen or $C_1$-$C_3$alkoxy; or stand for $C_2$-$C_5$alkynyl; or stand for $C_3$-$C_6$cycloalkyl optionally substituted by halogen, $C_1$-$C_3$alkoxy; $C_1$-$C_3$alkyl or —NR$_{12}$R$_{13}$;

$R_3$ designates hydrogen, $C_3$-$C_5$alkenyl, $C_3$-$C_5$alkynyl or $C_1$-$C_3$alkyl optionally substituted by $C_1$-$C_3$alkoxy; $C_3$-$C_5$alkenyloxy or $C_3$-$C_5$alkynyloxy;

$R_4$ is $C_1$-$C_5$-alkyl optionally substituted by halogen, $C_1$-$C_3$alkoxy or —NR$_{12}$R$_{13}$; or is $C_2$-$C_5$alkenyl optionally substituted by halogen or $C_1$-$C_3$alkoxy; or is $C_2$-$C_5$alkynyl; or is $C_3$-$C_6$cycloalkyl optionally substituted by halogen, $C_1$-$C_3$alkoxy or $C_1$-$C_3$alkyl; or $R_5$ and $R_6$ are independently of each other hydrogen or $C_1$-$C_5$alkyl optionally substituted by halogen, $C_1$-$C_3$alkoxy or —NR$_{12}$R$_{13}$; or are $C_2$-$C_5$alkenyl optionally substituted by halogen or $C_1$-$C_3$alkoxy; or are $C_2$-$C_5$alkynyl; or are $C_3$-$C_6$cycloalkyl optionally substituted by halogen, $C_1$-$C_3$alkoxy; $C_1$-$C_3$alkyl or —NR$_{12}$R$_{13}$;

$R_7$ and $R_8$ are independently of each other hydrogen or $C_1$-$C_5$alkyl optionally substituted by halogen, $C_1$-$C_3$alkoxy or —NR$_{12}$R$_{13}$; or are $C_2$-$C_5$alkenyl optionally substituted by halogen or $C_1$-$C_3$alkoxy; or are $C_2$-$C_5$alkynyl; or are $C_3$-$C_6$cycloalkyl optionally substituted by halogen, $C_1$-$C_3$alkoxy; $C_1$-$C_3$alkyl or —NR$_{12}$R$_{13}$;

$R_9$ and R'$_9$ independently of each other stand for $C_1$-$C_5$alkyl optionally substituted by halogen, $C_1$-$C_4$alkoxy, —NR$_{12}$R$_{13}$, —CO—R$_{14}$ or the acyclic or cyclic ketals and acetals of —CO—R$_{14}$; by a —X-aryl which is optionally substituted by halogen, $C_1$-$C_4$alkyl, $C_1$-$C_4$haloalkyl, $C_1$-$C_4$alkoxy, —CN, —NO$_2$, —NR$_{12}$R$_{13}$, —CO—R$_{14}$ or the acyclic or cyclic ketals and acetals of —CO—R$_{14}$; by a —X-linked-5- or 6-ring-membered heteroaryl group optionally substituted by halogen, $C_1$-$C_4$alkyl, $C_1$-$C_4$haloalkyl, $C_1$-$C_4$alkoxy, —CN, —NO$_2$, —NR$_{12}$R$_{13}$, —CO—R$_{14}$ or the acyclic or cyclic ketals and acetals of —CO—R$_{14}$; or stand for $C_3$-$C_6$cycloalkyl, optionally substituted by halogen, hydroxy, =O, $C_1$-$C_4$alkoxy, NR$_{12}$R$_{13}$; or stand for $C_1$-$C_4$alkoxy optionally substituted by halogen, $C_1$-$C_4$alkoxy, by —X-aryl which is optionally substituted by halogen, $C_1$-$C_4$alkyl, $C_1$-$C_4$haloalkyl, $C_1$-$C_4$alkoxy, —CN, —NO$_2$, —NR$_{12}$R$_{13}$, —CO—R$_{14}$ or the acyclic or cyclic ketals and acetals of —CO—R$_{14}$; by a X-linked-5- or 6-ring-membered heteroaryl group optionally substituted by halogen, $C_1$-$C_4$alkyl, $C_1$-$C_4$haloalkyl, $C_1$-$C_4$alkoxy, —CN, —NO$_2$, —NR$_{12}$R$_{13}$, —CO—R$_{14}$ or the acyclic or cyclic ketals and acetals of —CO—R$_{14}$; or stand for $C_2$-$C_5$alkenyl optionally substituted by halogen or aryl; or stand for $C_2$-$C_5$alkynyl optionally substituted by halogen, tri-alkyl-silyl or aryl; or stand for $C_2$-$C_5$alkenyloxy optionally substituted by halogen or aryl; or stand for $C_2$-$C_5$alkynyloxy optionally substituted by halogen, tri-alkyl-silyl or aryl; or stand for $C_3$-$C_6$cycloalkoxy optionally substituted by $C_1$-$C_3$alkyl, halogen or $C_1$-$C_4$alkoxy; or stand for halogen; or stand for —NR$_{12}$R$_{13}$; or stand for —NR$_2$—CO—R$_{12}$; or stand for —NR$_2$—CO—OR$_{12}$; or stand for —NR$_2$—CO—NR$_8$R$_9$; or stand for —NR$_2$—CO—SR$_{12}$; or stand for —NR$_2$—CS—OR$_{12}$; or stand for —NR$_2$—CS—NR$_8$R$_9$; or stand for —NR$_2$—CS—SR$_{12}$; or stand for —NR$_2$—C(=N—O—R$_{12}$)—S—OR$_{12}$; or stand for —NR$_2$—C(=N—O—R$_{12}$)—NR$_8$R$_9$; or stand for —NR$_2$—C(=N—O—R$_{12}$)—SR$_{12}$; or stand for —S(O)$_p$—$C_1$-$C_4$alkyl optionally substituted by halogen; or stand for —NR$_2$—SO$_2$—NR$_8$R$_9$; or stand for nitro, for cyano or for —CS—NH$_2$;

R$_{10}$ stands for hydrogen; or stands for —X-aryl which is optionally substituted by halogen, $C_1$-$C_4$alkyl, $C_1$-$C_4$haloalkyl, $C_1$-$C_4$alkoxy, —CN, —NO$_2$, —NR$_{12}$R$_{13}$, —CO—R$_{14}$ or the acyclic or cyclic ketals and acetals of —CO—R$_{14}$; or stands for a X-linked 5-membered aromatic or non-aromatic heterocyclic ring comprising nitrogen, oxygen or sulfur as ring members and being optionally substituted by halogen, $C_1$-$C_4$alkyl, $C_1$-$C_4$haloalkyl, $C_1$-$C_4$alkoxy, —CN, —NO$_2$, —NR$_{12}$R$_{13}$, —CO—R$_{14}$ or the acyclic or cyclic ketals and acetals of —CO—R$_{14}$; or stands for a X-linked 6-membered aromatic or non-aromatic heterocyclic ring comprising nitrogen, oxygen or sulfur as ring members and being optionally substituted by halogen, $C_1$-$C_4$alkyl, $C_1$-$C_4$haloalkyl, $C_1$-$C_4$alkoxy, —CN, —NO$_2$, —NR$_{12}$R$_{13}$, —CO—R$_{14}$ or the acyclic or cyclic ketals and acetals of —CO—R$_{14}$; or stands for —CO—R$_{14}$ or the acyclic or cyclic ketals and acetals of —CO—R$_{14}$; or stands for —O—CO—R$_{14}$; or stands for —C(=N—O—R$_{12}$)—R$_{14}$; R$_{10}$ and one R'$_9$ together form a 3- or 4-membered non-aromatic bridge forming an annellated ring which may contain a carbonyl function or nitrogen, oxygen or sulfur as ring members and is optionally substituted by $C_1$-$C_3$alkyl;

R$_{11}$ is hydrogen, halogen, $C_1$-$C_4$alkyl, $C_1$-$C_4$haloalkyl, $C_1$-$C_4$alkoxy, —NR$_{12}$R$_{13}$, —NO$_2$, —CN, —CO—R$_{14}$ or the acyclic or cyclic ketals and acetals of —CO—R$_{14}$;

W designates a bridge selected from —O—, —S(O)$_m$— or —NR$_3$—;

X designates a direct bond or a bridge selected from —O—, —S(O)$_m$— or —NR$_3$—;

a stands for a number 1, 2 or 3;

b stands for a number 1, 2 or 3;

c stands for a number zero, 1 or 2;

m stands for a number zero, 1 or 2;

n stands for a number 1 or 2;

p stands for a number zero, 1 or 2;

R$_{12}$ and R$_{13}$ independently of each other stand for hydrogen; $C_1$-$C_5$alkyl optionally substituted by halogen, $C_1$-$C_4$haloalkyl, $C_1$-$C_4$alkoxy, $C_1$-$C_4$alkylamino, di($C_1$-$C_4$alkyl)amino, or aryl which in turn is optionally substituted by halogen, $C_1$-$C_4$alkyl, $C_1$-$C_4$haloalkyl, $C_1$-$C_4$alkoxy or —CN; or stand for $C_3$-$C_5$alkenyl optionally substituted by halogen, $C_1$-$C_4$haloalkyl, $C_1$-$C_4$alkoxy, $C_1$-$C_4$alkylamino, di($C_1$-$C_4$alkyl)amino, or aryl which in turn is optionally substituted by halogen, $C_1$-$C_4$alkyl, $C_1$-$C_4$haloalkyl, $C_1$-$C_4$alkoxy or —CN; or stand for $C_3$-$C_5$alkynyl optionally substituted by halogen, $C_1$-$C_4$haloalkyl, $C_1$-$C_4$alkoxy, $C_1$-$C_4$alkylamino, di($C_1$-$C_4$alkyl)amino, or aryl which in turn is optionally substituted by halogen, $C_1$-$C_4$alkyl, $C_1$-$C_4$haloalkyl, $C_1$-$C_4$alkoxy or —CN; or together form a 5-ring-membered non-aromatic carbocyclic ring; or together form a 6-ring-membered non-aromatic carbocyclic ring which is interrupted by —O— or —N($C_1$-$C_4$alkyl)—; and R$_{14}$ stands for $C_1$-$C_5$alkyl optionally substituted by halogen, $C_1$-$C_4$alkoxy, $C_1$-$C_4$alkylamino, di($C_1$-$C_4$alkyl)amino; aryl which in turn is optionally substituted by halogen, $C_1$-$C_4$alkyl, $C_1$-$C_4$haloalkyl, $C_1$-$C_4$alkoxy, —CN, —NO$_2$, $C_1$-$C_4$alkylamino, di($C_1$-$C_4$alkyl)amino or $C_1$-$C_4$alkylcarbonyl, $C_1$-$C_4$alkoxycarbonyl, $C_1$-$C_4$alkylaminocarbonyl or di($C_1$-$C_4$alkyl)aminocarbonyl; or by a 5- or 6-ring hetero-aromatic ring which in turn is optionally substituted by halogen, $C_1$-$C_4$alkyl, $C_1$-$C_4$haloalkyl $C_1$-$C_4$alkoxy, —CN, —NO$_2$, $C_1$-$C_4$alkylamino, di($C_1$-$C_4$alkyl)amino, $C_1$-$C_4$alkylcarbonyl, $C_1$-$C_4$alkoxycarbonyl, $C_1$-$C_4$alkylaminocarbonyl or di-($C_1$-$C_4$alkyl)aminocarbonyl; or stands for $C_3$-$C_6$cycloalkyl optionally substituted by halogen, hydroxy, =O, $C_1$-$C_4$alkoxy or $C_1$-$C_4$alkylamino, di($C_1$-$C_4$alkyl)amino; or stands for $C_1$-$C_4$alkoxy optionally substituted by halogen, $C_1$-$C_4$alkoxy; $C_1$-$C_4$alkylamino, di($C_1$-$C_4$alkyl)amino; or stands for phenyl which is optionally substituted by halogen, $C_1$-$C_4$alkyl, $C_1$-$C_4$haloalkyl, $C_1$-$C_4$alkoxy, —CN, —NO$_2$, $C_1$-$C_4$alkylamino, di($C_1$-$C_4$alkyl)amino, $C_1$-$C_4$alkylcarbonyl, $C_1$-$C_4$alkoxycarbonyl, $C_1$-$C_4$alkylaminocarbonyl or di-($C_1$-$C_4$alkyl)aminocarbonyl; or stands for a 5- or 6-ring membered heteroaryl comprising nitrogen, oxygen or sulfur as ring members and being optionally substituted by halogen, $C_1$-$C_4$alkyl, $C_1$-$C_4$haloalkyl; $C_1$-$C_4$alkoxy, —CN, —NO$_2$, $C_1$-$C_4$alkylamino, di($C_1$-$C_4$alkyl)amino, $C_1$-$C_4$alkylcarbonyl, $C_1$-$C_4$alkoxycarbonyl, $C_1$-$C_4$alkylaminocarbonyl or di-($C_1$-$C_4$alkyl)aminocarbonyl.

In the above definitions "halo" or "halogen" includes fluorine, chlorine, bromine and iodine. The alkyl, alkenyl and alkynyl radicals may be straight-chain or branched. This applies also to the alkyl, alkenyl or alkynyl parts of other alkyl-, alkenyl- or alkynyl-containing groups, such as alkoxy, alkylthio, alkylamino and dialkylamino.

Depending upon the number of carbon atoms mentioned, alkyl on its own or as part of another substituent is to be understood as being, for example, methyl, ethyl, propyl, butyl, pentyl, hexyl, heptyl, octyl, nonyl, decyl, undecyl, dodecyl and the isomers thereof, for example isopropyl, isobutyl, tert-butyl or sec-butyl, isopentyl or tert-pentyl.

Cycloalkyl for example is, depending upon the number of carbon atoms mentioned, cyclopropyl, cyclobutyl, cyclopentyl, cyclohexyl, bicyclohexyl, cycloheptyl, bicycloheptyl, cyclooctyl or bicyclooctyl.

Depending upon the number of carbon atoms mentioned, alkenyl as a group or as a structural element of other groups is to be understood as being, for example, ethenyl, allyl, 1-propenyl, buten-2-yl, buten-3-yl, penten-1-yl, penten-3-yl, hexen-1-yl, 4-methyl-3-pentenyl or 4-methyl-3-hexenyl.

Alkynyl as a group or as a structural element of other groups is, for example, ethynyl, propyn-1-yl, propyn-2-yl, butyn-1-yl, butyn-2-yl, 1-methyl-2-butynyl, hexyn-1-yl, 1-ethyl-2-butynyl or octyn-1-yl, depending on the number of carbon atoms present.

A haloalkyl, haloalkenyl, haloalkynyl or halocycloalkyl group may contain one or more (identical or different) halogen atoms, and for example may stand for $CHCl_2$, $CH_2F$, $CCl_3$, $CH_2Cl$, $CHF_2$, $CF_3$, $CH_2CH_2Br$, $C_2Cl_5$, $CH_2Br$, $CHClBr$, $CF_3CH_2$, $CH_2CH_2Cl$, $CH_2CH_2F$, $CH_2CHF_2$, $CH_2-C=CHCl$, $CH=CCl_2$, $CH=CF_2$, $CH_2-C\equiv CCl$, $CH_2-C\equiv C-CF_3$, chlorocyclohexyl, dichlorocyclohexyl, etc.

Alkoxy thus includes methoxy, ethoxy, propoxy, isopropoxy, n-butyloxy, s-butyloxy, i-butyloxy or t-butyloxy.

$Ar_1$ and $Ar_2$ according to the present invention both present aromatic moieties, belonging to the chemical class of aromatic hydrocarbons or aromatic heterocycles, designated as aryl or heteroaryl.

The definition aryl includes aromatic hydrocarbon ring systems like phenyl, naphthyl, anthracenyl, phenanthrenyl and biphenyl like 1,3-biphenyl and 1,4-biphenyl, with phenyl being preferred. The same definition applies where aryl is part of aryloxy.

Heteroaryl stands for monocyclic aromatic ring systems comprising 1 to 4 heteroatoms selected from N, O and S, where it is understood that the for reasons of complying with the aromatic character of the heteroaryl rings 1 to 4 nitrogen atoms may be present in one ring, but in general not more than one of them may be replaced by oxygen or sulfur. However for the purposes of defining $Ar_2$ heteroaryl includes bicyclic aromatic ring systems comprising an aromatic 5- to 6-membered ring heterocycle condensed with another aromatic 6-membered ring, either an heterocycle or a benzene ring. Where condensed ring systems of more than one ring is intended this is especially pointed out, for example by mentioning condensation, including annellation with benzene rings Typical examples for 5-rings, 6-rings and bicyclic condensed systems are furyl, thienyl, pyrrolyl, imidazolyl, pyrazolyl, thiazolyl, isothiazolyl, oxazolyl, isoxazolyl, oxadiazolyl, thiadiazolyl, triazolyl, tetrazolyl, pyridyl, pyridazinyl, pyrimidinyl, pyrazinyl, triazinyl, tetrazinyl, indolyl, benzothienyl, benzofuryl, isobenzothienyl, isobenzofuryl, benzimidazolyl, benzopyrazolyl, indazolyl, benzotriazolyl, benzothiazolyl, benzoisothiazolyl, benzoxazolyl, benzisoxazolyl, quinolinyl, isoquinolinyl, phthalazinyl, purinyl, naphthridinyl, pteridinyl, quinoxalinyl, quinazolinyl and cinnolinyl. Preferred heterocycles are furyl, thienyl, pyrrolyl, imidazolyl, thiazolyl, oxazolyl, isoxazolyl, oxadiazolyl, thiadiazolyl, triazolyl, pyridyl, pyridazinyl, pyrimidinyl, pyrazinyl, indolyl, benzothienyl, benzofuryl, benzopyrazolyl, benzothiazolyl, benzoxazolyl, benzisoxazolyl, quinolinyl, isoquinolinyl and quinazolinyl.

Depending on the position of the heteroaryl group, the heterocyclic ring may be linked to the basic molecular structure via a ring-carbon atom or via a nitrogen-ring atom.

The aryl and heteroaryl groups according to the invention may be unsubstituted or are optionally substituted. Where substituents are indicated according to this invention, the ring structures may carry one or more identical or different substituents. Normally not more than three substituents are present at the same time. Examples of substituents of aryl or heteroaryl groups are: alkyl, alkenyl, alkynyl, cycloalkyl, alkylamino, dialkylamino, cyano, nitro, amino, hydroxy, cycloalkyl-alkyl, aryl, arylalkyl, heteroaryl, heteroarylalkyl, phenyl and phenyl-alkyl, it being possible in turn for all of the preceding groups to carry one or more identical or different halogen atoms; alkoxy; alkenyloxy; alkynyloxy; alkoxyalkyl; haloalkoxy, alkylthio; haloalkylthio; alkylsulfonyl; formyl; alkanoyl; hydroxy; halogen; cyano; nitro; amino; hydroxy, alkylamino; dialkylamino; carboxyl; alkoxycarbonyl; alkenyloxycarbonyl; or alkynyloxycarbonyl.

Typical examples include 1-naphthyl, 2,3-dichlorophenyl, 2,3-difluorophenyl, 2,4,6-trichlorophenyl, 2,4,6-trifluorophenyl, 2,4-dichlorophenyl, 2,4-difluorophenyl, 2,5-dichlorophenyl, 2,5-difluorophenyl, 2,6-dichlorophenyl, 2-chloro-4-ethoxyphenyl, 2-chloro-4-methoxyphenyl, 2-chlorophenyl, 2-ethoxyphenyl, 2-fluoro-4-chlorophenyl, 2-fluoro-4-ethoxyphenyl, 2-fluoro-4-methoxyphenyl, 2-hexyloxyphenyl, 2-methoxy-4-chlorophenyl, 2-methoxyphenyl, 2-methyl-4-chlorophenyl, 2-naphthyl, 2-trifluoromethyl, 3,4,5-trichlorophenyl, 3,4-dibromophenyl, 3,4-dichlorophenyl, 3,4-difluorophenyl, 3,4-dimethoxyphenyl, 3,4-dimethylphenyl, 3,5-dimethyl-4-chlorophenyl, 3'4'-dichloro-4-biphenylyl, 3-bromo-4-methylphenyl, 3-bromophenyl, 3-chloro-4-cyanophenyl, 3-chloro-4-ethoxyphenyl, 3-chloro-4-fluorophenyl, 3-chloro-4-methoxyphenyl, 3-chlorophenyl, 3-ethyl-4-chlorophenyl, 3-fluoro-4-ethoxyphenyl, 3-fluoro-4-methoxyphenyl, 3-fluoro-4-methoxyphenyl, 3-methoxy-4-chlorophenyl, 3-methylphenyl, 4-(1,3,4-oxadiazol-2-yl)phenyl, 4-(1-imidazolyl)-phenyl, 4-(1-methyl-methoximinomethyl)-phenyl, 4-(2,6-dimethoxypyrimidin-2-ylthio)-phenyl, 4-(2-cyanopyrid-4-yl)-phenyl, 4-(3-methyl-1,2,4-thiadiazol-4-2-yloxy)phenyl, 4-(3-methyl-1,2,4-thiazol-5-yloxy)-phenyl, 4-(5-ethyl-1,3,4-oxadiazol-2-yl)phenyl, 4-(pyrid-2yloxy)-phenyl, 4'-bromo-4-biphenylyl, 4'-chloro-4-biphenylyl, 4'-cyano-4-biphenylyl, 4'-methyl-4-biphenylyl, 4'-trifluoromethyl-4-biphenylyl, 4-aminocarbonylethoxy-phenyl, 4-aminocarbonylmethylphenyl, 4-aminocarbonyl-phenyl, 4-biphenylyl, 4-bromo-3-chlorophenyl, 4-bromophenyl, 4-chloro-3-cyanophenyl, 4-chloro-3-fluorophenyl, 4-chloro-3-methylphenyl, 4-chloro-3-trifluoromethyl-phenyl, 4-chlorophenyl, 4-cyanophenyl, 4-cyclohexylphenyl, 4-ethenylphenyl, 4-ethoxyphenyl, 4-ethylphenyl, 4-ethynyloxyphenyl, 4-ethynylphenyl, 4-fluorophenyl, 4-hexyloxyphenyl, 4-isopropylcarbonylamino-phenyl, 4-isopropylphenyl, 4-isopropoxyphenyl, 4-methoxy-3-methylphenyl, 4-methoxycarbonyl-phenyl, 4-methoxyphenyl, 4-methylphenyl, 4-methylsulfonyl-phenyl, 4-methylthiophenyl, 4-nitrophenyl, 4-N-morpholinocarbonylaminophenyl, 4-N-morpholinocarbonyloxyethoxy-phenyl, 4-phenoxyphenyl, 4-propargyloxyphenyl, 4-propylphenyl, 4-tert.-butylcarbonylaminophenyl, 4-tert.butylphenyl, 4-trifluoromethoxyphenyl, 4-trifluoromethylphenyl, 5-chloro-thien-2-yl, 5-methyl-fur-2-yl, 5-methyl-thien-2-yl, 6-benzothienyl, 7-benzothienyl, etc.

Where $R_{10}$ and $R'_9$ together form a bridge the bridge is normally between vicinal carbon atom of $Ar_2$. Thus annellated ring structures are formed, which may be substituted with one or two lower alkyl groups, preferably methyl. The bridge includes —$(CH_2)_3$—, —$(CH_2)_4$—, —O—$(CH_2)_3$—, —CO—$(CH_2)_3$—, —S—$(CH_2)_3$—, —NH—$(CH_2)_3$—, —O—$(CH_2)_2$—, —O—$(CH_2)_2$—O—, —O—$CH_2$—CH($CH_3$)—O—, —O—$CH_2$—O—, —CO—$(CH_2)_2$—, —S—$(CH_2)_2$—, —NH—$(CH_2)_2$—, —$CH_2$—O—$CH_2$—, —$CH_2$—CO—$CH_2$—, —$CH_2$—S—$CH_2$—, —$CH_2$—NH—$CH_2$—, —CO—O—$(CH_2)_2$—, —CO—NH—$(CH_2)_2$—, —NH—CO—$(CH_2)_2$—, —$CH_2$—CO—O—$CH_2$—, —CO—S—$(CH_2)_2$—, —NH—CO—$CH_2$—, —O—CO—$(CH_2)_2$—, —$CH_2$—CO—O—, —$CH_2$—O—CO—, —S—CO—$(CH_2)_2$—, —CO—NH—$CH_2$— and —$CH_2$—CO—NH—$CH_2$—, etc.

Where the acetals or ketals of —CO—$R_{14}$ are intended the acetals and ketals may appear as —C($C_1$-$C_4$alkoxy)$_2$—$R_{14}$ or as cyclic structures wherein the former carbonyl carbon atom carries a dioxoalkylene bridge of the type —O—$C_1$-$C_3$alkylene-O— which optionally may be branched, including —O—$CH_2$—O—, —O—CH($CH_3$)—O—, —O—$(CH_2)_2$—O—, —O—$(CH_2)_3$—O—, —O—$CH_2$—CH($CH_3$)—O—, and the like.

Where $R_{12}$ and $R_{13}$ together with the nitrogen binding the two radicals may form a non-aromatic carbocyclic ring this radical stands for pyrrolidine, piperidine, morpholine or thiomorpholine ring, which may be substituted by one or two methyl groups.

The presence of at least one asymmetric carbon atom in the compounds of formula I means that the compounds may occur in optically isomeric, diastereomeric and enantiomeric forms. As a result of the presence of a possible aliphatic C=C double bond, geometric isomerism may also occur. Formula I is intended to include all those possible isomeric forms and mixtures thereof. Where no specific isomer is specified the mixtures of diastereomers, enantiomers or the racemate are meant, as obtainable from the disclosed synthesis methods. The optical isomers, diastereomers and enantiomers of formula I may be obtained in pure form either by isolation from the mixture by suitable separation methods, which are known in the art, or may be obtained by stereoselective synthesis methods.

Preferred subgroups of compounds of formula I are those wherein $Ar_1$ stands for optionally substituted aryl group; or $Ar_1$ is optionally substituted phenyl; or $Ar_2$ stands for optionally substituted aryl; or $Ar_2$ is optionally substituted phenyl; or $Ar_1$ and $Ar_2$ independently of each other stand for optionally substituted phenyl; or the optional substituents $R_9$ of $Ar_1$ are preferably selected from the group comprising halogen, $C_1$-$C_4$alkyl, $C_1$-$C_4$haloalkyl, $C_1$-$C_4$alkoxy, $C_1$-$C_4$haloalkoxy, $C_3$-$C_6$cycloalkyl, —CN and —CO—$R_{14}$; or the optional substituents $R'_9$ of $Ar_2$ are preferably selected from the group comprising halogen, $C_1$-$C_4$alkyl, $C_1$-$C_4$haloalkyl, $C_1$-$C_4$alkoxy, $C_1$-$C_4$haloalkoxy, $C_3$-$C_6$cycloalkyl, —CN, —CO—$R_{14}$, —$NR_{12}R_{13}$, —$NR_2$—CO—$R_{12}$, —$NR_3$—CO—$OR_{12}$, —$NR_2$—CO—$NR_8R_9$, —$NR_2$—CO—$SR_{12}$, —$NR_2$—CS—$OR_{12}$, —$NR_2$—CS—$NR_8R_9$, —$NR_2$—CS—$SR_{12}$, —$S(O)_p$—$C_1$-$C_4$alkyl, —$S(O)_p$—$C_1$-$C_4$haloalkyl, —$NR_2$—$SO_2$—$NR_8R_9$, nitro, cyano and —CS—$NH_2$; or the optional substituents $R_9$ and $R'_9$ of $Ar_1$ and $Ar_2$ are selected from the group comprising $C_1$-$C_4$alkyl, $C_1$-$C_4$haloalkyl, $C_1$-$C_4$alkoxy, $C_1$-$C_4$haloalkoxy and $C_3$-$C_6$cycloalkyl; or the optional substituents $R_9$ and $R'_9$ of $Ar_1$ and $Ar_2$ are selected from the group comprising bromo, chloro, fluoro, iodo, cyano, hydroxy, amino, nitro, methyl, ethyl, propyl, isopropyl, methoxy, ethoxy, propoxy, isopropoxy, allyloxy, propargyloxy, benzyloxy, trifluoromethyl, trifluoromethoxy, 2-cyano-2-methyl-butyloxy, methylsulfonyl, methylsulfinyl, methylthio, cyclopentyl, cyclohexyl, aminocarbonylmethyl, methoximinoethyl, aminocarbonyl, butylcarbonylamino, tert-butylcarbonylamino, triazol-1-ylmethyl, 1,2,4-triazol-1-ylmethyl, N-morpholinocarbonylamino, aminocarbonyloxy-ethoxy, morpholinocarbonyloxyethoxy and cyanopyridyloxyethoxy; or the optional substituents $R_9$ and $R'_9$ of $Ar_1$ and $Ar_2$ are selected from the group comprising bromo, chloro, fluoro, methyl, ethyl, methoxy, ethoxy, trifluoromethyl and trifluoromethoxy; or the optional substituent $R_{10}$ on $Ar_2$ is selected from optionally substituted phenyl, optionally substituted imidazolyl, optionally substituted thiazolyloxy, optionally substituted pyridyloxy, optionally substituted pyridyl, optionally substituted pyrimidinyloxy, optionally substituted pyrimidinyl, optionally substituted oxadiazolyl, optionally substituted triazolyl, optionally substituted pyrazolyl, optionally substituted oxadiazolyloxy, optionally substituted triazolyloxy and optionally substituted pyrazolyloxy; or the optional substituent $R_{10}$ on $Ar_2$ is selected from halogen, $C_1$-$C_4$alkyl, $C_1$-$C_4$haloalkyl, $C_1$-$C_4$alkoxy, —CN, —$NO_2$, —$NR_{12}R_{13}$, —CO—$R_{14}$ and the acyclic or cyclic ketals and acetals of —CO—$R_{14}$; or the optional substituent $R_{10}$ on $Ar_2$ is selected from —CO—$R_{14}$, —O—$R_{14}$, optionally substituted phenyl, optionally substituted phenoxy, optionally substituted imidazolyl, optionally substituted imidazolyloxy, optionally substituted thiazolyloxy, optionally substituted thiazolyl, optionally substituted thiadiazolyloxy, optionally substituted thiadiazolyl, optionally substituted pyridyloxy, optionally substituted pyridyl, optionally substituted pyrimidinyloxy, optionally substituted pyrimidinyl, optionally substituted oxadiazolyl, optionally substituted oxadiazolyloxy, optionally substituted triazolyl, optionally substituted pyrazolyl, optionally substituted triazolyloxy and optionally substituted pyrazolyloxy; or the optional substituent $R_{10}$ on $Ar_2$ is selected from —CO—$C_1$-$C_4$alkyl, —O—CO—$C_1$-$C_4$alkyl and —CO—$C_1$-$C_4$alkoxy; or the optional substituent $R_{10}$ on $Ar_2$ is selected from aminocarbonyl, dimethylaminocarbonyl, acetyl, propionyl, acetoxy, methoxycarbonyl, ethoxycarbonyl, benzoyl, methoximinoethyl, 1-imidazolyl, 5-(3-methyl-1,2,4-thiadiazolyloxy), 2-pyridyl, 2-pyridyloxy, 4-pyrimidinyl, 2-(3,5-dichloropyridyloxy), 2-(4,6-dichloropyridyloxy), 2-(4,6-dimethoxypyrimidinylthio), 2-oxadiazolyl, 2-(5-methyl-oxadazolyl), 2-(5-ethyl-oxadiazolyl), 1-triazolyl, 1-pyrazolyl, 1-(3,4-dimethylpyrazolyl), 4-(2-methylthiazolyl), 2-(1,3,4-oxydiazolyl), N-pyrrolidin-2-onyl, and 2-quinoxalinyl, or $R_1$, $R_2$, $R_5$, $R_6$, $R_7$ and $R_8$ independently of each other stand for hydrogen or methyl; or $R_1$ and $R_5$ are independently of each other $C_1$-$C_4$alkyl and $R_2$ and $R_6$ are hydrogen; or $R_3$ is hydrogen or $C_1$-$C_4$alkyl optionally substituted with $C_1$-$C_4$alkoxy, $C_3$-$C_4$alkenyloxy, or $C_3$-$C_4$alkynyloxy; or $R_3$ is hydrogen, $C_1$-$C_4$alkyl or $C_1$-$C_4$alkoxy-$C_1$-$C_4$alkyl; or $R_4$ is hydrogen or $C_1$-$C_4$alkyl optionally substituted with halogen, $C_1$-$C_3$alkoxy, $C_1$-$C_3$alkylamino or di-$C_1$-$C_3$alkylamino; or $R_4$ is hydrogen, $C_1$-$C_4$alkyl or $C_1$-$C_4$haloalkyl or
$R_4$ is $C_1$-$C_4$alkyl or $C_1$-$C_4$haloalkyl; or
W is —O—; or
X is a direct bond; or
the suffixes (a) and (b) designate the number 1; or
the suffix (c) stands for the number zero.

One preferred subgroup of formula I is wherein $Ar_1$ and $Ar_2$ independently of each other stand for optionally substituted phenyl; and the optional substituents $R_9$ of $Ar_1$ are preferably selected from the group comprising halogen, $C_1$-$C_4$alkyl, $C_1$-$C_4$haloalkyl, $C_1$-$C_4$alkoxy, $C_1$-$C_4$haloalkoxy, $C_3$-$C_6$cycloalkyl, —CN and —CO—$R_{14}$; and the optional substituents $R'_9$ of $Ar_2$ are preferably selected from the group comprising halogen, $C_1$-$C_4$alkyl, $C_1$-$C_4$haloalkyl, $C_1$-$C_4$alkoxy, $C_1$-$C_4$haloalkoxy, $C_3$-$C_6$cycloalkyl, —CN, —CO—$R_{14}$, —$NR_{12}R_{13}$, —$NR_2$—CO—$R_{12}$, —$NR_3$—CO—$OR_{12}$, —$NR_2$—CO—$NR_8R_9$, —$NR_2$—CO—$SR_{12}$, —$NR_2$—CS—$OR_{12}$, —$NR_2$—CS—$NR_8R_9$, —$NR_2$—CS—$SR_{12}$, —$S(O)_p$—$C_1$-$C_4$alkyl, —$S(O)_p$—$C_1$-$C_4$haloalkyl, —$NR_2$—$SO_2$—$NR_8R_9$, nitro, cyano and —CS—$NH_2$; and the optional substituent $R_{10}$ on $Ar_2$ is selected from optionally substituted phenyl, optionally substituted imidazolyl, optionally substituted thiazolyloxy, optionally substituted pyridyloxy, optionally substituted pyridyl, optionally substituted pyrimidinyloxy, optionally substituted pyrimidinyl, optionally substituted oxadiazolyl, optionally substituted triazolyl, optionally substituted pyrazolyl, optionally substituted oxadiazolyloxy, optionally substituted triazolyloxy and optionally substituted pyrazolyloxy.

Further preferred subgroups are those wherein

A) $Ar_1$ and $Ar_2$ independently stand for optionally substituted aryl groups; and
the optional substituents $R_9$ of $Ar_1$ are preferably selected from the group comprising halogen, $C_1$-$C_4$alkyl, $C_1$-$C_4$haloalkyl, $C_1$-$C_4$alkoxy, $C_1$-$C_4$haloalkoxy, $C_3$-$C_6$cycloalkyl, —CN and —CO—$R_{14}$; and
the optional substituents $R_{9'}$ of $Ar_2$ are preferably selected from the group comprising halogen, $C_1$-$C_4$alkyl, $C_1$-$C_4$haloalkyl, $C_1$-$C_4$alkoxy, $C_1$-$C_4$haloalkoxy, $C_3$-$C_6$cycloalkyl, —CN, —CO—$R_{14}$, —$NR_{12}R_{13}$, —$NR_2$—CO—$R_{12}$, —$NR_3$—CO—$OR_{12}$, —$NR_2$—CO—$NR_8R_9$, —$NR_2$—CO—$SR_{12}$, —$NR_2$—CS—$OR_{12}$, —$NR_2$—CS—$NR_8R_9$, —$NR_2$—CS—$SR_{12}$, —$S(O)_p$—$C_1$-$C_4$alkyl, —$S(O)_p$—$C_1$-$C_4$haloalkyl, —$NR_2$—$SO_2$—$NR_8R_9$, nitro, cyano and —CS—$NH_2$; and
the optional substituent $R_{10}$ on $Ar_2$ is selected from halogen, $C_1$-$C_4$alkyl, $C_1$-$C_4$haloalkyl, $C_1$-$C_4$alkoxy, —CN, —$NO_2$, —$NR_{12}R_{13}$, —CO—$R_{14}$ and the acyclic or cyclic ketals and acetals of —CO—$R_{14}$; —O—CO—$R_{14}$, optionally substituted phenyl, optionally substituted imidazolyl, optionally substituted thiazolyloxy, optionally substituted pyridyloxy, optionally substituted pyridyl, optionally substituted pyrimidinyloxy, optionally substituted pyrimidinyl, optionally substituted oxadiazolyl, optionally substituted triazolyl, optionally substituted pyrazolyl, optionally substituted oxadiazolyloxy, optionally substituted triazolyloxy and optionally substituted pyrazolyloxy; and
$R_1$, $R_2$, $R_5$, $R_6$, $R_7$ and $R_8$ independently of each other are hydrogen or methyl; and
$R_3$ is hydrogen or $C_1$-$C_4$alkyl optionally substituted with $C_1$-$C_4$alkoxy, $C_3$-$C_4$alkenyloxy, or $C_3$-$C_4$alkynyloxy; and
$R_4$ is hydrogen or $C_1$-$C_4$alkyl optionally substituted with halogen, $C_1$-$C_3$alkoxy, $C_1$-$C_3$alkylamino or di-$C_1$-$C_3$alkylamino; and
W is —O—; and
X is a direct bond; and
the suffixes (a) and (b) designate the number 1; and
the suffix (c) stands for the number zero; or wherein B) $Ar_1$ and $Ar_2$ independently of each other stand for optionally substituted phenyl; and
the optional substituents $R_9$ and $R'_9$ of $Ar_1$ and $Ar_2$ are selected from the group comprising $C_1$-$C_4$alkyl, $C_1$-$C_4$haloalkyl, $C_1$-$C_4$alkoxy, $C_1$-$C_4$haloalkoxy and $C_3$-$C_6$cycloalkyl; and
the optional substituent $R_{10}$ on $Ar_2$ is selected from —CO—$C_1$-$C_4$alkyl, —CO—C—$C_4$alkoxy, —O—CO—$C_1$-$C_4$alkyl, optionally substituted phenyl, optionally substituted phenoxy, optionally substituted imidazolyl, optionally substituted imidazolyloxy, optionally substituted thiazolyloxy, optionally substituted thiazolyl, optionally substituted thiadiazolyloxy, optionally substituted thiadiazolyl, optionally substituted pyridyloxy, optionally substituted pyridyl, optionally substituted pyrimidinyloxy, optionally substituted pyrimidinyl, optionally substituted oxadiazolyl, optionally substituted oxadiazolyloxy, optionally substituted triazolyl, optionally substituted pyrazolyl, optionally substituted triazolyloxy and optionally substituted pyrazolyloxy; and
$R_1$ and $R_5$ are independently $C_1$-$C_4$alkyl and $R_2$ and $R_6$ are hydrogen; and
$R_3$ is hydrogen, $C_1$-$C_4$alkyl or $C_1$-$C_4$alkoxy-$C_1$-$C_4$alkyl; and
$R_4$ is $C_1$-$C_4$alkyl or $C_1$-$C_4$haloalkyl; and
W is —O—; and
X is a direct bond; and
the suffixes (a) and (b) designate the number 1; and
the suffix (c) stands for the number zero; or wherein C) $Ar_1$ and $Ar_2$ independently of each other stand for optionally substituted phenyl; and
the optional substituents $R_9$ and $R'_9$ of $Ar_1$ and $Ar_2$ are selected from the group comprising bromo, chloro, fluoro, iodo, cyano, hydroxy, amino, nitro, methyl, ethyl, propyl, isopropyl, methoxy, ethoxy, propoxy, isopropoxy, allyloxy, propargyloxy, benzyloxy, trifluoromethyl, trifluoromethoxy, 2cyano-2-methyl-butyloxy, methylsulfonyl, methylsulfinyl, methylthio, cyclopentyl, cyclohexyl, aminocarbonylmethyl, methoximinoethyl, aminocarbonyl, butylcarbonylamino, tert-butylcarbonylamino, triazol-1-ylmethyl, 1,2,4-triazol-1-ylmethyl, N-morpholinocarbonylamino, aminocarbonyloxy-ethoxy, morpholinocarbonyloxyethoxy and cyanopyridyloxyethoxy; and
the optional substituent $R_{10}$ on $Ar_2$ is selected from aminocarbonyl, dimethylaminocarbonyl, acetyl, propionyl, acetoxy, methoxycarbonyl, ethoxycarbonyl, benzoyl, methoximinoethyl, 1-imidazolyl, 5-(3-methyl-1,2,4-thiadiazolyloxy), 2-pyridyl, 2-pyridyloxy, 4-pyrimidinyl, 2-(3,5-dichloropyridyloxy), 2-(4,6-dichloropyridyloxy), 2-(4,6-dimethoxypyrimidinylthio), 2-oxadiazolyl, 2-(5-methyl-oxadazolyl), 2-(5-ethyl-oxadiazolyl), 1-triazolyl, 1-pyrazolyl, 1-(3,4-dimethylpyrazolyl), 4-(2-methylthiazolyl), 2-(1,3,4-oxydiazolyl), N-pyrrolidin-2-onyl, and 2-quinoxalinyl, and
$R_1$ and $R_5$ are independently $C_1$-$C_4$alkyl and $R_2$ and $R_6$ are hydrogen; and
$R_3$ is hydrogen, $C_1$-$C_4$alkyl or $C_1$-$C_4$alkoxy-$C_1$-$C_4$alkyl; and
$R_4$ is $C_1$-$C_4$alkyl or $C_1$-$C_4$haloalkyl; and
W is —O—; and
X is a direct bond; and
the suffixes (a) and (b) designate the number 1; and
the suffix (c) stands for the number zero; or wherein D) $Ar_1$ and $Ar_2$ independently of each other stand for optionally substituted phenyl; and the optional substituents $R_9$ and $R'_9$ of $AR_1$ and $AR_2$ are selected from the group comprising bromo, chloro, fluoro, methyl, ethyl, methoxy, ethoxy, trifluoromethyl and trifluoromethoxy; and the optional substituent $R_{10}$ on $Ar_2$ is selected from aminocarbonyl, acetyl, methoxycarbonyl, ethoxycarbonyl, 1-imidazolyl, 5-(3-methyl-1,2,4-thiadiazolyloxy), 2-pyridyl, 2-pyridyloxy, 4-pyrimidinyl, 2-(3,5-dichloropyridyloxy), 2-(4,6-dimethoxypyrimidinylthio), 2-oxadiazolyl, 2-(5-methyl-oxadazolyl), 2-(5-ethyl-oxadiazolyl), 1-triazolyl, 1-pyrazolyl, 4-(2-methylthiazolyl), 2-(1,3,4-oxydiazolyl), and N-pyrrolidin-2-onyl, and $R_1$ and $R_5$ are methyl and $R_2$ and $R_6$ are hydrogen; and $R_3$ is hydrogen, methyl, ethyl, propyl, ethoxymethyl or methoxymethyl, and $R_4$ is methyl, ethyl, propyl or fluoromethyl; and W is —O—; and X is a direct bond; and the suffixes (a) and (b) designate the number 1; and the suffix (c) stands for the number zero.

Preferred individual compounds are:

2-[(4-chlorophenoxy)-methyl]-2-benzylsulfonylamino-propionitrile,

2-[(4-chlorophenoxy)-methyl]-2-[(2-chlorophenyl)-methyl]-sulfonylamino-propionitrile, 2-[(4-chlorophenoxy)-methyl]-2-[(2-fluorophenyl)-methyl]-sulfonylamino-propionitrile, 2-[(4-trifluoromethoxyphenoxy)-methyl]-2-benzylsulfonylamino-propionitrile, 2-[(4-chloro-3-methylphenoxy)-methyl]-2-benzylsulfonylamino-propionitrile, 2-[(4-chlorophenoxy)-methyl]-2-benzylsulfonylamino-butyronitrile, 2-[(4-chlorophenoxy)-methyl]-2-benzylsulfonylamino-3-methoxy-propionitrile, 2-[(4-acetylphenoxy)-methyl]-2-benzylsulfonylamino-propionitrile, 2-[(4-methoxyphenoxy)-methyl]-2-benzylsulfonylamino-propionitrile, 2-[(4-acetylphenoxy)-methyl]-2-benzylsulfonylamino-butyronitrile, 2-[(4-cyanophenoxy)-methyl]-2-benzylsulfonylamino-propionitrile, (−)-2-[(4-cyanophenoxy)-methyl]-2-benzylsulfonylamino-propionitrile, 2-[(4-propionylphenoxy)-methyl]-2-benzylsulfonylamino-propionitrile, 2-[(4-ethoxyphenoxy)-methyl]-2-benzylsulfonylamino-propionitrile, 2-[(4-[1,2,4]triazol-1-yl-phenoxy)-methyl]-2-benzylsulfonylamino-propionitrile, 2-[(4-imidazol-1-yl-phenoxy)-methyl]-2-benzylsulfonylamino-propionitrile, 2-[(4-cyanophenoxy)-methyl]-2-benzylsulfonylamino-butyronitrile, 2-[(4-[1,3,4]oxadiazol-4-yl-phenoxy)-methyl]-2-benzylsulfonylamino-propionitrile, 2-[(4-methoxyphenoxy)-methyl]-2-benzylsulfonylamino-butyronitrile, 2-[(4-ethoxyphenoxy)-methyl]-2-benzylsulfonylamino-butyronitrile, (−)2-[(4-ethoxyphenoxy)-methyl]-2-benzylsulfonylamino-butyronitrile, 2-[(4-[1,2,4]triazol-1-yl-phenoxy)-methyl]-2-benzylsulfonylamino-butyronitrile, 2-[(4-methoxycarbonylphenoxy)-methyl]-2-benzylsulfonylamino-propionitrile, 2-[(4-propionylphenoxy)-methyl]-2-benzylsulfonylaminobutyronitrile, 2-[(4-chlorophenoxy)-methyl]-2-benzylsulfonylamino-3-fluoro-propionitrile, 2-{([4-(2-methyl-thiazol-4-yl)-phenoxy]-methyl}-2-benzylsulfonylamino-butyronitrile, 2-[(4-pyrazol-1-yl-phenoxy)-methyl]-2-benzylsulfonylamino-butyronitrile, 2-(5-oxo-5,6,7,8-tetrahydronaphth-2-yloxy)-methyl]-2-benzylsulfonylamino-butyronitrile, 2-[(4-chloro-phenoxy)-methyl]-2-benzylsulfonylamino-3-methyl-butyronitrile, 2-[(4-iso-propyl-phenoxy)-methyl]-2-benzylsulfonylamino-butyronitrile, 2-[(4-nitro-phenoxy)-methyl]-2-benzylsulfonylamino-butyronitrile, 2-[(4-cyano-phenoxy)-methyl]-2-benzylsulfonylamino-butyronitrile, 2-[(3-fluoro-4-propionyl-phenoxy)-methyl]-2-benzylsulfonylamino-propionitrile, (−)-2-[(4-[1,2,4]triazol-1-yl-phenoxy)-methyl]-2-benzylsulfonylaminobutyronitrile, and (−)-2-[(4-acetylphenoxy)-methyl]-2-benzylsulfonylamino-propionitrile.

Certain sulfonylamido-acetonitriles have been proposed for controlling plant-destructive fungi (for example in EP-A-176327 and EP-A-587110). The biological activity of those compounds is not, however, satisfactory in all aspects and for all needs of the agricultural practices in protecting crop plants.

Surprisingly, with developing the compounds of formula I a new type of microbiocides has been provided which satisfies to a greater extend the need for an agent for controlling phytopathogenic microorganisms on crop plants having a high level of activity, paired with long lasting effective protection.

The compounds of formula I and the respective starting materials may be obtained according to the processes of Schemes 1 to 7.

Scheme 1:

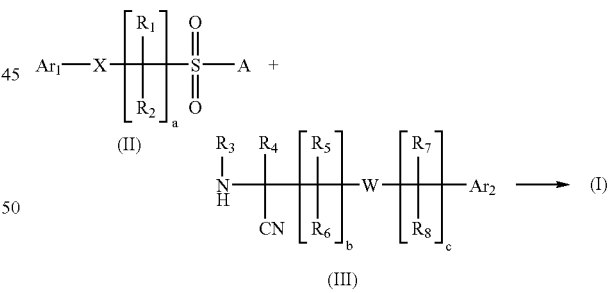

wherein $Ar_1$, $Ar_2$, a, b, c, W and $R_1$ to $R_8$, are defined as under formula I, and A stands for a leaving group like an anhydride, i.e. —O—SO$_2$—(CR$_1$R$_2$)$_a$—X—Ar$_1$ or —O—CO—C$_1$-C$_4$alkyl, but preferably for halogen, especially bromine or more preferably chlorine.

The compounds of formula I may be prepared by sulfonylation of an amino-acetonitrile of formula III with a sulfonyl-halide I anhydride of formula II wherein A is a leaving group, Suitable solvents for this reaction include ketones, such as acetone and methylethylketone, halogenated hydrocarbons such as chloroform, carbontetrachloride, dichloromethane, dichloro-ethane, aromatic hydrocarbons such as toluene or xylene, ethers such as t-butylmethyl-ether, di-ethyl-ether, tetrahydrofuran and dioxane. The reaction is performed preferentially in the presence of a base and a catalyst. Typical bases include tertiary amines such as trimethylamine, triethylamine, diisopropylethylamine, dimethyl-aniline, diazabi-cyclooctane and N-methylmorpholine, aromatic amines such pyridine and quinoline as well as inorganic bases such as alkaline bicarbonates or -carbonates. Typical salts are for example sodium and potassium bicarbonate and sodium, potassium or cesium carbonate. Suitable catalysts such as N,N-dialkyl- or cyloalkyl-aminopyridines, like e.g. 4-N,N-dime-thylaminopyridine, may improve the yield.

The substituents $R_3$ may be introduced into the final active ingredients when starting from the subgroup compounds of formula I wherein $R_3$ is hydrogen, by reacting them e.g. with an alkylating agent $R_3$—A' wherein A' designates a leaving group, preferably a halogen atom, e.g. bromo or chloro. Suitable alkylating agents thus include suitably substituted alkylhalides or alkyl-O-sulfonates, e.g. or alkoxy-alkylhalides. On the other hand, when introducing $R_3$ with the starting compounds of formula III, alkylating of the compounds of the subgroup of formula III, wherein $R_3$ is hydrogen, may be achieved in a similar way by any commonly known alkylation method. Such alkylation prior to sulfonylation with a compound of formula II, as alternative to converting $R_3$ within the final products of formula I, allows to introduce a wide variety of radicals $R_3$ while leaving the choice to decide at which stage such optional conversion is preferably performed.

Cyano-amines of formula III may easily be prepared by the so-called Strecker-Synthesis according to Scheme 2 as described e.g. generically in any textbook on organic chemistry, or in a procedures disclosed in the patent literature (EP-A-953565-A; Nihon Noyaku or U.S. Pat. No. 3,529,019, Colgate-Palmolive) starting from the corresponding ketone of formula IV.

Scheme 2:

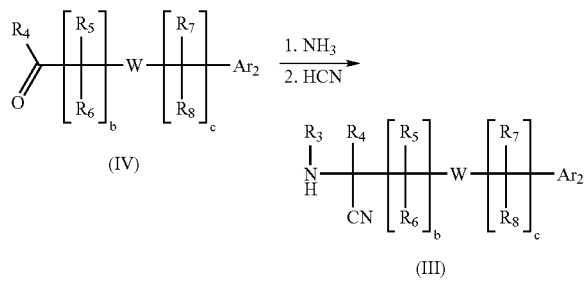

wherein $Ar_2$, b, c, W and $R_5$ to $R_8$ are defined as under formula I and L is a leaving group. The reaction conditions correspond to the standard conditions for preparing aminoacetonitriles by treatment with ammonia and prussic acid.

For the preparation of the ketones of formula IV various methods are known from the literature. Preferably the synthesis is for example conducted in accordance with Scheme 3 by starting from the ketone of formula V, wherein $R_4$, $R_5$, $R_6$ and b are defined as for formula I and L is a leaving group such as e.g. halogen, preferably chlorine, bromine or iodine or a sulfonyloxy group such as e.g. methylsulfonyloxy-, toluylsulfonyloxy- or trifluoromethylsulfonyloxy-group, and reacting it with a compound of formula VI wherein $Ar_2$, $R_7$, $R_8$ and c are defined as for formula I and W' is either an anionic radical species of W such as $O^-$, $S^-$, $S(O)_m^-$ combined with an alkaline- or earthalkaline-metal cation as counterion, or is defined as W—H, e.g. as OH, SH, $NHR_3$. In the latter case the reaction is generally carried out in the presence of a base such as alkaline-, earthalkaline-carbonates or hydrogencarbonates, e.g. sodium or potassium-carbonate, sodium or potassium -hydrogen-carbonate, cesium-carbonate or an agent capable of scavenging the formed acid.

Scheme 3:

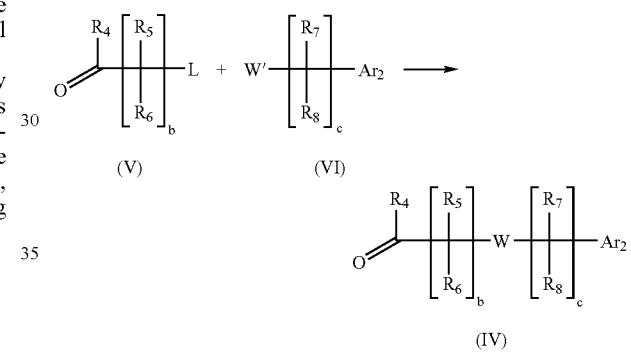

wherein $Ar_2$, b, c, W and $R_4$ to $R_8$, are defined as under formula I and W' is either an anionic radical species of W such as $O^-$, $S^-$, $S(O)_m^-$ combined with an alkaline- or earthalkaline-metal cation as counterion, or is defined as W—H, e.g. as OH, SH, $NHR_3$.

As a typical alternative method of preparing the intermediate ketones of formula (IV) Scheme 3A highlights two of the various pathways.

Scheme 3A:

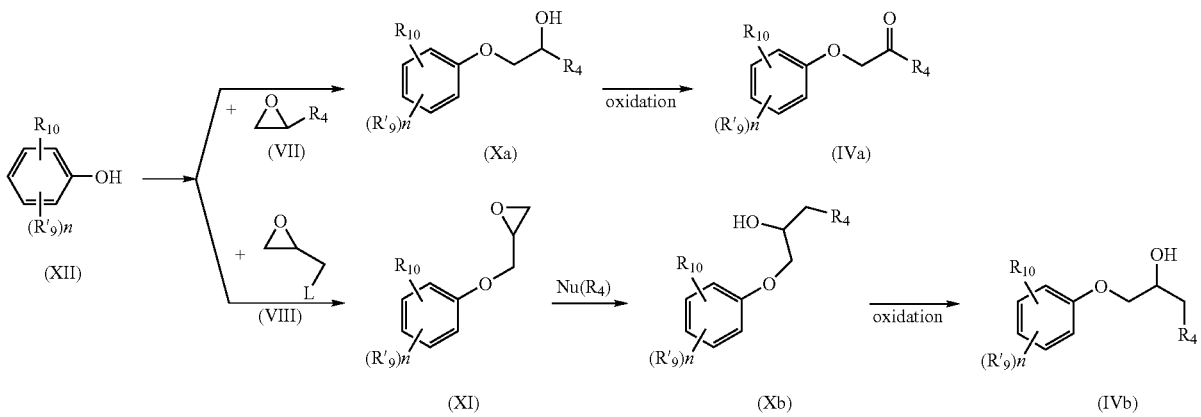

wherein $R_4$, $R'_9$, $R_{10}$ and n are as defined under formula I and L is a leaving group, while $Nu(R_4)$ designates the nucleophilic form of $R_4$, such as alkoxides or halides, especially iodides.

For the sake of simplicity in Scheme 3A the optionally substituted $Ar_2$ is displayed as phenyl, but it is assumed that the entire variation of $Ar_2$ as defined under formula I can be reacted similarly. According to Scheme 3A the selected intermediates of formula IVa may be prepared by oxidizing the corresponding alcohols of formulae Xa and Xb. Advantageous oxidation procedures include the sulfur-based oxidation agents (in literature referred to as Swem-oxidation, Pfizer-Moffat and others), the metal based oxidation agents, hydrogen peroxide in the presence of metal catalysts such as $Na_2WO_4$ (c.f. e.g. R. Noyori, Bull. Chem. Soc. Jpn. 1999, 72, 2287-2306) and others more.

The alcohols of formula Xa and Xb are available by ring-opening of an epoxide of formula VII or an epoxide of formula VIII, e.g. epichlorhydrine with a phenol of formula XII and in the latter case reacting the new intermediate epoxide of formula XI again with a nucleophilic derivative of $Nu(R_4)$ such as alkoxides or halides, especially iodides.

The ring opening reaction may be performed in the presence of a catalyst. Suitable catalysts include bases, such as amines like pyridine, tri-ethanolamine and the like, or metal hydroxides and/or carbonates such as lithium hydroxide, cesium carbonate, potassium carbonate, potassium hydroxide, sodium hydroxide or metal hydrides, such as sodium hydride and lithium hydride or cesium fluoride as well as Lewis acids, such as tetramethylammonium chloride. Suitable solvents include alcohols, such as ethanol, isopropanol, tert-butanol and the like, ketones such as acetone and methyl ethyl ketone, and more polar solvents such as N,N-dimethylformamide, dimethylacetamide and nitriles, such as acetonitrile and propionitrile. The reaction temperature can vary within wide limits. It typically lies in the range of room temperature and the boiling point of the reaction mixture.

Preferable solvents for ring opening of the phenoxy-substituted epoxides of formula XI include polyalcohols such as ethyleneglycol, diethyleneglycol and triethyleneglycol, sulfoxides and sulfones such as dimethylsulfoxide and sulfolane as well as other polar solvents. A nucleophiles of special interest in this context is fluoride. Fluoride is typically used in form of potassium hydrogen difluoride ($KHF_2$). The nucleophilicity of the fluoride ion may be enhanced by phase transfer reagents such as quaternary ammonium salts and phosphonium salts as well as complexing agents such as crown ethers. The reaction temperature lies between +100° C. and the boiling point of the reaction mixture.

In general, epoxides of the general formulae VII or VIII are commercially available or may be prepared according to published procedures such as reacting a phenol of the general formula XII with epichlorohydrine.

Many methods to prepare sulfonylation agent of formula II are known. General ways of preparing such compounds are e.g. described in Houben Weyl, Vol. E11, p 1067 ff (1985).

Another synthesis to prepare compounds of formula I is described in Scheme 4.

Scheme 4:

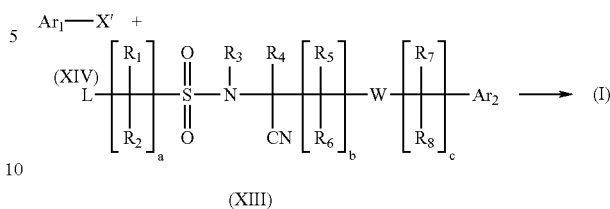

wherein $Ar_1$, $Ar_2$, a, b, c, X', W and $R_1$ to $R_8$ are defined as under formula I.

Compounds of formula XIII wherein $Ar_2$, b, c, W and $R_3$ to $R_8$ are defined as under formula I and L is a leaving group such as e.g. halogen, preferably chlorine, bromine or iodine or a sulfonyloxy group such a e.g. methylsulfonyloxy-, toluylsulfonyloxy- or trifluoromethylsulfonyloxy-group, is coupled with a compound of formula XIV wherein X' is either an anionic radical species of X such as $O^-$, $S^-$, $S(O)_m^-$ combined with an alkaline- or earthalkaline-metal cation as counterion or is defined as X—H such as OH, SH, $NHR_3$. In this case the reaction are generally carried out in the presence of a base such as alkaline-, earthalkaline-carbonates or hydrogencarbonates such e.g. sodium or potassium-carbonate, sodium or potassium-hydrogen-carbonate, cesium-carbonate or an agent capable of scavenging the formed acid.

The starting material of the chemical class of cyanoamines of formula III may also be prepared as described in Scheme 5.

Scheme 5:

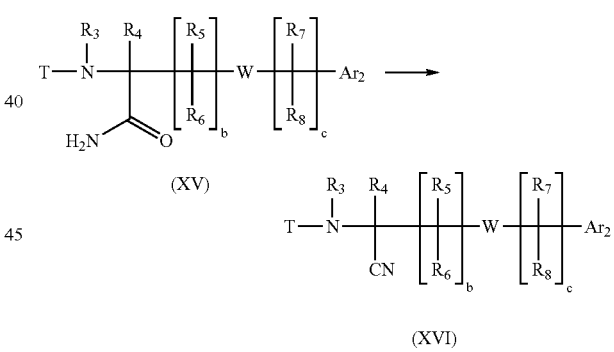

wherein $Ar_1$, $Ar_2$, b, c, W and $R_3$ to $R_8$ are defined as under formula I and symbol T designates a protecting group such as the well-acknowlegded tert-butyloxycarbonyl- or benzyloxycarbonyl-groups, often referred to as (BOC)- or (Z)-groups, and converting the compund of formula XVI into the desired formula III by cleaving the protective group T off.

Many methods are known in the chemical literature e.g. Synthetic Comm., 29 (23), 4235-4239 (1999) or Synthesis (10), 1724-1726 (1999) or Tetrahedron Lett. 29 (18), 2155-2158 (1988) to convert amino acid-amides into aminonitriles. The reaction conditions for the dihydratisation according to Scheme 5 may be adopted from known examples in the art. In another preparatory synthesis pathway compounds of formula XXII, which is a subgroup of formula I, may be obtained according to Scheme 6.

Scheme 6:

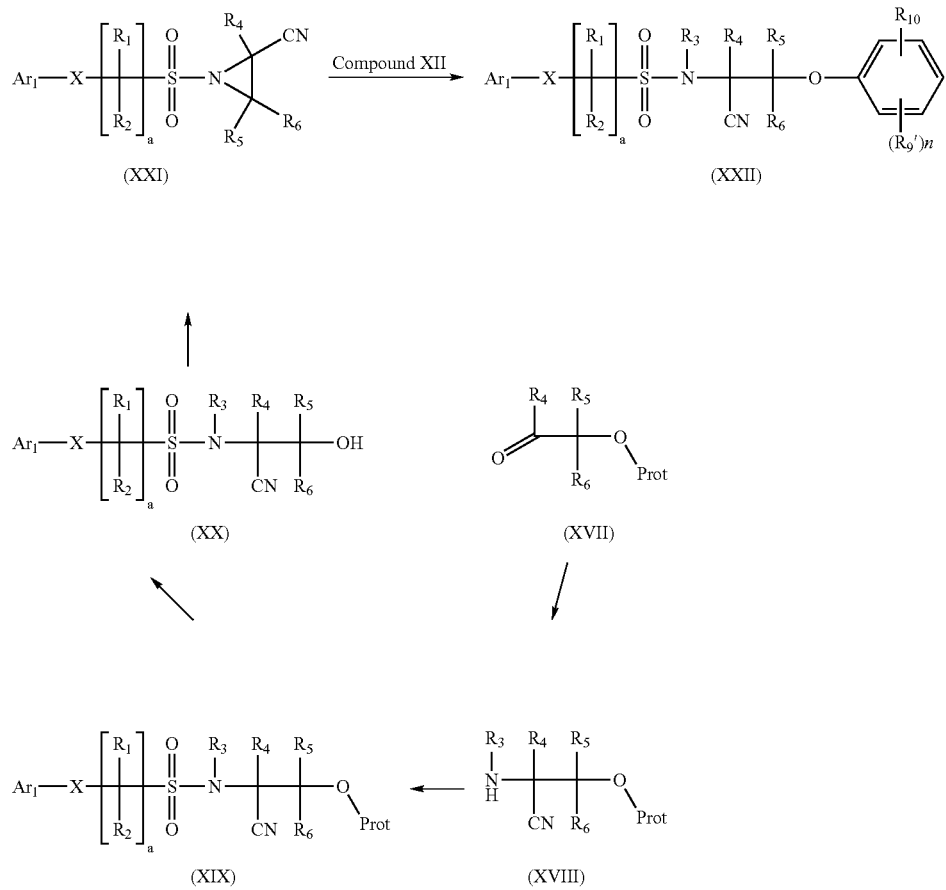

wherein Ar$_1$, R$_1$, R$_2$, R$_4$, R$_5$, R$_8$, R$_9$', R$_{10}$, X, n and a are as defined for formula I, R$_3$ stands for hydrogen and —O-Prot designates an easily cleavable ether group, protecting the hydroxyfunction, like the tetrahydropyranyloxy group.

The reaction pathway of Scheme 6 in the final step shows the ring opening reaction of the aziridine intermediate of formula XXI, which is in analogy to general methods described e.g. Tetrahedron, 52 (40), 13035-13050.

The reaction conditions are as e.g. described in the cited reference, using suitable inert solvents, including ketones, such as acetone and methylethylketoneu halogenated hydrocarbons such as chloroform, carbontetrachloride, dichloromethane, dichloro-ethane, aromatic hydrocarbons such as toluene or xylene, ethers such as t-butyl-methyl-ether, diethylether, tetrahydrofuran and dioxane. The reaction is performed preferentially in the presence of a base. Typical bases include tertiary amines such as trimethylamine, triethylamine, diisopropylethylamine, dimethyl-aniline, diazabi-cyclooctane and N-methylmorpholine, aromatic amines such pyridine and quinoline as well as inorganic bases such as alkaline bicarbonates or -carbonates e.g. example sodium and potassium bicarbonate and sodium, potassium or cesium carbonate.

As also shown in Scheme 6 the aziridines of formula XXI may be prepared by a ring closing reaction, starting from alcohols of formula XX, by employing the so-called Mitsunobu reaction. Intermediate alcohols of formula XX are prepared in several step as outlined. Ketones of formula XVII containing a protected hydroxy function in form of the group —O-Prot (Prot stands for the protective radical that temporarily replaces the H atom during a reaction sequence, but thereafter is reinstalled) desigating an easily cleavable ether group, like the tetrahydropyranyl-oxy group, are reacted as described above in a so-called Strecker-Synthesis. The ether groups, i.e. the tetrahydropyranyl-oxy group are easily prepared and cleaved as described e.g in Biorg. Med. Chem. Lett. 11 (2001), 18, 2541-2543.

Enantiomeric mixtures of formula I may be separated into the enantiomers by chromatography on chiral stationary phase or by classical methodes of fractionated crystallization of diastereomeric salts of a suitable precursor and subsequent conversion into the desired products. Enantiomers or diastereoisomers may also be prepared by enantioselective or diastereoselective synthesis methods.

Alternatively the pure enantiomeric forms of the compounds of formula I may be obtained by the preparation method of Scheme 1 when using enantiomerically pure starting material of formula III*.

The preparation of the enantiomerically pure amines of formula III* may be achieved by sulfonylation as described in Scheme 7.

Scheme 7:

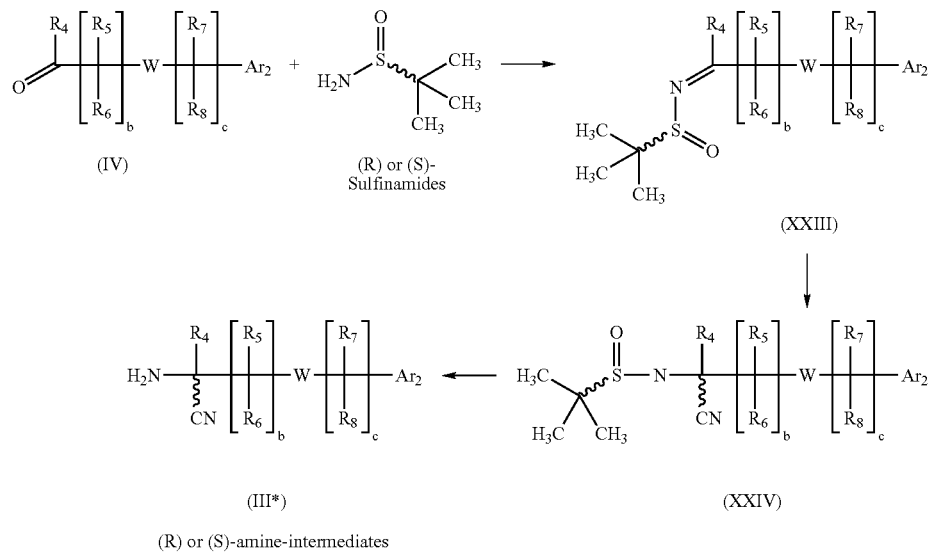

(R) or (S)-amine-intermediates wherein $Ar_2$, $R_4$, $R_5$, $R_6$, $R_7$, $R_8$, W, b and c are as defined for formula I.

In analogy to the methods described in e.g. J. Org. Chem. 1999, 64, 1278-84, ketones of formula (IV) may be treated with sterically fixed chiral sulfinamides, like th shown (R)-(+)-2-methyl-2-propanesulfinamide or (S)-(−)-2-methyl-2-propanesulfinamide to yield the chiral sulfinimides of formula XXIII.

Introducing the cyanide function by the so-called Strecker-type reaction selectively yields the pure diastereoisomers of formula XXIV. Preferably in this reaction step the sulfimides of formula XXIII are treated with a cyanating reagent, for example a di-alkoxy-aluminiumcyanide like di-isopropoxy-aluminiumcyanide, in analogy to methods described in e.g. J. Org. Chem. 2000, 65, 8704-8708. Subsequent cleavage of the sulfinyl group by mineral acids like hydrogen chloride in the last step of the displayed sequence gives the enatomerically pure amines of formula III*.

For this invention it is understood that the preparation method of Scheme 1 encompasses as specific embodiments the preparation of the enantiomerically distinct compounds of formula I which are available when employing the intermediates III* made according to Scheme 7.

The compounds of formula I are oils or solids at room temperature and are distinguished by valuable microbiocidal properties. They can be used in the agricultural sector or related fields preventatively and curatively in the control of plant-destructive microorganisms. The compounds of formula I according to the invention are distinguished at low rates of concentration not only by outstanding microbiocidal, especially fungicidal, activity but also by being especially well tolerated by plants.

Surprisingly, it has now been found that the compounds of formula I have for practical purposes a very advantageous microbiocidal spectrum in the control of phytopathogenic micro-organisms, especially fungi. They possess very advantageous curative and preventive properties and are used in the protection of numerous crop plants. With the compounds of formula I it is possible to inhibit or destroy phytopathogenic microorganisms that occur on various crops of useful plants or on parts of such plants (fruit, blossom, leaves, stems, tubers, roots), while parts of the plants which grow later also remain protected, for example, against phytopathogenic fungi.

The novel compounds of formula I prove to be effective against specific genera of the fungus class Fungi imperfecti (e.g. *Cercospora*), Basidiomycetes (e.g. *Puccinia*) and Ascomycetes (e.g. *Erysiphe* and *Venturia*) and especially against Oomycetes (e.g. *Plasmopara, Peronospora, Pythium* and *Phytophthora*). They therefore represent in plant protection a valuable addition to the compositions for controlling phytopathogenic fungi. The compounds of formula I can also be used as dressings for protecting seed (fruit, tubers, grains) and plant cuttings from fungal infections and against phytopathogenic fungi that occur in the soil.

The invention relates also to compositions comprising compounds of formula I as active ingredient, especially plant-protecting compositions, and to the use thereof in the agricultural sector or related fields.

In addition, the present invention includes the preparation of those compositions, wherein the active ingredient is homogeneously mixed with one or more of the substances or groups of substances described herein. Included is a method of treating plants characterized by the application of the novel compounds of formula I or of the novel compositions.

Target crops to be protected within the scope of this invention comprise, for example, the following species of plants: cereals (wheat, barley, rye, oats, rice, maize, sorghum and related species); beet (sugar beet and fodder beet); pomes, stone fruit and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucurbitaceae (marrows, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocado, cinnamon, camphor) and plants such as tobacco, nuts, coffee, sugar cane, tea, pepper, vines, hops, bananas and natural rubber plants, and also ornamentals.

The compounds of formula I are normally used in the form of compositions and can be applied to the area or plant to be treated simultaneously or in succession with other active ingredients. Those other active ingredients may be fertilisers, micronutrient donors or other preparations that influence plant growth. It is also possible to use selective herbicides or insecticides, fungicides, bactericides, nematicides, molluscicides or mixtures of several of those preparations, if desired together with further carriers, surfactants or other application-promoting adjuvants customarily employed in formulation technology.

The compounds of formula I can be mixed with other fungicides, resulting in some cases in unexpected synergistic enhancement of the biological activities. Such mixtures are not limited to two active ingredients (one of formula I and one of the list of other fungicides), but to the contrary many comprise more than one active ingredient of the component of formula I and more than one other fungicide. Mixing components which are particularly suited for this purpose include e.g. azoles, such as azaconazole, bitertanol, bromuconazole, cyproconazole, difenoconazole, diniconazole, epoxiconazole, fenbuconazole, fluquinconazole, flusilazole, flutriafol, hexaconazole, imazalil, S-imazalil, imibenconazole, ipconazole, metconazole, myclobutanil, oxpoconazole, pefurazoate, penconazole, pyrifenox, prochloraz, propiconazole, prothioconazole, simeconazole, tebuconazole, tetraconazole, triadimefon, triadimenol, triflumizole and triticonazole; pyrimidinyl carbinoles, such as ancymidol, fenarimol and nuarimol; 2-amino-pyrimidines, such as bupirimate, dimethirimol and ethirimol; morpholines, such as dodemorph, fenpropidine, fenpropimorph, spiroxamine and tridemorph; anilinopyrimidines, such as cyprodinil, mepanipyrim and pyrimethanil; pyrroles, such as fenpiclonil and fludioxonil; phenylamides, such as benalaxyl, furalaxyl, metalaxyl, R-metalaxyl, ofurace and oxadixyl; benzimidazoles, such as benomyl, carbendazim, debacarb, fuberidazole and thiabendazole; dicarboximides, such as chlozolinate, dichlozoline, iprodione, myclozoline, procymidone and vinclozoline; carboxamides, such as carboxin, fenfuram, flutolanil, furametpyr, mepronil, oxycarboxin and thifluzamide; guanidines, such as guazatine, dodine and iminoctadine; strobilurines, such as azoxystrobin, dimoxystrobin (SSF-129), fluoxastrobin, kresoxim-methyl, metominostrobin, orysastrobin, picoxystrobin, pyraclostrobin and trifloxystrobin; dithiocarbamates, such as ferbam, mancozeb, maneb, metiram, propineb, thiram, zineb and ziram; N-halomethylthiotetrahydrophthalimides, such as captafol, captan, dichlofluanid, fluoromides, folpet and tolyfluanid; Copper-compounds, such as Bordeaux mixture, copper hydroxide, copper oxychloride, copper sulfate, cuprous oxide, mancopper and oxine-copper; nitrophenol-derivatives, such as dinocap and nitrothalisopropyl; organo-P-derivatives, such as edifenphos, iprobenphos, isoprothiolane, phosdiphen, pyrazophos and toldofos-methyl; various others, such as acibenzolar-S-methyl, anilazine, benthiavalicarb, blasticidin-S, boscalid, chinomethionate, chloroneb, chlorothalonil, IKF-916 (proposed name cyazofamid), cyflufenamid, cymoxanil, dichlone, diclomezine, dicloran, diethofencarb, dimethomorph, ethaboxam, fenoxanil, SYP-L190 (proposed name: flumorph), dithianon, etridiazole, famoxadone, fenamidone, fentin, ferimzone, fluazinam, flusulfamide, fenhexamid, fosetyl-aluminium, hymexazol, iprovalicarb, kasugamycin, methasulfocarb, metrafenone, pencycuron, phthalide, picobenzamid, polyoxins, probenazole, propamocarb, pyroquilon, proquinazid, quinoxyfen, quintozene, silthiofam, sulfur, triazoxide, triadinil, tricyclazole, triforine, validamycin, or zoxamide.

In the above mentioned mixtures, the mixture ratio of the active ingredients is so selected that it reaches optional control of the phytopathogenic microorganism on the host plants. This ratio is in general between 100:1 and 1:100, more preferably between 10:1 and 1:10 of a compound of formula I vis-à-vis the second fungicide. The mixtures may not only comprise one of the listed combinational active ingredients, but may comprise more than one additional active ingredients selected from that specified group, thus forming for example 3-way- or even 4-way-mixtures.

Suitable carriers and surfactants may be solid or liquid and correspond to the substances ordinarily employed in formulation technology, such as e.g. natural or regenerated mineral substances, solvents, dispersants, wetting agents, tackifiers, thickeners, binders or fertilisers. Such carriers and additives are described, for example, in WO 95/30651.

A preferred method of applying a compound of formula I, or an agrochemical composition comprising at least one of those compounds, is application to the foliage (foliar application), the frequency and the rate of application depending upon the risk of infestation by the pathogen in question. The compounds of formula I may also be applied to seed grains (coating) either by impregnating the grains with a liquid formulation of the active ingredient or by coating them with a solid formulation.

The compounds of formula I are used in unmodified form or, preferably, together with the adjuvants conventionally employed in formulation technology, and are for that purpose advantageously formulated in known manner e.g. into emulsifiable concentrates, coatable pastes, directly sprayable or dilutable solutions, dilute emulsions, wettable powders, soluble powders, dusts, granules, and by encapsulation in e.g. polymer substances. As with the nature of the compositions, the methods of application, such as spraying, atomising, dusting, scattering, coating or pouring, are chosen in accordance with the intended objectives and the prevailing circumstances.

Advantageous rates of application are normally from 1 g to 2 kg of active ingredient (a.i.) per hectare (ha), preferably from 10 g to 1 kg a.i/ha, especially from 25 g to 750 g a.i/ha.

When used as seed dressings, rates of from 0.001 g to 5.0 g of active ingredient per kg of seed are advantageously used.

The formulations, i.e. the compositions, preparations or mixtures comprising the compound(s) (active ingredient(s)) of formula I and, where appropriate, a solid or liquid adjuvant, are prepared in known manner, e.g. by homogeneously mixing and/or grinding the active ingredient with extenders, e.g. solvents, solid carriers and, where appropriate, surface-active compounds (surfactants).

Further surfactants customarily used in formulation technology will be known to the person skilled in the art or can be found in the relevant technical literature.

The agrochemical compositions usually comprise 0.01 to 99% by weight, preferably 0.1 to 95% by weight, of a compound of formula I, 99.99 to 1% by weight, preferably 99.9 to 5% by weight, of a solid or liquid adjuvant, and 0 to 25% by weight, preferably 0.1 to 25% by weight, of a surfactant.

Whereas commercial products will preferably be formulated as concentrates, the end user will normally employ dilute formulations.

The compositions may also comprise further ingredients, such as stabilisers, antifoams, viscosity regulators, binders and tackifiers, as well as fertilisers or other active ingredients for obtaining special effects.

The Examples which follow illustrate the invention described above, without limiting the scope thereof in any way. Temperatures are given in degrees Celsius.

PREPARATION EXAMPLES

Example 1

2-(4-Chlorophenoxy-methyl)-2-benzylsulfony-lamino-propionitrile

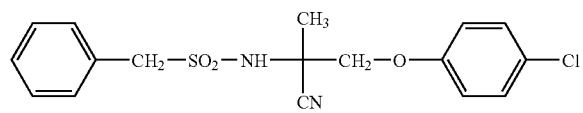

a) 1-(4-Chlorophenoxy)-propan-2-one

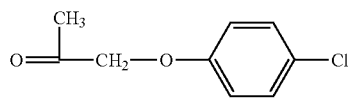

A suspension of 4-chlorophenol (2.6 g, 20 mmol), chloroacetone (2.8 g, 30 mmol) and potassium carbonate (3.45 g, 25 mmol) in acetone (100 ml) is heated at reflux for 3 hours. The precipitating inorganic salts are filtered off and the filtrate is evaporated to dryness to give the 1-(4-chlorophenoxy)-propan-2-one.

b) 2-(4-Chlorophenoxy-methyl)-2-amino-propionitrile

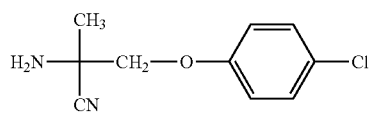

suspension of 1-(4-chloro-phenoxy)-propan-2-one (3.7 g, 20 mmol), ammonium chloride (1.6 g, 29.2 mmol) and sodium cyanide (1.15 g, 23.3 mmol) in a solution of aqueous ammonia (100 ml, 28%) is stirred vigorously at room temperature for 20 hours. The aqueous phase is extracted repeatedly with ethyl acetate. The collected organic extracts are dried and the solvent is evaporated under reduced pressure to give the 2-(4-chlorophenoxy-methyl)-2-amino-propionitrile as a solid.

c) A solution of 2-(4-chlorophenoxy-methyl)-2-amino-propionitrile (0.5 g, 2.4 mmol) and benzylsulfonyl chloride (0.5 g, 2.6 mmol) in pyridine (5 ml) is heated at +80° C. with stirring in the presence of DMAP (0.02 g) for about 16 hours. The reaction mixture is diluted with ethyl acetate and washed with brine. The organic phase is dried over magnesium sulfate and the product is purified by flash chromatography (eluent: ethyl acetate/hexanes 1:3) to give the 2-(4-chlorophenoxy-methyl)-2-benzylsulfonylamino-propionitrile in form of a colorless solid, m.p. 120-121° C.

Example 1b 2-(4-Chlorophenoxy-methyl)-2-benzylsulfony-lamino-propionitrile a) 1-(Tetrahydro-pyran-2-yloxy)-propan-2-one

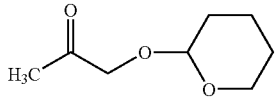

A solution of 1-hydroxy-propan-2-one (95%, 78 g, 1.0 mol), 3,4-dihydro-2H-pyrane (95%, 88.5 g, 1.0 mol) and pyridinium p-toluenesulfonate (25.1 g, 0.1 mol) in THF (1.2 l) is stirred at room temperature for 16 hours. The mixture is diluted with ethyl acetate and repeatedly washed with brine. The organic phase is dried, filtered evaporated to afford 1-(tetrahydropyran-2-yloxy)-propan-2-one (127.8 g, 80.8%) as a liquid.

b) 2-Amino-2-methyl-3-(tetrahydro-pyran-2-yloxy)-propionitrile

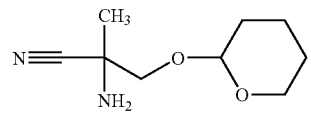

A solution of 1-(tetrahydro-pyran-2-yloxy)-propan-2-one (126.6 g, 0.8 mol), ammonium chloride (65.8 g, 1.23 mol) and sodium cyanide (45.5 g, 0.92 mol) in a solution of aqueous ammonia (920 ml, 28%) is stirred vigorously at room temperature for 5 hours. The aqueous phase is extracted repeatedly with ethyl acetate. The collected organic extracts are dried and the solvent is evaporated under reduced pressure to give the 2-amino-2-methyl-3-(tetrahydro-pyran-2-yloxy)-propionitrile (130 g, 88.2%) as a liquid.

c) N-[1-Cyano-1-methyl-2-(tetrahydro-pyran-2-yloxy)-ethyl]-C-benzylsulfonamide

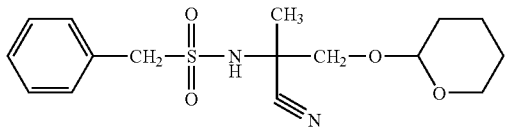

A suspension of 2-Amino-2-methyl)-3-(tetrahydro-pyran-2-yloxy)-propionitrile (74.7 g, 0.405 mol), benzylsulfonyl chloride (90 g, 0.473 mol) and diazabicyclooctane (90.9 g, 0.81 mol) in THF (1.3 l) is stirred at room temperature for about 15 hours. The reaction mixture is diluted with ethyl acetate and washed with brine. The organic phase is dried over magnesium sulfate, the solvent is evaporated under reduced pressure to give the N-[1-cyano-1-methyl-2-(tetrahydro-pyran-2-yloxy)-ethyl]-C-benzylsulfonamide (137 g 100%) as a resin.

d) N-(1-Cyano-2-hydroxy-1-methyl-ethyl)-C-benzylsulfonamide

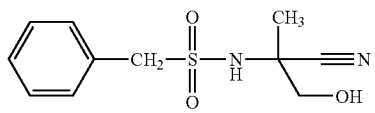

A solution of N-[1-cyano-1-methyl-2-(tetrahydro-pyran-2-yloxy)-ethyl]-C-benzylsulfonamide (135.4 g, 0.4 mol) and pyridinium p-toluenesulfonate (13 g, 0.05 mol) in ethanole (0.5 l) is stirred at 60° C. for 4 hours. The solvent is evaporated under reduced pressure. The residue is then poured onto water (0.5 l). The solid was collected by filtration, washed several times with water (0.6 l), an then dried in a vacuum to yield N-(1-cyano-2-hydroxy-1-methyl-ethyl)-C-phenyl-methanesulfonamide (74.2 g, 72.9%) as an white solid, m.p. 153-155° C.

$^1$HNMR(CDCl$_3$) δJ(Hz): 173(s, 3H, CH$_3$), 3.62-3.66(d, 1H, CH), 3.92-3.96(d, 1H, CH), 4.65(s, 2H, CH$_2$), 6.00(s, 1H, OH), 7.59(s, 5H, Ar—H), 8.03(s, 1H, NH). MS(ES$^-$) m/z 253 (M–H)$^-$.

e) 2-Methyl-1-benzylsulfonyl-aziridine-2-carbonitrile

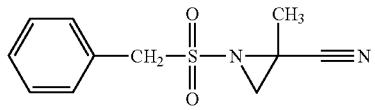

Diethyl azodicarboxylate (0.91 ml, 5.85 mmol) was added dropwise below 10° C. to a mixture of N-(1-cyano-2-hydroxy-1-methyl-ethyl)-C-benzylsulfonamide (1.1.4 g, 4.5 mmol) and Triphenylphosphine (1.53 g, 5.8 mmol) in THF (25 ml). The mixture is stirred at room temperature for 2 hours. The solvent was evaporated and the residue is purified by flash chromatography (eluent: ethyl acetate/hexanes 2:3) to yield 2-methyl-1-benzylsulfonyl-aziridine-2-carbonitrile (1.03 g, 96.8%) as a colorless solid.

$^1$HNMR(CDCl$_3$)δJ(Hz) 1.65(s, 3H, CH$_3$), 2.35(s, 1H, CH), 2.69(1, 1H, CH), 4.57(s, 2H, CH$_2$), 7.43(s, 5H, Ar—H).

f) Cesiumcarbonate (390 mg, 1.2 mmol) was added to a solution of 2-methyl-1-benzylsulfonyl-aziridine-2-carbonitrile (236 mg, 1.0 mmol) in dichloromethane (4 ml) at room temperature with stirring for 5 hours. The reaction mixture was diluted with ethyl acetate and washed with brine. The organic phase is dried over magnesium sulfate and the product is purified by flash chromatography (eluent: ethyl acetate/hexanes 2:3) to give the 2-(4-chlorophenoxy-methyl)-2-benzylsulfonylamino-propionitrile (180 mg, 49.3%) in form of a colorless solid, m.p. 120-121° C.

Example 2

2-(4-Chlorophenoxy-methyl)-2-benzylsulfonylamino-butyronitrile

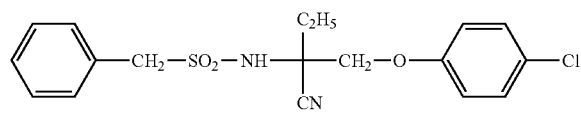

a) 1-(4-Chlorophenoxy)-butane-2-ol

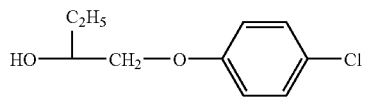

A suspension of chlorophenol (9.0 g, 0.07 mol) and butyleneoxide (6.9 ml, 0.08 mmol) in toluene (80 ml) is heated at reflux with stirring in the presence of a catalytic amount of cesium fluoride (1.5 g) for 20 hours. The reaction mixture is washed with an aqueous solution of sodium hydroxide and dried. The volatiles are evaporated under reduced pressure to give the 1-(4-chloro-phenoxy)-butane-2-ol as a colorless solid.

b) 1-(4-Chlorophenoxy)-butan-2-one

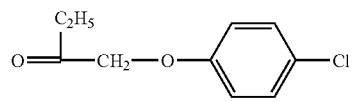

Oxalylchloride (1.0 ml, 0.011 mmol) is added to a solution of dimethylsulfoxide (DMSO) (1.7 ml, 0.022 mol) in methylenechloride (20 ml) at −60° C. 1-(4-Chlorophenoxy)-butan-2-ol (2.0 g, 0.01 mol) is added in one portion. After 15 minutes triethylamine (7 ml, 0.05 mol) is added and the reaction temperature is allowed to warm up and reach 0° C. The mixture is diluted with diethylether and washed repeatedly with brine. The organic phase is dried, filtered evaporated to give the 1-(4-chlorophenoxy)-butane-2-one.

$^1$H-NMR (CDCl$_3$): 7.26 (d, 2H); 6.82 (d, 2H); 4.53 (s, 2H); 2.60 (q, 2H); 1.12 (t, 3H).

c) 2-(Chlorophenoxy)-methyl)-2-amino-butyronitrile

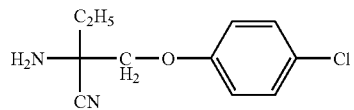

A suspension of 1-(4-chloro-phenoxy)-butan-2-one (3.0 g, 15 mmol), ammonium chloride (1.3 g, 25 mmol) and sodium cyanide (1.0 g, 20 mmol) in a solution of aqueous ammonia (100 ml, 28%) is stirred vigorously at room temperature for 20 hours. The aqueous phase is extracted repeatedly with ethyl acetate. The combined organic phases are dried over sodium sulfate and the solvent is evaporated under reduced pressure to give the 2-(4-chlorophenoxy)-methyl)-2-amino-butyronitrile as an oil having sufficient purity for being directly employable for the following reaction step.

d) A solution of 2-(4-chlorophenoxy)-methyl)-2-amino-butyronitrile (0.5 g, 2.2 mmol), benzylsulfonyl chloride (0.50 g, 2.6 mmol) and diazabicyclooctane (1.0 g, 4 mmol) in anhydrous tetrahydrofuran (20 ml) is stirred for about 16 hours. The reaction mixture is diluted with ethyl acetate and washed with brine. The organic phase is dried over magnesium sulfate and the residue raw product is purified by flash chromatography (eluent: ethyl acetate/hexanes 1:3) to give the 2-(4-chlorophenoxy-methyl)-2-benzylsulfonylamino-butyronitrile in form of a colorless oil. $^1$H-NMR (CDCl$_3$): 7.54-7.50 (m, 2H); 7.46-7.40(m, 3H); 7.30 (d, 2H); 6.84 (d, 2H); 4.70 (s, 1H); 4.49 (s, 2H); 4.22 (dxd, 2H); 2.26-2.04 (m, 2H); 1.12 (t, 3H).

Example 3

2-(4-Chlorophenoxy-methyl)-2-(4-chlorophenyl-methylsulfonyl)-propionitrile

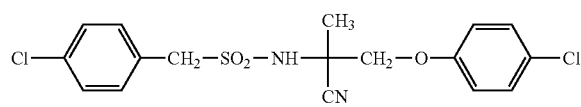

A solution of 2-amino-2-(4-chlorophenoxymethyl)-propionitrile (0.5 g, 0.24 mmol), 4-chlorophenyl-methylsulfonyl chloride (0.46 g, 2.4 mmol) and diazabicyclooctane (0.6 g, 2.4 mmol) in anhydrous tetrahydrofuran (20 ml) is stirred for about 16 hours. The reaction mixture is diluted with ethyl acetate and washed with brine. The organic phase is dried over magnesium sulfate and the raw product received as the residue is purified by flash chromato-graphy (eluent: ethyl acetate/hexanes 1:3) to give the 2-(4-chlorophenoxy-methyl)-2-(4-chlorophenyl-methylsulfonyl)-propionitrile in form of colorless crystals, m.p. 119-120° C.

In analogous manner the compounds of following Table 1 are obtained.

TABLE 1

| No. | $R_1$ | $R_2$ | $R_3$ | $R_4$ | $R_5$ | $R_6$ | $(R_9)_n$ |
|-----|-------|-------|-------|-------|-------|-------|-----------|
| 001 | H | H | H | $CH_3$ | H | H | H |
| 002 | H | H | H | $CH_3$ | H | H | 4-F |
| 003 | $CH_3$ | H | H | $CH_3$ | H | H | H |
| 004 | H | H | H | $CH_2CH_3$ | H | H | H |
| 005 | H | H | H | $CH_2CH_2CH_3$ | H | H | H |
| 006 | H | H | $CH_2$—$OCH_2CH_3$ | $CH_3$ | H | H | H |
| 007 | H | H | $CH_2$—$OCH_2CH_3$ | $CH_2CH_3$ | H | H | H |
| 008 | H | H | H | $CH_3$ | H | H | H |
| 009 | H | H | H | $CH_2CH_3$ | H | H | H |
| 010 | H | H | H | $CH_2(CH_3)_2$ | H | H | H |
| 011 | H | H | H | $CH_2F$ | H | H | H |
| 012 | H | H | $CH_2$—$OCH_2CH_3$ | $CH_3$ | H | H | H |
| 013 | H | H | $CH_2$—$OCH_2CH_3$ | $CH_2CH_3$ | H | H | H |
| 014 | H | H | H | $CH_3$ | H | H | H |
| 015 | H | H | H | $CH_2CH_3$ | H | H | H |
| 016 | H | H | H | $CH_2(CH_3)_2$ | H | H | H |
| 017 | H | H | H | $CH_2F$ | H | H | H |
| 018 | H | H | $CH_2$—$OCH_2CH_3$ | $CH_3$ | H | H | H |
| 019 | H | H | $CH_2$—$OCH_2CH_3$ | $CH_2CH_3$ | H | H | H |
| 020 | H | H | H | $CH_3$ | H | H | H |
| 021 | H | H | H | $CH_2CH_3$ | H | H | H |
| 022 | H | H | H | $CH_2(CH_3)_2$ | H | H | H |
| 023 | H | H | H | $CH_2F$ | H | H | H |
| 024 | H | H | H | $CH_2CH_3$ | H | H | $CH_3$ |
| 025 | H | H | H | $CH_2CH_3$ | H | H | H |
| 026 | H | H | $CH_2$—$OCH_2CH_3$ | $CH_3$ | H | H | 4-F |
| 027 | H | H | $CH_2$—$OCH_2CH_3$ | $CH_2CH_3$ | H | H | H |
| 028 | H | H | H | $CH_3$ | H | H | H |
| 029 | H | H | H | $CH_3$ | H | H | 4-F |
| 030 | $CH_3$ | H | H | $CH_3$ | H | H | H |
| 031 | H | H | H | $CH_2CH_3$ | H | H | H |
| 032 | H | H | H | $CH_2CH_2CH_3$ | H | H | H |
| 033 | $CH_3$ | $CH_3$ | H | $CH_3$ | H | H | H |
| 034 | H | H | H | $CH_3$ | H | H | H |
| 035 | H | H | H | $CH_3$ | H | H | 4-F |
| 036 | $CH_3$ | H | H | $CH_3$ | H | H | H |
| 037 | H | H | H | $CH_2CH_3$ | H | H | H |
| 038 | H | H | H | $CH_2CH_2CH_3$ | H | H | H |
| 039 | $CH_3$ | $CH_3$ | H | $CH_3$ | H | H | H |
| 040 | H | H | H | $CH_3$ | H | H | H |
| 041 | H | H | H | $CH_3$ | H | H | 2-$CH_3$ |
| 042 | H | H | $CH_2$—$OCH_2CH_3$ | $CH_3$ | H | H | H |
| 043 | H | H | $CH_2$—$OCH_2CH_3$ | $CH_2CH_3$ | H | H | H |
| 044 | H | H | H | $CH_3$ | H | H | 2-Cl |
| 045 | H | H | H | $CH_3$ | H | H | 4-F |
| 046 | H | H | H | $CH_3$ | H | H | 4-$SO_2CH_3$ |
| 047 | H | H | H | $CH_3$ | H | H | 3-Cl |
| 048 | H | H | H | $CH_3$ | H | H | 2-$CF_3$ |
| 049 | H | H | H | $CH_3$ | H | H | 2,6-$Cl_2$ |
| 050 | H | H | H | $CH_3$ | H | H | 2-F |
| 051 | H | H | H | $CH_3$ | H | H | 4-Cl |
| 052 | H | H | H | $CH_2CH_3$ | H | H | H |
| 053 | H | H | $CH_3$ | $CH_3$ | H | H | H |

TABLE 1-continued

| | | | | | | | |
|---|---|---|---|---|---|---|---|
| 054 | H | H | H | CH$_2$OC—(CH$_3$)$_3$ | H | H | H |
| 055 | H | H | H | CH$_2$OCH$_2$CH—(CH$_3$)$_2$ | H | H | H |
| 056 | H | H | H | CH$_2$OCH$_2$CH=CH$_2$ | H | H | H |
| 057 | H | H | H | CH$_2$OCH$_3$ | H | H | H |
| 058 | H | H | H | (CH$_2$)2CH$_3$ | H | H | H |
| 059 | H | H | H | CH$_2$F | H | H | H |
| 060 | H | H | H | H | H | H | H |
| 061 | H | H | H | CH(CH$_3$)$_2$ | H | H | H |
| 062 | H | H | H | C(CH$_3$)$_3$ | H | H | H |
| 063 | H | H | H | CH$_2$CH$_3$ | CH$_3$ | H | H |
| 064 | H | H | H | CH$_2$CH$_3$ | CH$_3$ | CH$_3$ | H |
| 065 | H | H | H | CH$_3$ | CH$_3$ | H | H |
| 066 | H | H | H | CH$_2$CH$_3$ | CH$_3$ | CH$_2$CH$_3$ | H |
| 067 | H | H | H | CH$_3$ | CH$_3$ | CH$_3$ | H |
| 068 | H | H | H | CH$_3$ | H | H | H |
| 069 | H | H | H | CH$_3$ | H | H | H |
| 070 | H | H | H | CH$_2$CH$_3$ | H | H | H |
| 071 | H | H | H | CH$_3$ | H | H | H |
| 072 | H | H | H | CH$_3$ | H | H | 4-F |
| 073 | CH$_3$ | H | H | CH$_3$ | H | H | H |
| 074 | H | H | H | CH$_2$CH$_3$ | H | H | H |
| 075 | H | H | H | CH$_2$CH$_2$CH$_3$ | H | H | H |
| 076 | H | H | H | CH$_2$CH$_3$ | CH$_3$ | H | H |
| 077 | H | H | H | CH$_2$CH$_3$ | CH$_3$ | CH$_3$ | H |
| 078 | CH$_3$ | H | H | CH$_2$CH$_3$ | H | H | H |
| 079 | H | H | H | CH$_3$ | H | H | H |
| 080 | H | H | H | CH$_3$ | H | H | H |
| 081 | H | H | H | CH$_3$ | H | H | H |
| 082 | H | H | H | CH$_3$ | H | H | 4-F |
| 083 | CH$_3$ | H | H | CH$_3$ | H | H | H |
| 084 | H | H | H | CH$_2$CH$_3$ | H | H | H |
| 085 | H | H | H | CH$_2$CH$_2$CH$_3$ | H | H | H |
| 086 | H | H | H | CH$_2$CH$_3$ | CH$_3$ | H | H |
| 087 | H | H | H | CH$_2$CH$_3$ | CH$_3$ | CH$_3$ | H |
| 088 | CH$_3$ | CH$_3$ | H | CH$_3$ | CH$_3$ | CH$_3$ | H |
| 089 | H | H | H | CH$_3$ | H | H | H |
| 090 | H | H | H | CH$_3$ | H | H | H |
| 091 | H | H | H | CH$_3$ | H | H | H |
| 092 | H | H | H | CH$_3$ | H | H | H |
| 093 | H | H | H | CH$_3$ | H | H | H |
| 094 | H | H | H | CH$_3$ | H | H | 4-F |
| 095 | CH$_3$ | H | H | CH$_3$ | H | H | H |
| 096 | H | H | H | CH$_2$CH$_3$ | H | H | H |
| 097 | H | H | H | CH$_2$CH$_2$CH$_3$ | H | H | H |
| 098 | H | H | H | CH$_2$CH$_3$ | CH$_3$ | H | H |
| 099 | H | H | H | CH$_3$ | H | H | H |
| 100 | H | H | H | CH$_3$ | H | H | H |
| 101 | H | H | H | CH$_3$ | H | H | H |
| 102 | H | H | H | CH$_3$ | H | H | H |
| 103 | H | H | H | CH$_3$ | CH$_3$ | CH$_3$ | H |
| 104 | H | H | H | CH$_3$ | H | H | H |
| 105 | H | H | H | CH$_2$CH$_3$ | H | H | H |
| 106 | H | H | CH$_2$—OCH$_2$CH$_3$ | CH$_3$ | H | H | H |
| 107 | H | H | CH$_2$—OCH$_2$CH$_3$ | CH$_2$CH$_3$ | H | H | H |
| 108 | H | H | H | CH$_2$CH$_3$ | H | H | 4-F |
| 109 | H | H | H | CH$_3$ | H | H | 4-F |
| 110 | CH$_3$ | H | H | CH$_2$CH$_3$ | H | H | 4-F |
| 111 | CH$_3$ | H | H | CH$_3$ | H | H | 4-F |
| 112 | CH$_3$ | H | H | CH$_2$CH$_3$ | H | H | H |
| 113 | CH$_3$ | H | H | CH$_3$ | H | H | H |
| 114 | CH$_3$ | H | H | CH$_2$CH$_3$ | H | H | H |
| 115 | CH$_3$ | H | H | CH$_3$ | H | H | H |
| 116 | CH$_3$ | CH$_3$ | H | CH$_2$CH$_3$ | CH$_3$ | H | H |
| 117 | CH$_3$ | CH$_3$ | H | CH$_3$ | CH$_3$ | H | H |
| 118 | H | H | H | CH$_2$CH$_3$ | H | H | 4-Cl |
| 119 | H | H | H | CH$_3$ | H | H | 4-Cl |
| 120 | H | H | H | CH$_2$CH$_3$ | H | H | 2-F |
| 121 | H | H | H | CH$_3$ | H | H | 2-F |
| 122 | H | H | H | CH$_2$CH$_3$ | H | H | 2,4-F$_2$ |
| 123 | H | H | H | CH$_3$ | H | H | 2,4-F$_2$ |
| 124 | H | H | H | CH$_2$CH$_3$ | H | H | 2,4-Cl$_2$ |
| 125 | H | H | H | CH$_3$ | H | H | 2,4-Cl$_2$ |
| 126 | H | H | H | CH$_2$CH$_3$ | H | H | 3,4-F$_2$ |
| 127 | H | H | H | CH$_3$ | H | H | 3,4-F$_2$ |
| 128 | H | H | H | CH$_2$CH$_3$ | H | H | 3,4-Cl$_2$ |
| 129 | H | H | H | CH$_3$ | H | H | 3,4-Cl$_2$ |
| 130 | H | H | H | CH$_2$CH$_3$ | H | H | 4-CH$_3$ |
| 131 | H | H | H | CH$_3$ | H | H | 4-CH$_3$ |
| 132 | H | H | H | CH$_2$CH$_3$ | CH$_3$ | CH$_3$ | H |

TABLE 1-continued

| | | | | | | | |
|---|---|---|---|---|---|---|---|
| 133 | H | H | H | CH$_3$ | CH$_3$ | CH$_3$ | H |
| 134 | H | H | H | CH$_2$CH$_3$ | CH$_3$ | CH$_2$CH$_3$ | H |
| 135 | H | H | H | CH$_2$CH$_3$ | H | H | H |
| 136 | H | H | H | CH$_2$CH$_3$ | H | H | H |
| 137 | H | H | H | CH$_2$CH$_3$ | H | H | H |
| 138 | H | H | H | CH$_2$CH$_3$ | H | H | H |
| 139 | H | H | H | CH$_3$ | H | H | H |
| 140 | H | H | H | CH$_3$ | H | H | H |
| 141 | H | H | H | CH$_3$ | H | H | H |
| 142 | H | H | H | CH$_3$ | H | H | H |
| 143 | H | H | H | CH$_2$CH$_3$ | CH$_2$CH$_3$ | CH$_2$CH$_3$ | H |
| 144 | H | H | H | CH$_3$ | H | H | H |
| 145 | H | H | CH$_2$—OCH$_2$CH$_3$ | CH$_3$ | H | H | H |
| 146 | H | H | CH$_2$—OCH$_2$CH$_3$ | CH$_2$CH$_3$ | H | H | H |
| 147 | H | H | H | CH$_3$ | H | H | 4-F |
| 148 | CH$_3$ | H | H | CH$_3$ | H | H | H |
| 149 | H | H | H | CH$_2$CH$_3$ | H | H | H |
| 150 | H | H | H | CH$_2$CH$_2$CH$_3$ | H | H | H |
| 151 | H | H | H | CH$_2$CH$_3$ | CH$_3$ | CH$_2$CH$_3$ | H |
| 152 | H | H | H | CH$_2$CH$_3$ | CH$_3$ | H | H |
| 153 | H | H | H | CH$_2$CH$_3$ | CH$_3$ | CH$_3$ | H |
| 154 | H | H | H | CH$_2$CH$_3$ | H | H | H |
| 155 | H | h | H | CH$_3$ | H | H | H |
| 156 | H | H | H | CH$_2$CH$_3$ | H | H | |
| 157 | H | H | H | CH$_3$ | H | H | H |
| 158 | H | H | CH$_2$—OCH$_2$CH$_3$ | CH$_3$ | H | H | H |
| 159 | H | H | CH$_2$—OCH$_2$CH$_3$ | CH$_2$CH$_3$ | H | H | H |
| 160 | H | H | H | CH$_2$CH$_3$ | H | H | 4-F |
| 161 | H | H | H | CH$_3$ | H | H | 4-F |
| 162 | CH$_3$ | H | H | CH$_3$ | H | H | H |
| 163 | CH$_3$ | H | H | CH$_2$CH$_3$ | H | H | H |
| 164 | H | H | H | CH$_2$CH$_3$ | H | H | 4-Cl |
| 165 | H | H | H | CH$_3$ | H | H | 4-Cl |
| 166 | H | H | H | CH$_2$CH$_3$ | H | H | 2-F |
| 167 | H | H | H | CH$_3$ | H | H | 2-F |
| 168 | H | H | H | CH$_2$CH$_3$ | H | H | 2,4-F$_2$ |
| 169 | H | H | H | CH$_3$ | H | H | 2,4-F$_2$ |
| 170 | H | H | H | CH$_2$CH$_3$ | H | H | 4-CH$_3$ |
| 171 | H | H | H | CH$_3$ | H | H | 4-CH$_3$ |
| 172 | H | H | H | CH$_2$CH$_3$ | H | H | H |
| 173 | H | H | H | CH$_2$CH$_3$ | H | H | H |
| 174 | H | H | H | CH$_2$CH$_3$ | H | H | H |
| 175 | H | H | H | CH$_2$CH$_3$ | H | H | H |
| 176 | H | H | H | CH$_3$ | H | H | H |
| 177 | H | H | H | CH$_3$ | H | H | H |
| 178 | H | H | H | CH$_3$ | H | H | H |
| 179 | H | H | H | CH$_3$ | H | H | H |
| 180 | H | H | H | (CH$_2$)$_2$CH$_3$ | H | H | H |
| 181 | H | H | H | CH$_2$(CH$_3$)$_2$ | H | H | H |
| 182 | H | H | H | CH$_2$CH$_3$ | CH$_3$ | CH$_2$CH$_3$ | H |
| 183 | H | H | H | CH$_2$CH$_3$ | CH$_3$ | H | H |
| 184 | H | H | H | CH$_2$CH$_3$ | CH$_3$ | CH$_3$ | H |
| 185 | CH$_3$ | CH$_3$ | H | CH$_2$CH$_3$ | H | H | H |
| 186 | H | H | H | CH$_3$ | H | H | H |
| 187 | H | H | H | CH$_3$ | H | H | H |
| 188 | H | H | H | CH$_3$ | H | H | H |
| 189 | H | H | H | CH$_2$CH$_3$ | H | H | H |
| 190 | H | H | H | CH$_3$ | H | H | H |
| 191 | H | H | H | CH$_3$ | H | H | 4-F |
| 192 | CH$_3$ | H | H | CH$_3$ | H | H | H |
| 193 | H | H | H | CH$_2$CH$_3$ | H | H | H |
| 194 | H | H | H | CH$_2$CH$_2$CH$_3$ | H | H | H |
| 195 | H | H | H | CH$_2$CH$_3$ | CH$_3$ | H | H |
| 196 | CH$_3$ | CH$_3$ | H | CH$_3$ | H | H | H |
| 197 | H | H | H | CH$_3$ | H | H | H |
| 198 | H | H | H | CH$_3$ | H | H | H |
| 199 | H | H | H | CH$_3$ | H | H | H |
| 200 | H | H | H | CH$_2$CH$_3$ | H | H | H |
| 201 | H | H | H | CH$_3$ | H | H | H |
| 202 | H | H | H | CH$_3$ | H | H | 4-F |
| 203 | CH$_3$ | H | H | CH$_3$ | H | H | H |
| 204 | H | H | H | CH$_2$CH$_3$ | H | H | H |
| 205 | H | H | H | CH$_2$CH$_2$CH$_3$ | H | H | H |
| 206 | H | H | H | CH$_2$CH$_3$ | CH$_3$ | H | H |
| 207 | H | H | H | CH$_3$ | CH$_3$ | H | H |
| 208 | H | H | H | CH$_3$ | H | H | H |
| 209 | H | H | H | CH$_3$ | H | H | H |
| 210 | H | H | H | CH$_3$ | H | H | H |
| 211 | H | H | H | CH$_3$ | H | H | H |

TABLE 1-continued

| | | | | | | | |
|---|---|---|---|---|---|---|---|
| 212 | H | H | H | CH₃ | H | H | 4-F |
| 213 | CH₃ | H | H | CH₃ | H | H | H |
| 214 | H | H | H | CH₂CH₃ | H | H | H |
| 215 | H | H | H | CH₂CH₂CH₃ | H | H | H |
| 216 | H | H | H | CH₂CH₃ | CH₃ | CH₂CH₃ | H |
| 217 | H | H | H | CH₂CH₃ | CH₃ | H | H |
| 218 | H | H | H | CH₂CH₃ | CH₃ | CH₃ | H |
| 219 | H | H | H | CH₃ | H | H | 4-Cl |
| 220 | H | H | H | CH₃ | H | H | H |
| 221 | H | H | H | CH₃ | H | H | 4-F |
| 222 | CH₃ | H | H | CH₃ | H | H | H |
| 223 | H | H | H | CH₂CH₃ | H | H | H |
| 224 | H | H | H | CH₂CH₂CH₃ | H | H | H |
| 225 | H | H | H | CH₂CH₃ | CH₃ | H | H |
| 226 | H | H | H | CH₃ | H | H | H |
| 227 | H | H | H | CH₃ | H | H | H |
| 228 | H | H | H | CH₂CH₃ | H | H | H |
| 229 | H | H | H | CH₃ | H | H | H |
| 230 | H | H | CH₂—OCH₂CH₃ | CH₃ | H | H | H |
| 231 | H | H | CH₂—OCH₂CH₃ | CH₂CH₃ | H | H | H |
| 232 | H | H | H | CH₂CH₃ | H | H | 4-F |
| 233 | H | H | H | CH₃ | H | H | 4-F |
| 234 | CH₃ | H | H | CH₂CH₃ | H | H | 4-F |
| 235 | CH₃ | H | H | CH₃ | H | H | 4-F |
| 236 | CH₃ | H | H | CH₂CH₃ | H | H | H |
| 237 | CH₃ | H | H | CH₃ | H | H | H |
| 238 | CH₃ | H | H | CH₂CH₃ | H | H | H |
| 239 | CH₃ | H | H | CH₃ | H | H | H |
| 240 | CH₃ | CH₃ | H | CH₂CH₃ | CH₃ | H | H |
| 241 | CH₃ | CH₃ | H | CH₃ | CH₃ | H | H |
| 242 | H | H | H | CH₂CH₃ | H | H | 4-Cl |
| 243 | H | H | H | CH₃ | H | H | 4-Cl |
| 244 | H | H | H | CH₂CH₃ | H | H | 2-F |
| 245 | H | H | H | CH₃ | H | H | 2-F |
| 246 | H | H | H | CH₂CH₃ | H | H | 2,4-F₂ |
| 247 | H | H | H | CH₃ | H | H | 2,4-F₂ |
| 248 | H | H | H | CH₂CH₃ | H | H | 2,4-Cl₂ |
| 249 | H | H | H | CH₃ | H | H | 2,4-Cl₂ |
| 250 | H | H | H | CH₂CH₃ | H | H | 3,4-F₂ |
| 251 | H | H | H | CH₃ | H | H | 3,4-F₂ |
| 252 | H | H | H | CH₂CH₃ | H | H | 3,4-Cl₂ |
| 253 | H | H | H | CH₃ | H | H | 3,4-Cl₂ |
| 254 | H | H | H | CH₂CH₃ | H | H | 4-CH₃ |
| 255 | H | H | H | CH₃ | H | H | 4-CH₃ |
| 256 | H | H | H | CH₂CH₃ | CH₃ | CH₃ | H |
| 257 | H | H | H | CH₃ | CH₃ | CH₃ | H |
| 258 | H | H | H | CH₂CH₃ | CH₃; | CH₂CH₃ | H |
| 259 | H | H | H | CH₂CH₃ | H | H | H |
| 260 | H | H | H | CH₂CH₃ | H | H | H |
| 261 | H | H | H | CH₂CH₃ | H | H | H |
| 262 | H | H | H | CH₂CH₃ | H | H | H |
| 263 | H | H | H | CH₃ | H | H | H |
| 264 | H | H | H | CH₃ | H | H | H |
| 265 | H | H | H | CH₃ | H | H | H |
| 266 | H | H | H | CH₃ | H | H | H |
| 267 | H | H | H | (CH₂)₂CH₃ | H | H | H |
| 268 | H | H | H | CH₂(CH₃)₂ | H | H | H |
| 269 | H | H | H | CH₂F | H | H | H |
| 270 | H | H | H | CH₃ | H | H | H |
| 271 | H | H | H | CH₃ | H | H | H |
| 273 | H | H | CH₂—OCH₂CH₃ | CH₃ | H | H | H |
| 274 | H | H | CH₂—OCH₂CH₃ | CH₂CH₃ | H | H | H |
| 275 | H | H | H | CH₃ | H | H | 4-F |
| 276 | CH₃ | H | H | CH₃ | H | H | H |
| 277 | H | H | H | CH₂CH₃ | H | H | H |
| 278 | H | H | H | CH₂CH₂CH₃ | H | H | H |
| 279 | H | H | H | CH₂CH₃ | CH₃ | CH₂CH₃ | H |
| 280 | H | H | H | CH₂CH₃ | CH₃ | H | H |
| 281 | H | H | H | CH₂CH₃ | CH₃ | CH₃ | H |
| 282 | H | H | H | CH₃ | H | H | 4-Cl |
| 283 | H | H | H | CH₃ | H | H | H |
| 284 | H | H | H | CH₂CH₃ | H | H | H |
| 285 | H | H | CH₂—OCH₂CH₃ | CH₃ | H | H | H |
| 286 | H | H | CH₂—OCH₂CH₃ | CH₂CH₃ | H | H | H |
| 287 | CH₃ | H | CH₂—OCH₂CH₃ | CH₂CH₃ | H | H | H |
| 288 | H | H | H | CH₂CH₃ | H | H | H |
| 289 | H | H | H | CH₃ | H | H | H |
| 290 | H | H | CH₂—OCH₂CH₃ | CH₃ | H | H | H |
| 291 | H | H | CH₂—OCH₂CH₃ | CH₂CH₃ | H | H | H |

TABLE 1-continued

| # | | | | | | | |
|---|---|---|---|---|---|---|---|
| 292 | H | H | H | CH₂CH₃ | H | H | 4-F |
| 293 | H | H | H | CH₃ | H | H | 4-F |
| 294 | CH₃ | H | H | CH₂CH₃ | H | H | 4-F |
| 295 | CH₃ | H | H | CH₃ | H | H | 4-F |
| 296 | CH₃ | H | H | CH₂CH₃ | H | H | H |
| 297 | CH₃ | H | H | CH₃ | H | H | H |
| 298 | CH₃ | H | H | CH₂CH₃ | H | H | H |
| 299 | CH₃ | H | H | CH₃ | H | H | H |
| 300 | CH₃ | CH₃ | H | CH₂CH₃ | CH₃ | H | H |
| 301 | CH₃ | CH₃ | H | CH₃ | CH₃ | H | H |
| 302 | H | H | H | CH₂CH₃ | H | H | 4-Cl |
| 303 | H | H | H | CH₃ | H | H | 4-Cl |
| 304 | H | H | H | CH₂CH₃ | H | H | 2-F |
| 305 | H | H | H | CH₃ | H | H | 2-F |
| 306 | H | H | H | CH₂CH₃ | H | H | 2,4-F₂ |
| 307 | H | H | H | CH₃ | H | H | 2,4-F₂ |
| 308 | H | H | H | CH₂CH₃ | H | H | 2,4-Cl₂ |
| 309 | H | H | H | CH₃ | H | H | 2,4-Cl₂ |
| 310 | H | H | H | CH₂CH₃ | H | H | 3,4-F₂ |
| 311 | H | H | H | CH₃ | H | H | 3,4-F₂ |
| 312 | H | H | H | CH₂CH₃ | H | H | 3,4-Cl₂ |
| 313 | H | H | H | CH₃ | H | H | 3,4-Cl₂ |
| 314 | H | H | H | CH₂CH₃ | H | H | 4-CH₃ |
| 315 | H | H | H | CH₃ | H | H | 4-CH₃ |
| 316 | H | H | H | CH₂CH₃ | CH₃ | CH₃ | H |
| 317 | H | H | H | CH₃ | CH₃ | CH₃ | H |
| 318 | H | H | H | CH₂CH₃ | CH₃ | CH₂CH₃ | H |
| 319 | H | H | H | CH₂CH₃ | H | H | H |
| 320 | H | H | H | CH₂CH₃ | H | H | H |
| 321 | H | H | H | CH₂CH₃ | H | H | H |
| 322 | H | H | H | CH₂CH₃ | H | H | H |
| 323 | H | H | H | CH₃ | H | H | H |
| 324 | H | H | H | CH₃ | H | H | H |
| 325 | H | H | H | CH₃ | H | H | H |
| 326 | H | H | H | CH₃ | H | H | H |
| 327 | H | H | H | (CH₂)₂CH₃ | H | H | H |
| 328 | H | H | H | CH₂(CH₃)₂ | H | H | H |
| 329 | H | H | H | CH₂F | H | H | H |
| 330 | H | H | H | CH₃ | CH₂CH₃ | CH₂CH₃ | H |
| 331 | H | H | H | CH₂CH₃ | H | H | H |
| 332 | H | H | H | CH₃ | H | H | H |
| 333 | H | H | CH₂—OCH₂CH₃ | CH₃ | H | H | H |
| 334 | H | H | CH₂—OCH₂CH₃ | CH₂CH₃ | H | H | H |
| 335 | H | H | H | CH₂CH₃ | H | H | 4-F |
| 336 | H | H | H | CH₃ | H | H | 4-F |
| 337 | CH₃ | H | H | CH₂CH₃ | H | H | 4-F |
| 338 | CH₃ | H | H | CH₃ | H | H | 4-F |
| 339 | CH₃ | H | H | CH₂CH₃ | H | H | H |
| 340 | CH₃ | H | H | CH₃ | H | H | H |
| 341 | CH₃ | H | H | CH₂CH₃ | H | H | H |
| 342 | CH₃ | H | H | CH₃ | H | H | H |
| 343 | CH₃ | CH₃ | H | CH₂CH₃ | CH₃ | H | H |
| 344 | CH₃ | CH₃ | H | CH₃ | CH₃ | H | H |
| 345 | H | H | H | CH₂CH₃ | H | H | 4-Cl |
| 346 | H | H | H | CH₃ | H | H | 4-Cl |
| 347 | H | H | H | CH₂CH₃ | H | H | 2-F |
| 348 | H | H | H | CH₃ | H | H | 2-F |
| 349 | H | H | H | CH₂CH₃ | H | H | 2,4-F₂ |
| 350 | H | H | H | CH₃ | H | H | 2,4-F₂ |
| 351 | H | H | H | CH₂CH₃ | H | H | 2,4-Cl₂ |
| 352 | H | H | H | CH₃ | H | H | 2,4-Cl₂ |
| 353 | H | H | H | CH₂CH₃ | H | H | 3,4-F₂ |
| 354 | H | H | H | CH₃ | H | H | 3,4-F₂ |
| 355 | H | H | H | CH₂CH₃ | H | H | 3,4-Cl₂ |
| 356 | H | H | H | CH₃ | H | H | 3,4-Cl₂ |
| 357 | H | H | H | CH₂CH₃ | H | H | 4-CH₃ |
| 358 | H | H | H | CH₃ | H | H | 4-CH₃ |
| 359 | H | H | H | CH₂CH₃ | CH₃ | CH₃ | H |
| 360 | H | H | H | CH₃ | CH₃ | CH₃ | H |
| 361 | H | H | H | CH₂CH₃ | CH₃ | CH₂CH₃ | H |
| 362 | H | H | H | CH₂CH₃ | H | H | H |
| 363 | H | H | H | CH₂CH₃ | H | H | H |
| 364 | H | H | H | CH₂CH₃ | H | H | H |
| 365 | H | H | H | CH₂CH₃ | H | H | H |
| 366 | H | H | H | CH₃ | H | H | H |
| 367 | H | H | H | CH₃ | H | H | H |
| 368 | H | H | H | CH₃ | H | H | H |
| 369 | H | H | H | CH₃ | H | H | H |
| 370 | H | H | H | (CH₂)₂CH₃ | H | H | H |

TABLE 1-continued

| | | | | | | | |
|---|---|---|---|---|---|---|---|
| 371 | H | H | H | CH$_2$(CH$_3$)$_2$ | H | H | H |
| 372 | H | H | H | CH$_2$F | H | H | H |
| 373 | H | H | CH$_2$—OCH$_3$ | CH$_3$ | H | H | H |
| 374 | H | H | CH$_2$—OCH$_3$ | CH$_2$CH$_3$ | H | H | H |
| 375 | H | H | H | CH$_3$ | H | H | H |
| 376 | H | H | CH$_2$—OCH$_2$CH$_3$ | CH$_3$ | H | H | H |
| 377 | H | H | CH$_2$—OCH$_2$CH$_3$ | CH$_2$CH$_3$ | H | H | H |
| 378 | H | H | H | CH$_3$ | H | H | H |
| 379 | H | H | H | CH$_2$CH$_3$ | H | H | H |
| 380 | H | H | H | CH$_3$ | H | H | H |
| 381 | H | H | H | CH$_2$CH$_3$ | H | H | H |
| 382 | H | H | H | CH$_3$ | H | H | 4-F |
| 383 | CH$_3$ | H | H | CH$_3$ | H | H | H |
| 384 | H | H | H | CH$_3$ | H | H | H |
| 385 | H | H | H | CH$_2$CH$_2$CH$_3$ | H | H | H |
| 386 | H | H | H | CH$_2$CH$_3$ | CH$_3$ | CH$_2$CH$_3$ | H |
| 387 | H | H | H | CH$_2$CH$_3$ | CH$_3$ | H | H |
| 388 | H | H | H | CH$_2$CH$_3$ | CH$_3$ | CH$_3$ | H |
| 389 | CH$_3$ | H | H | CH$_2$CH$_3$ | CH$_3$ | CH$_3$ | H |
| 390 | H | H | H | CH$_2$CH$_3$ | H | H | H |
| 391 | H | H | H | CH$_2$CH$_3$ | H | H | H |
| 392 | H | H | H | CH$_3$ | H | H | H |
| 393 | H | H | CH$_2$—OCH$_2$CH$_3$ | CH$_3$ | H | H | H |
| 394 | H | H | CH$_2$—OCH$_2$CH$_3$ | CH$_2$CH$_3$ | H | H | H |
| 395 | H | H | H | CH$_2$CH$_3$ | H | H | 4-F |
| 396 | H | H | H | CH$_3$ | H | H | 4-F |
| 397 | CH$_3$ | H | H | CH$_3$ | H | H | H |
| 398 | CH$_3$ | H | H | CH$_2$CH$_3$ | H | H | H |
| 399 | H | H | H | CH$_2$CH$_3$ | H | H | 4-Cl |
| 400 | H | H | H | CH$_3$ | H | H | 4-Cl |
| 401 | H | H | H | CH$_2$CH$_3$ | H | H | 2-F |
| 402 | H | H | H | CH$_3$ | H | H | 2-F |
| 403 | H | H | H | CH$_2$CH$_3$ | H | H | 2,4-F$_2$ |
| 404 | H | H | H | CH$_3$ | H | H | 2,4-F$_2$ |
| 405 | H | H | H | CH$_2$CH$_3$ | H | H | 4-CH$_3$ |
| 406 | H | H | H | CH$_3$ | H | H | 4-CH$_3$ |
| 407 | H | H | H | CH$_2$CH$_3$ | H | H | H |
| 408 | H | H | H | CH$_2$CH$_3$ | H | H | H |
| 409 | H | H | H | CH$_2$CH$_3$ | H | H | H |
| 410 | H | H | H | CH$_2$CH$_3$ | H | H | H |
| 411 | H | H | H | CH$_3$ | H | H | H |
| 412 | H | H | H | CH$_3$ | H | H | H |
| 413 | H | H | H | CH$_3$ | H | H | H |
| 414 | H | H | H | CH$_3$ | H | H | H |
| 415 | H | H | H | (CH$_2$)$_2$CH$_3$ | H | H | H |
| 416 | H | H | H | CH$_2$(CH$_3$)$_2$ | H | H | H |
| 417 | H | H | H | CH$_2$CH$_3$ | CH$_3$ | CH$_2$CH$_3$ | H |
| 418 | H | H | H | CH$_2$CH$_3$ | CH$_3$ | H | H |
| 419 | H | H | H | CH$_2$CH$_3$ | CH$_3$ | CH$_3$ | H |
| 420 | H | H | H | CH$_2$CH$_3$ | CH$_2$CH$_3$ | CH$_2$CH$_3$ | H |
| 421 | H | H | H | CH$_2$CH$_3$ | H | H | H |
| 422 | H | H | H | CH$_3$ | H | H | H |
| 423 | H | H | CH$_2$—OCH$_2$CH$_3$ | CH$_3$ | H | H | H |
| 424 | H | H | CH$_2$—OCH$_2$CH$_3$ | CH$_2$CH$_3$ | H | H | H |
| 425 | H | H | H | CH$_2$CH$_3$ | H | H | 4-F |
| 426 | H | H | H | CH$_3$ | H | H | 4-F |
| 427 | CH$_3$ | H | H | CH$_3$ | H | H | H |
| 428 | CH$_3$ | H | H | CH$_2$CH$_3$ | H | H | H |
| 429 | H | H | H | CH$_2$CH$_3$ | H | H | 4-Cl |
| 430 | H | H | H | CH$_3$ | H | H | 4-Cl |
| 431 | H | H | H | CH$_2$CH$_3$ | H | H | 2-F |
| 432 | H | H | H | CH$_3$ | H | H | 2-F |
| 433 | H | H | H | CH$_2$CH$_3$ | H | H | 2,4-F$_2$ |
| 434 | H | H | H | CH$_3$ | H | H | 2,4-F$_2$ |
| 435 | H | H | H | CH$_2$CH$_3$ | H | H | 4-CH$_3$ |
| 436 | H | H | H | CH$_3$ | H | H | 4-CH$_3$ |
| 437 | H | H | H | CH$_2$CH$_3$ | H | H | H |
| 438 | H | H | H | CH$_2$CH$_3$ | H | H | H |
| 439 | H | H | H | CH$_2$CH$_3$ | H | H | H |
| 440 | H | H | H | CH$_2$CH$_3$ | H | H | H |
| 441 | H | H | H | CH$_3$ | H | H | H |
| 442 | H | H | H | CH$_3$ | H | H | H |
| 443 | H | H | H | CH$_3$ | H | H | H |
| 444 | H | H | H | CH$_3$ | H | H | H |
| 445 | H | H | H | (CH$_2$)$_2$CH$_3$ | H | H | H |
| 446 | H | H | H | CH$_2$(CH$_3$)$_2$ | H | H | H |
| 447 | H | H | H | CH$_2$CH$_3$ | CH$_3$ | CH$_2$CH$_3$ | H |
| 448 | H | H | H | CH$_2$CH$_3$ | CH$_3$ | H | H |
| 449 | H | H | H | CH$_2$CH$_3$ | CH$_3$ | CH$_3$ | H |

TABLE 1-continued

| | | | | | | | |
|---|---|---|---|---|---|---|---|
| 450 | CH₃ | CH₃ | H | CH₂CH₃ | H | H | H |
| 451 | H | H | H | CH₃ | H | H | H |
| 452 | H | H | H | CH₂CH₃ | H | H | H |
| 453 | H | H | H | CH₂CH₃ | H | H | H |
| 454 | H | H | H | CH₂CH₃ | H | H | H |
| 455 | H | H | H | CH₂CH₃ | H | H | H |
| 456 | H | H | H | CH₃ | H | H | H |
| 457 | H | H | H | CH₃ | H | H | H |
| 458 | H | H | CH₃ | CH₃ | H | H | H |
| 459 | H | H | H | CH₃ | H | H | 4-F |
| 460 | CH₃ | H | H | CH₃ | H | H | H |
| 461 | H | H | H | CH₂CH₃ | H | H | H |
| 462 | H | H | H | CH₂CH₂CH₃ | H | H | H |
| 463 | H | H | H | CH₂CH₃ | CH₃ | CH₂CH₃ | H |
| 464 | H | H | H | CH₂CH₃ | CH₃ | H | H |
| 465 | H | H | H | CH₂CH₃ | CH₃ | CH₃ | H |
| 466 | CH₃ | CH₃ | H | CH₂CH₃ | H | H | H |
| 467 | H | H | H | CH₂CH₃ | H | H | H |
| 468 | H | H | H | CH₂CH₃ | H | H | H |
| 469 | H | H | H | CH₂CH₃ | H | H | H |
| 470 | H | H | H | CH₃ | H | H | 4-F |
| 471 | CH₃ | H | H | CH₃ | H | H | H |
| 472 | H | H | H | CH₃ | H | H | H |
| 473 | H | H | H | CH₂CH₂CH₃ | H | H | H |
| 474 | H | H | H | CH₂CH₃ | CH₃ | CH₂CH₃ | H |
| 475 | H | H | H | CH₂CH₃ | CH₃ | H | H |
| 476 | H | H | H | CH₂CH₃ | CH₃ | CH₃ | H |
| 477 | CH₃ | CH₃ | H | CH₃ | H | H | H |
| 478 | H | H | H | CH₂CH₃ | H | H | H |
| 479 | H | H | H | CH₂CH₃ | H | H | H |
| 480 | H | H | H | CH₂CH₃ | H | H | H |
| 481 | H | H | H | CH₃ | H | H | H |
| 482 | H | H | H | CH₃ | H | H | 4-F |
| 483 | CH₃ | H | H | CH₃ | H | H | H |
| 484 | H | H | H | CH₂CH₂CH₃ | H | H | H |
| 485 | H | H | H | CH₂CH₃ | CH₃ | CH₂CH₃ | H |
| 486 | H | H | H | CH₂CH₃ | CH₃ | H | H |
| 487 | H | H | H | CH₂CH₃ | CH₃ | CH₃ | H |
| 488 | CH₃ | H | H | CH₂CH₃ | H | H | H |
| 489 | H | H | H | CH₂CH₃ | H | H | H |
| 490 | H | H | H | CH₃ | H | H | H |
| 491 | H | H | H | CH₃ | H | H | 4-F |
| 492 | CH₃ | H | H | CH₃ | H | H | H |
| 493 | H | H | H | CH(CH₃)₂ | H | H | H |
| 494 | H | H | H | CH₂CH₂CH₃ | H | H | H |
| 495 | H | H | H | CH₂CH₃ | CH₃ | CH₂CH₃ | H |
| 496 | H | H | H | CH₂CH₃ | CH₃ | H | H |
| 497 | H | H | H | CH₂CH₃ | CH₃ | CH₃ | H |
| 498 | H | H | H | CH₂F | H | H | H |
| 499 | H | H | H | CH₂CH₃ | H | H | H |
| 500 | H | H | H | CH₃ | H | H | H |
| 501 | H | H | H | CH₃ | H | H | 4-F |
| 502 | CH₃ | H | H | CH₃ | H | H | H |
| 503 | H | H | H | CH(CH₃)₂ | H | H | H |
| 504 | H | H | H | CH₂CH₂CH₃ | H | H | H |
| 505 | H | H | H | CH₂CH₃ | CH₃ | CH₂CH₃ | H |
| 506 | H | H | H | CH₂CH₃ | CH₃ | H | H |
| 507 | H | H | H | CH₂CH₃ | CH₃ | CH₃ | H |
| 508 | H | H | H | CH₂F | H | H | H |
| 509 | H | H | H | CH₃ | H | H | H |
| 510 | H | H | H | CH₂CH₃ | H | H | H |
| 511 | H | H | H | CH₃ | H | H | H |
| 512 | H | H | H | CH₃ | H | H | H |
| 513 | H | H | H | CH₂CH₃ | H | H | H |
| 514 | H | H | H | CH₂CH₃ | H | H | H |
| 515 | H | H | CH₂—OCH₂CH₃ | CH₃ | H | H | H |
| 516 | H | H | CH₂—OCH₂CH₃ | CH₂CH₃ | H | H | H |
| 517 | H | H | H | CH₃ | H | H | H |
| 518 | H | H | H | CH₂CH₃ | H | H | 4-F |
| 519 | H | H | H | CH₃ | H | H | 4-F |
| 520 | CH₃ | H | H | CH₂CH₃ | H | H | 4-F |
| 521 | CH₃ | H | H | CH₃ | H | H | 4-F |
| 522 | CH₃ | H | H | CH₂CH₃ | H | H | H |
| 523 | CH₃ | H | H | CH₃ | H | H | H |
| 524 | CH₃ | H | H | CH₂CH₃ | H | H | H |
| 525 | CH₃ | H | H | CH₃ | H | H | H |
| 526 | CH₃ | CH₃ | H | CH₂CH₃ | CH₃ | H | H |
| 527 | CH₃ | CH₃ | H | CH₃ | CH₃ | H | H |
| 528 | H | H | H | CH₂CH₃ | H | H | 4-Cl |

TABLE 1-continued

| | | | | | | | |
|---|---|---|---|---|---|---|---|
| 529 | H | H | H | $CH_3$ | H | H | 4-Cl |
| 530 | H | H | H | $CH_2CH_3$ | H | H | 2-F |
| 531 | H | H | H | $CH_3$ | H | H | 2-F |
| 532 | H | H | H | $CH_2CH_3$ | H | H | $2,4-F_2$ |
| 533 | H | H | H | $CH_3$ | H | H | $2,4-F_2$ |
| 534 | H | H | H | $CH_2CH_3$ | H | H | $2,4-Cl_2$ |
| 535 | H | H | H | $CH_3$ | H | H | $2,4-Cl_2$ |
| 536 | H | H | H | $CH_2CH_3$ | H | H | $3,4-F_2$ |
| 537 | H | H | H | $CH_3$ | H | H | $3,4-F_2$ |
| 538 | H | H | H | $CH_2CH_3$ | H | H | $3,4-Cl_2$ |
| 539 | H | H | H | $CH_3$ | H | H | $3,4-Cl_2$ |
| 540 | H | H | H | $CH_2CH_3$ | H | H | $4-CH_3$ |
| 541 | H | H | H | $CH_3$ | H | H | $4-CH_3$ |
| 542 | H | H | H | $CH_2CH_3$ | $CH_3$ | $CH_3$ | H |
| 543 | H | H | H | $CH_3$ | $CH_3$ | $CH_3$ | H |
| 544 | H | H | H | $CH_2CH_3$ | $CH_3$ | $CH_2CH_3$ | H |
| 545 | H | H | H | $CH_2CH_3$ | H | H | H |
| 546 | H | H | H | $CH_2CH_3$ | H | H | H |
| 547 | H | H | H | $CH_2CH_3$ | H | H | H |
| 548 | H | H | H | $CH_2CH_3$ | H | H | H |
| 549 | H | H | H | $CH_3$ | H | H | H |
| 550 | H | H | H | $CH_3$ | H | H | H |
| 551 | H | H | H | $CH_3$ | H | H | H |
| 552 | H | H | H | $CH_3$ | H | H | H |
| 553 | H | H | H | $(CH_2)_2CH_3$ | H | H | H |
| 554 | H | H | H | $CH_2(CH_3)_2$ | H | H | H |
| 555 | H | H | H | $CH_2F$ | H | H | H |
| 556 | H | H | H | $CH_3$ | H | H | H |
| 557 | H | H | H | $CH_2CH_3$ | H | H | H |
| 558 | H | H | H | $CH_2CH_3$ | H | H | H |
| 559 | H | H | H | $CH_3$ | H | H | 4-F |
| 560 | $CH_3$ | H | H | $CH_3$ | H | H | H |
| 561 | H | H | H | $CH_3$ | H | H | H |
| 562 | H | H | H | $CH_2CH_2CH_3$ | H | H | H |
| 563 | H | H | H | $CH_2{}_{CH2}CH_2CH_3$ | H | H | H |
| 564 | H | H | H | $CH_2CH_3$ | H | H | H |
| 565 | H | H | H | $CH_3$ | $CH_3$ | H | H |
| 566 | H | H | $CH_2-OCH_2CH_3$ | $CH_3$ | H | H | H |
| 567 | H | H | $CH_2-OCH_2CH_3$ | $CH_2CH_3$ | H | H | H |
| 568 | H | H | H | $CH_3$ | H | H | H |
| 569 | H | H | H | $CH_2CH_3$ | H | H | 4-F |
| 570 | H | H | H | $CH_3$ | H | H | 4-F |
| 571 | $CH_3$ | H | H | $CH_2CH_3$ | H | H | 4-F |
| 572 | $CH_3$ | H | H | $CH_3$ | H | H | 4-F |
| 573 | $CH_3$ | H | H | $CH_2CH_3$ | H | H | H |
| 574 | $CH_3$ | H | H | $CH_3$ | H | H | H |
| 575 | $CH_3$ | H | H | $CH_2CH_3$ | H | H | H |
| 576 | $CH_3$ | H | H | $CH_3$ | H | H | H |
| 577 | $CH_3$ | $CH_3$ | H | $CH_2CH_3$ | $CH_3$ | H | H |
| 578 | $CH_3$ | $CH_3$ | H | $CH_3$ | $CH_3$ | H | H |
| 579 | H | H | H | $CH_2CH_3$ | H | H | 4-Cl |
| 580 | H | H | H | $CH_3$ | H | H | 4-Cl |
| 581 | H | H | H | $CH_2CH_3$ | H | H | 2-F |
| 582 | H | H | H | $CH_3$ | H | H | 2-F |
| 583 | H | H | H | $CH_2CH_3$ | H | H | $2,4-F_2$ |
| 584 | H | H | H | $CH_3$ | H | H | $2,4-F_2$ |
| 585 | H | H | H | $CH_2CH_3$ | H | H | $2,4-Cl_2$ |
| 586 | H | H | H | $CH_3$ | H | H | $2,4-Cl_2$ |
| 587 | H | H | H | $CH_2CH_3$ | H | H | $3,4-F_2$ |
| 588 | H | H | H | $CH_3$ | H | H | $3,4-F_2$ |
| 589 | H | H | H | $CH_2CH_3$ | H | H | $3,4-Cl_2$ |
| 590 | H | H | H | $CH_3$ | H | H | $3,4-Cl_2$ |
| 591 | H | H | H | $CH_2CH_3$ | H | H | $4-CH_3$ |
| 592 | H | H | H | $CH_3$ | H | H | $4-CH_3$ |
| 593 | H | H | H | $CH_2CH_3$ | $CH_3$ | $CH_3$ | H |
| 594 | H | H | H | $CH_3$ | $CH_3$ | $CH_3$ | H |
| 595 | H | H | H | $CH_2CH_3$ | $CH_3$ | $CH_2CH_3$ | H |
| 596 | H | H | H | $CH_2CH_3$ | H | H | H |
| 597 | H | H | H | $CH_2CH_3$ | H | H | H |
| 598 | H | H | H | $CH_2CH_3$ | H | H | H |
| 599 | H | H | H | $CH_2CH_3$ | H | H | H |
| 600 | H | H | H | $CH_3$ | H | H | H |
| 601 | H | H | H | $CH_3$ | H | H | H |
| 602 | H | H | H | $CH_3$ | H | H | H |
| 603 | H | H | H | $CH_3$ | H | H | H |
| 604 | H | H | H | $(CH_2)_2CH_3$ | H | H | H |
| 605 | H | H | H | $CH_2(CH_3)_2$ | H | H | H |
| 606 | H | H | H | $CH_2F$ | H | H | H |
| 607 | H | H | H | $CH_3$ | H | H | H |

TABLE 1-continued

| | | | | | | | |
|---|---|---|---|---|---|---|---|
| 608 | H | H | CH$_2$—OCH$_2$CH$_3$ | CH$_3$ | H | H | H |
| 609 | H | H | CH$_2$—OCH$_2$CH$_3$ | CH$_2$CH$_3$ | H | H | H |
| 610 | H | H | H | CH$_3$ | H | H | H |
| 611 | H | H | CH$_2$—OCH$_2$CH$_3$ | CH$_3$ | H | H | H |
| 612 | H | H | CH$_2$—OCH$_2$CH$_3$ | CH$_2$CH$_3$ | H | H | H |
| 613 | H | H | H | CH$_3$ | CH$_2$CH$_3$ | CH$_2$CH$_3$ | H |
| 614 | H | H | H | CH$_3$ | H | H | 4-F |
| 615 | CH$_3$ | H | H | CH$_3$ | H | H | H |
| 616 | H | H | H | CH$_3$ | H | H | 4-F |
| 617 | H | H | H | CH$_2$CH$_3$ | H | H | H |
| 618 | H | H | H | CH$_2$CH$_2$CH$_3$ | H | H | H |
| 619 | H | H | H | CH$_2$CH$_3$ | CH$_3$ | H | H |
| 620 | H | H | H | CH$_2$CH$_3$ | CH$_3$ | CH$_3$ | H |
| 621 | H | H | H | CH$_3$ | H | H | 4-F |
| 622 | CH$_3$ | H | H | CH$_3$ | H | H | H |
| 623 | H | H | H | CH$_3$ | H | H | 4-F |
| 624 | H | H | H | CH$_2$CH$_3$ | H | H | H |
| 625 | H | H | H | CH$_2$CH$_2$CH$_3$ | H | H | H |
| 626 | H | H | H | CH$_2$CH$_3$ | CH$_3$ | H | H |
| 627 | H | H | H | CH$_2$CH$_3$ | CH$_3$ | CH$_3$ | H |
| 628 | H | H | H | CH$_3$ | CH$_3$ | H | H |
| 629 | H | H | H | CH$_2$CH$_3$ | CH$_3$ | CH$_2$CH$_3$ | H |
| 630 | H | H | H | CH$_3$ | H | H | 4-F |
| 631 | CH$_3$ | H | H | CH$_3$ | H | H | H |
| 632 | H | H | H | CH$_3$ | H | H | 4-F |
| 633 | H | H | H | CH$_2$CH$_3$ | H | H | H |
| 634 | H | H | H | CH$_2$CH$_2$CH$_3$ | H | H | H |
| 635 | H | H | H | CH$_2$CH$_3$ | CH$_3$ | H | H |
| 636 | H | H | H | CH$_2$CH$_3$ | CH$_3$ | CH$_3$ | H |
| 637 | H | H | H | CH$_3$ | CH$_3$ | H | H |
| 638 | H | H | H | CH$_2$CH$_3$ | CH$_3$; | CH$_2$CH$_3$ | H |
| 639 | H | H | H | CH$_3$ | H | H | 4-F |
| 640 | CH$_3$ | H | H | CH$_3$ | H | H | H |
| 641 | H | H | H | CH$_3$ | H | H | 4-F |
| 642 | H | H | H | CH$_2$CH$_3$ | H | H | H |
| 643 | H | H | H | CH$_2$CH$_2$CH$_3$ | H | H | H |
| 644 | H | H | H | CH$_2$CH$_3$ | CH$_3$ | H | H |
| 645 | H | H | H | CH$_2$CH$_3$ | CH$_3$ | CH$_3$ | H |
| 646 | H | H | H | CH$_3$ | CH$_3$ | H | H |
| 647 | H | H | H | CH$_2$CH$_3$ | CH$_3$ | CH$_2$CH$_3$ | H |
| 648 | H | H | H | CH$_3$ | H | H | 4-F |
| 649 | CH$_3$ | H | H | CH$_3$ | H | H | H |
| 650 | H | H | H | CH$_3$ | H | H | 4-F |
| 651 | H | H | H | CH$_2$CH$_3$ | H | H | H |
| 652 | H | H | H | CH$_2$CH$_2$CH$_3$ | H | H | H |
| 653 | H | H | H | CH$_2$CH$_3$ | CH$_3$ | H | H |
| 654 | H | H | H | CH$_2$CH$_3$ | CH$_3$ | CH$_3$ | H |
| 655 | H | H | H | CH$_3$ | CH$_3$ | H | H |
| 656 | H | H | H | CH$_2$CH$_3$ | CH$_3$ | CH$_2$CH$_3$ | H |
| 657 | H | H | H | CH$_2$CH$_3$ | H | H | H |
| 658 | H | H | H | CH$_3$ | H | H | H |
| 659 | H | H | H | CH$_2$CH$_3$ | H | H | H |
| 660 | H | H | H | CH$_2$CH$_3$ | H | H | H |
| 661 | H | H | H | CH$_3$ | H | H | H |
| 662 | H | H | H | CH$_3$ | H | H | H |
| 663 | H | H | H | CH$_2$CH$_3$ | H | H | H |
| 664 | H | H | H | CH$_2$CH$_3$ | H | H | H |
| 665 | H | H | H | CH$_3$ | H | H | H |
| 666 | H | H | H | CH$_3$ | H | H | H |
| 667 | H | H | H | CH$_2$CH$_3$ | H | H | H |
| 668 | H | H | H | CH$_3$ | H | H | H |
| 669 | H | H | H | CH$_3$ | H | H | H |
| 670 | H | H | H | CH$_2$CH$_3$ | H | H | H |
| 671 | H | H | H | CH$_3$ | H | H | H |
| 672 | H | H | H | CH$_2$CH$_3$ | H | H | H |
| 673 | H | H | H | CH$_3$ | H | H | H |
| 674 | H | H | H | CH$_2$CH$_3$ | H | H | H |
| 675 | H | H | H | CH$_2$CH$_3$ | H | H | H |
| 676 | H | H | H | CH$_3$ | H | H | H |
| 677 | H | H | H | CH$_2$CH$_3$ | H | H | H |
| 678 | H | H | H | CH$_3$ | H | H | H |
| 679 | H | H | H | CH$_2$CH$_3$ | H | H | H |
| 680 | H | H | H | CH$_3$ | H | H | H |
| 681 | H | H | H | CH$_2$CH$_3$ | H | H | H |
| 682 | H | H | H | CH$_3$ | H | H | H |
| 683 | H | H | H | CH$_2$CH$_3$ | H | H | H |
| 684 | H | H | H | CH$_3$ | H | H | H |
| 685 | H | H | H | CH$_2$CH$_3$ | H | H | H |
| 686 | H | H | H | CH$_3$ | H | H | H |

TABLE 1-continued

| | | | | | | | |
|---|---|---|---|---|---|---|---|
| 687 | H | H | H | CH₂CH₃ | H | H | H |
| 688 | H | H | H | CH₃ | H | H | H |
| 689 | H | H | H | CH₂CH₃ | H | H | H |
| 690 | H | H | H | CH₃ | H | H | H |
| 691 | H | H | H | CH₂CH₃ | H | H | H |
| 692 | H | H | H | CH₃ | H | H | H |
| 693 | H | H | H | CH₂CH₃ | H | H | H |
| 694 | H | H | H | CH₃ | H | H | H |
| 695 | H | H | H | CH₂CH₃ | H | H | H |
| 696 | H | H | H | CH₃ | H | H | H |
| 697 | H | H | H | CH₂CH₃ | H | H | H |
| 698 | H | H | H | CH₃ | H | H | H |
| 699 | H | H | H | CH₂CH₃ | H | H | H |
| 700 | H | H | H | CH₃ | H | H | H |
| 701 | H | H | H | CH₂CH₃ | H | H | H |
| 702 | H | H | H | CH₃ | H | H | H |
| 703 | H | H | H | CH₂CH₃ | H | H | H |
| 704 | H | H | H | CH₃ | H | H | H |
| 705 | H | H | H | CH₂CH₃ | H | H | H |
| 706 | H | H | H | CH₃ | H | H | H |
| 707 | H | H | H | CH₂CH₃ | H | H | H |
| 708 | H | H | H | CH₃ | H | H | H |
| 709 | H | H | H | CH₂CH₃ | H | H | H |
| 710 | H | H | H | CH₃ | H | H | H |
| 711 | H | H | H | CH₂CH₃ | H | H | H |

| No. | $(R'_9)_n$ | $R_{10}$ | m.p. [° C.] |
|---|---|---|---|
| 001 | 2-Cl | H | solid |
| 002 | 2-Cl | H | |
| 003 | 2-Cl | H | |
| 004 | 2-Cl | H | |
| 005 | 2-Cl | H | |
| 006 | 2-Cl | H | |
| 007 | 2-Cl | H | |
| 008 | 2,3-Cl₂ | H | solid |
| 009 | 2,3-Cl₂ | H | |
| 010 | 2,3-Cl₂ | H | |
| 011 | 2,3-Cl₂ | H | |
| 012 | 2,3-Cl₂ | H | |
| 013 | 2,3-Cl₂ | H | |
| 014 | 3,4-Cl₂ | H | |
| 015 | 3,4-Cl₂ | H | |
| 016 | 3,4-Cl₂ | H | |
| 017 | 3,4-Cl₂ | H | |
| 018 | 3,4-Cl₂ | H | |
| 019 | 3,4-Cl₂ | H | |
| 020 | 2,4-Cl₂ | H | solid |
| 021 | 2,4-Cl₂ | H | |
| 022 | 2,4-Cl₂ | H | |
| 023 | 2,4-Cl₂ | H | |
| 024 | 2,4-Cl₂ | H | |
| 025 | 2,4-Cl₂ | H | |
| 026 | 2,4-Cl₂ | H | |
| 027 | 2,4-Cl₂ | H | |
| 028 | 4-CF₃ | H | 142-143 |
| 029 | 4-CF₃ | H | |
| 030 | 4-CF₃ | H | |
| 031 | 4-CF₃ | H | |
| 032 | 4-CF₃ | H | |
| 033 | 4-CF₃ | H | |
| 034 | 4-CH(CH₃)₂ | H | |
| 035 | 4-CH(CH₃)₂ | H | |
| 036 | 4-CH(CH₃)₂ | H | |
| 037 | 4-CH(CH₃)₂ | H | |
| 038 | 4-CH(CH₃)₂ | H | |
| 039 | 4-CH(CH₃)₂ | H | |
| 040 | 4-Cl | H | 120-121 |
| 041 | 4-Cl | H | oil |
| 042 | 4-Cl | H | |
| 043 | 4-Cl | H | |
| 044 | 4-Cl | H | 116-117 |
| 045 | 4-Cl | H | 105-106 |
| 046 | 4-Cl | H | 134-137 |
| 047 | 4-Cl | H | 110-111 |
| 048 | 4-Cl | H | 98-100 |
| 049 | 4-Cl | H | oil |
| 050 | 4-Cl | H | 96-97 |
| 051 | 4-Cl | H | 119-120 |

TABLE 1-continued

| | | | |
|---|---|---|---|
| 052 | 4-Cl | H | oil |
| 053 | 4-Cl | H | oil |
| 054 | 4-Cl | H | oil |
| 055 | 4-Cl | H | oil |
| 056 | 4-Cl | H | 77-78 |
| 057 | 4-Cl | H | oil |
| 058 | 4-Cl | H | oil |
| 059 | 4-Cl | H | oil |
| 060 | 2,4-Cl$_2$-6(N=CHCH=CH)-5 | | solid |
| 061 | 4-Cl | H | resinous |
| 062 | 4-Cl | H | solid |
| 063 | 4-Cl | H | |
| 064 | 4-Cl | H | |
| 065 | 4-Cl | H | |
| 066 | 4-Cl | H | |
| 067 | 4-Cl | H | |
| 068 | 3-OCH$_3$, 4-Cl | H | 68 |
| 069 | 2-OCH$_3$, 4-Cl | H | 108-109 |
| 070 | 2-OCH$_3$, 4-Cl | H | |
| 071 | 4-OCF$_3$ | H | 124-125 |
| 072 | 4-OCF$_3$ | H | |
| 073 | 4-OCF$_3$ | H | |
| 074 | 4-OCF$_3$ | H | |
| 075 | 4-OCF$_3$ | H | |
| 076 | 4-OCF$_3$ | H | |
| 077 | 4-OCF$_3$ | H | |
| 078 | 4-OCF$_3$ | H | |
| 079 | 2-F; 4-Cl | H | oil |
| 080 | 2-CH$_3$; 4-Cl | H | oil |
| 081 | 4-F | H | 100-103 |
| 082 | 4-F | H | |
| 083 | 4-F | H | |
| 084 | 4-F | H | |
| 085 | 4-F | H | |
| 086 | 4-F | H | |
| 087 | 4-F | H | |
| 088 | 4-F | H | |
| 089 | 2,4,6-Cl$_3$ | H | 128-130 |
| 090 | 3-F; 4-Cl | H | 123-124 |
| 091 | 3-CH$_3$; 4-Cl | H | 109-110 |
| 092 | H | 4-C$_6$H$_5$ | 135-136 |
| 093 | 4-CH$_3$ | H | 89-90 |
| 094 | 4-CH$_3$ | H | |
| 095 | 4-CH$_3$ | H | |
| 096 | 4-CH$_3$ | H | |
| 097 | 4-CH$_3$ | H | |
| 098 | 4-CH$_3$ | H | |
| 099 | 4-C$_6$H$_{11}$(cycl) | H | 145-146 |
| 100 | 3-CH$_3$ | H | 88-89 |
| 101 | 3,5-(CH$_3$)$_2$; 4-Cl | H | 118-119 |
| 102 | 3-CH$_2$CH$_3$, 4-Cl | H | 115-116 |
| 103 | 3-CH$_2$CH$_3$, 4-Cl | H | |
| 104 | 4-OCH$_3$ | H | oil |
| 105 | 4-OCH$_3$ | H | 127-128 |
| 106 | 4-OCH$_3$ | H | |
| 107 | 4-OCH$_3$ | H | |
| 108 | 4-OCH$_3$ | H | |
| 109 | 4-OCH$_3$ | H | |
| 110 | 4-OCH$_3$ | H | |
| 111 | 4-OCH$_3$ | H | |
| 112 | 4-OCH$_3$ | H | |
| 113 | 4-OCH$_3$ | H | |
| 114 | 4-OCH$_3$ | H | |
| 115 | 4-OCH$_3$ | H | |
| 116 | 4-OCH$_3$ | H | |
| 117 | 4-OCH$_3$ | H | |
| 118 | 4-OCH$_3$ | H | |
| 119 | 4-OCH$_3$ | H | |
| 120 | 4-OCH$_3$ | H | |
| 121 | 4-OCH$_3$ | H | |
| 122 | 4-OCH$_3$ | H | |
| 123 | 4-OCH$_3$ | H | |
| 124 | 4-OCH$_3$ | H | |
| 125 | 4-OCH$_3$ | H | |
| 126 | 4-OCH$_3$ | H | |
| 127 | 4-OCH$_3$ | H | |
| 128 | 4-OCH$_3$ | H | |
| 129 | 4-OCH$_3$ | H | |
| 130 | 4-OCH$_3$ | H | |

TABLE 1-continued
| | | | |
|---|---|---|---|
| 131 | 4-OCH$_3$ | H | |
| 132 | 4-OCH$_3$ | H | |
| 133 | 4-OCH$_3$ | H | |
| 134 | 4-OCH$_3$ | H | |
| 135 | 3-F; 4-OCH$_3$ | H | |
| 136 | 3-Cl; 4-OCH$_3$ | H | |
| 137 | 2-F; 4-OCH$_3$ | H | |
| 138 | 2-Cl; 4-OCH$_3$ | H | |
| 139 | 3-F; 4-OCH$_3$ | H | |
| 140 | 3-Cl; 4-OCH$_3$ | H | |
| 141 | 2-F; 4-OCH$_3$ | H | |
| 142 | 2-Cl; 4-OCH$_3$ | H | |
| 143 | 4-OCH$_3$ | H | |
| 144 | H | 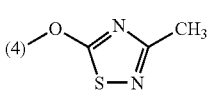 | oil |
| 145 | H | 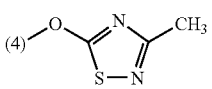 | |
| 146 | H | 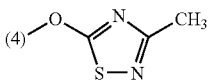 | |
| 147 | H | 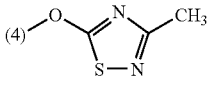 | |
| 148 | H | 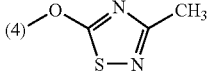 | |
| 149 | H | 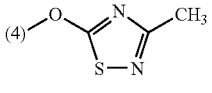 | |
| 150 | H | 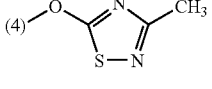 | |
| 151 | H | 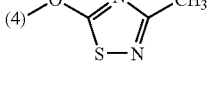 | |
| 152 | H | 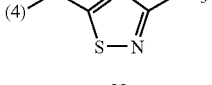 | |
| 153 | H | 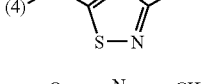 | |
| 154 | 2-Cl | 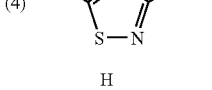 | |
| 155 | 4-CH$_2$CONH$_2$ | H | 113-116 |
| 156 | 4-CH$_2$CONH$_2$ | H | |
| 157 | H | 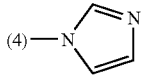 | 128-131 |
| 158 | H | 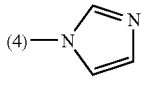 | |

TABLE 1-continued
| | | |
|---|---|---|
| 159 | H | 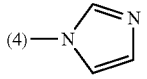 |
| 160 | H | 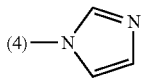 |
| 161 | H | 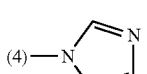 |
| 162 | H | 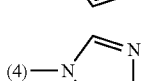 |
| 163 | H | 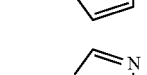 |
| 164 | H | 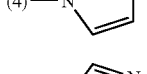 |
| 165 | H | 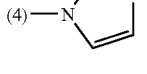 |
| 166 | H | 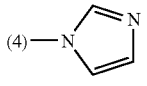 |
| 167 | H | 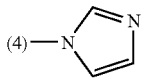 |
| 168 | H | 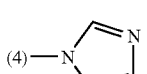 |
| 169 | H | 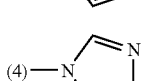 |
| 170 | H | 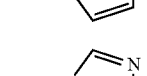 |
| 171 | H | 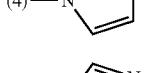 |
| 172 | 3-F | 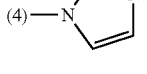 |
| 173 | 3-Cl | 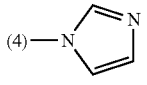 |
| 174 | 2-F | 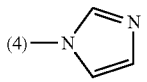 |
| 175 | 2-Cl | 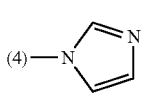 |

TABLE 1-continued
| # | R | R' | mp |
|---|---|---|---|
| 176 | 3-F | (4)—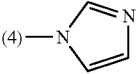 | |
| 177 | 3-Cl | (4)—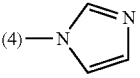 | |
| 178 | 2-F | (4)—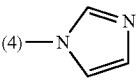 | |
| 179 | 2-Cl | (4)—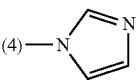 | |
| 180 | H | (4)—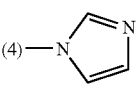 | |
| 181 | H | (4)—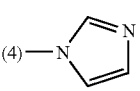 | |
| 182 | H | (4)—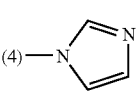 | |
| 183 | H | (4)—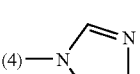 | |
| 184 | H | (4)—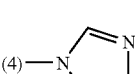 | |
| 185 | H | (4)—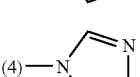 | |
| 186 | H | (4)—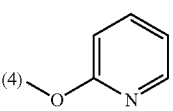 | 169-170 |
| 187 | 4-O(CH$_2$)$_5$CH$_3$ | H | 93-94 |
| 188 | H | 4-C(CH$_3$)=NOCH$_3$ | 106-107 |
| 189 | H | 4-C(CH$_3$)=NOCH$_3$ | |
| 190 | H | 4-CONH$_2$ | 174-176 |
| 191 | H | 4-CONH$_2$ | |
| 192 | H | 4-CONH$_2$ | |
| 193 | H | 4-CONH$_2$ | |
| 194 | H | 4-CONH$_2$ | |
| 195 | H | 4-CONH$_2$ | |
| 196 | H | 4-CONH$_2$ | |
| 197 | H | (4)—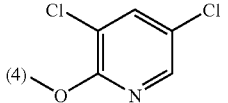 | oil |
| 198 | 4-(C(=NOCH$_3$)CH$_2$—CH$_2$—CH$_2$—CH$_2$)-3 | | 100 |
| 199 | 4-NHCOC(CH$_3$)$_3$ | H | 165-166 |
| 200 | 4-NHCOC(CH$_3$)$_3$ | H | |
| 201 | 4-SCH$_3$ | H | 102 |
| 202 | 4-SCH$_3$ | H | |
| 203 | 4-SCH$_3$ | H | |
| 204 | 4-SCH$_3$ | H | |
| 205 | 4-SCH$_3$ | H | |
| 206 | 4-SCH$_3$ | H | |

TABLE 1-continued
| | | | |
|---|---|---|---|
| 207 | 4-SCH$_3$ | H | |
| 208 | 4-OCH(CH$_3$)CONH$_2$ | H | oil |
| 209 | H | 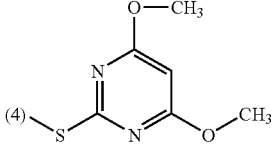 | 142 |
| 210 | H | 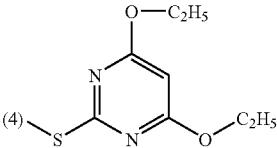 | 89-90 |
| 211 | 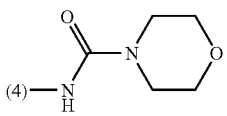 | H | 180-181 |
| 212 | 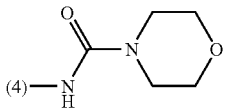 | H | |
| 213 | 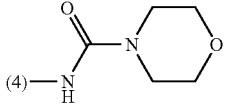 | H | |
| 214 | 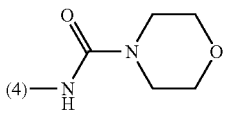 | H | |
| 215 | 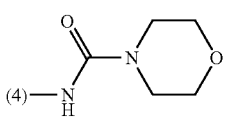 | H | |
| 216 | 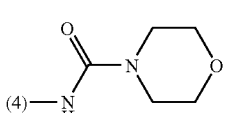 | H | |
| 217 | 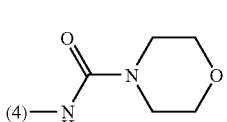 | H | |
| 218 | 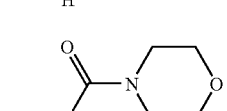 | H | |
| 219 | 4-SO$_2$CH$_3$ | H | |
| 220 | 4-SO$_2$CH$_3$ | H | 152-153 |
| 221 | 4-SO$_2$CH$_3$ | H | |
| 222 | 4-SO$_2$CH$_3$ | H | |
| 223 | 4-SO$_2$CH$_3$ | H | |
| 224 | 4-SO$_2$CH$_3$ | H | |
| 225 | 4-SO$_2$CH$_3$ | H | |

TABLE 1-continued
| | | | | |
|---|---|---|---|---|
| 226 | 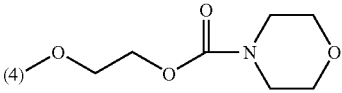 | | H | 119-120 |
| 227 | 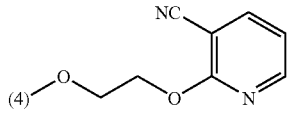 | | H | oil |
| 228 | 4-CN | | H | oil |
| 229 | 4-CN | | H | 153-154 |
| 230 | 4-CN | | H | |
| 231 | 4-CN | | H | oil |
| 232 | 4-CN | | H | |
| 233 | 4-CN | | H | |
| 234 | 4-CN | | H | |
| 235 | 4-CN | | H | |
| 236 | 4-CN | | H | |
| 237 | 4-CN | | H | |
| 238 | 4-CN | | H | |
| 239 | 4-CN | | H | |
| 240 | 4-CN | | H | |
| 241 | 4-CN | | H | |
| 242 | 4-CN | | H | |
| 243 | 4-CN | | H | |
| 244 | 4-CN | | H | |
| 245 | 4-CN | | H | |
| 246 | 4-CN | | H | |
| 247 | 4-CN | | H | |
| 248 | 4-CN | | H | |
| 249 | 4-CN | | H | |
| 250 | 4-CN | | H | |
| 251 | 4-CN | | H | |
| 252 | 4-CN | | H | |
| 253 | 4-CN | | H | |
| 254 | 4-CN | | H | |
| 255 | 4-CN | | H | |
| 256 | 4-CN | | H | |
| 257 | 4-CN | | H | |
| 258 | 4-CN | | H | |
| 259 | 3-F; 4-CN | | H | |
| 260 | 3-Cl; 4-CN | | H | |
| 261 | 2-F; 4-CN | | H | |
| 262 | 2-Cl; 4-CN | | H | |
| 263 | 3-F; 4-CN | | H | |
| 264 | 3-Cl; 4-CN | | H | |
| 265 | 2-F; 4-CN | | H | |
| 266 | 2-Cl; 4-CN | | H | |
| 267 | 4-CN | | H | |
| 268 | 4-CN | | H | |
| 269 | 4-CN | | H | |
| 270 | 2-CH$_3$; 4-CN | | H | |
| 271 | H | | 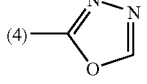 | 137-138 |
| 273 | H | | 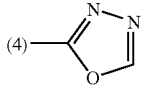 | |
| 274 | H | | 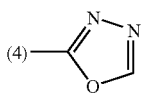 | |
| 275 | H | | 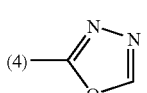 | |

TABLE 1-continued

| # | R | Ar | mp |
|---|---|---|---|
| 276 | H | (4)-[1,3,4-oxadiazol-2-yl] | |
| 277 | H | (4)-[1,3,4-oxadiazol-2-yl] | 88-89 |
| 278 | H | (4)-[1,3,4-oxadiazol-2-yl] | |
| 279 | H | (4)-[1,3,4-oxadiazol-2-yl] | |
| 280 | H | (4)-[1,3,4-oxadiazol-2-yl] | |
| 281 | H | (4)-[1,3,4-oxadiazol-2-yl] | |
| 282 | H | (4)-[1,3,4-oxadiazol-2-yl] | |
| 283 | 4-SOCH$_3$ | H | 160-162 |
| 284 | H | (4)-[5-ethyl-1,3,4-oxadiazol-2-yl]-C$_2$H$_5$ | 88-91 |
| 285 | H | (4)-[5-ethyl-1,3,4-oxadiazol-2-yl]-C$_2$H$_5$ | |
| 286 | H | (4)-[5-ethyl-1,3,4-oxadiazol-2-yl]-C$_2$H$_5$ | |
| 287 | H | (4)-[5-ethyl-1,3,4-oxadiazol-2-yl]-C$_2$H$_5$ | |
| 288 | 4-OCH$_2$CH$_3$ | H | 85-86 |
| 289 | 4-OCH$_2$CH$_3$ | H | 84-85 |
| 290 | 4-OCH$_2$CH$_3$ | H | |
| 291 | 4-OCH$_2$CH$_3$ | H | |
| 292 | 4-OCH$_2$CH$_3$ | H | |
| 293 | 4-OCH$_2$CH$_3$ | H | |
| 294 | 4-OCH$_2$CH$_3$ | H | |
| 295 | 4-OCH$_2$CH$_3$ | H | |
| 296 | 4-OCH$_2$CH$_3$ | H | |
| 297 | 4-OCH$_2$CH$_3$ | H | |
| 298 | 4-OCH$_2$CH$_3$ | H | |
| 299 | 4-OCH$_2$CH$_3$ | H | |
| 300 | 4-OCH$_2$CH$_3$ | H | |
| 301 | 4-OCH$_2$CH$_3$ | H | |
| 302 | 4-OCH$_2$CH$_3$ | H | |
| 303 | 4-OCH$_2$CH$_3$ | H | |
| 304 | 4-OCH$_2$CH$_3$ | H | |
| 305 | 4-OCH$_2$CH$_3$ | H | |
| 306 | 4-OCH$_2$CH$_3$ | H | |

TABLE 1-continued
| | | | |
|---|---|---|---|
| 307 | 4-OCH$_2$CH$_3$ | H | |
| 308 | 4-OCH$_2$CH$_3$ | H | |
| 309 | 4-OCH$_2$CH$_3$ | H | |
| 310 | 4-OCH$_2$CH$_3$ | H | |
| 311 | 4-OCH$_2$CH$_3$ | H | |
| 312 | 4-OCH$_2$CH$_3$ | H | |
| 313 | 4-OCH$_2$CH$_3$ | H | |
| 314 | 4-OCH$_2$CH$_3$ | H | |
| 315 | 4-OCH$_2$CH$_3$ | H | |
| 316 | 4-OCH$_2$CH$_3$ | H | |
| 317 | 4-OCH$_2$CH$_3$ | H | |
| 318 | 4-OCH$_2$CH$_3$ | H | |
| 319 | 3-F; 4-OCH$_2$CH$_3$ | H | |
| 320 | 3-Cl; 4-OCH$_2$CH$_3$ | H | |
| 321 | 2-F; 4-OCH$_2$CH$_3$ | H | |
| 322 | 2-Cl; 4-OCH$_2$CH$_3$ | H | |
| 323 | 3-F; 4-OCH$_2$CH$_3$ | H | |
| 324 | 3-Cl; 4-OCH$_2$CH$_3$ | H | |
| 325 | 2-F; 4-OCH$_2$CH$_3$ | H | |
| 326 | 2-Cl; 4-OCH$_2$CH$_3$ | H | |
| 327 | 4-OCH$_2$CH$_3$ | H | |
| 328 | 4-OCH$_2$CH$_3$ | H | |
| 329 | 4-OCH$_2$CH$_3$ | H | |
| 330 | 4-OCH$_2$CH$_3$ | H | |
| 331 | H | 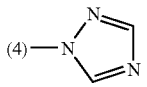 | oil |
| 332 | H | 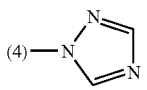 | 103-105 |
| 333 | H | 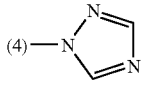 | |
| 334 | H | 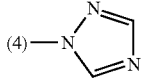 | |
| 335 | H | 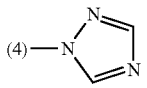 | |
| 336 | H | 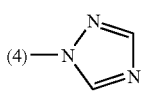 | |
| 337 | H | 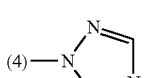 | |
| 338 | H | 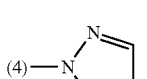 | |
| 339 | H | 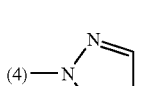 | |
| 340 | H | 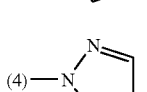 | |

TABLE 1-continued
| | | |
|---|---|---|
| 341 | H | 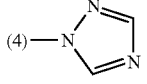 |
| 342 | H | 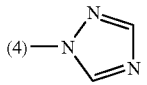 |
| 343 | H | 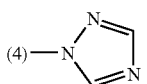 |
| 344 | H | 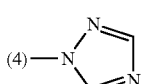 |
| 345 | H | 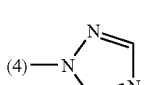 |
| 346 | H | 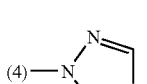 |
| 347 | H | 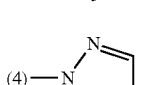 |
| 348 | H | 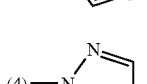 |
| 349 | H | 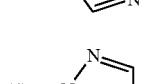 |
| 350 | H | 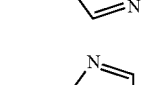 |
| 351 | H | 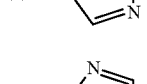 |
| 352 | H | 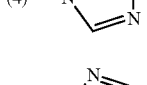 |
| 353 | H | 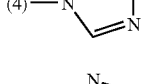 |
| 354 | H | 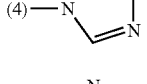 |
| 355 | H | 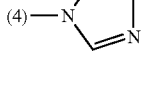 |

TABLE 1-continued
| | | |
|---|---|---|
| 356 | H | 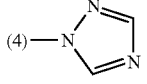 |
| 357 | H | 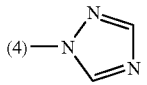 |
| 358 | H | 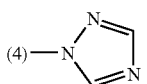 |
| 359 | H | 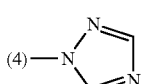 |
| 360 | H | 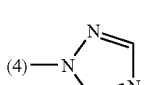 |
| 361 | H | 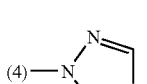 |
| 362 | 3-F | 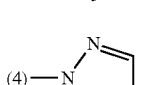 |
| 363 | 3-Cl | 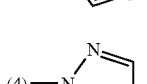 |
| 364 | 2-F | 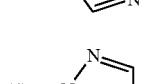 |
| 365 | 2-Cl | 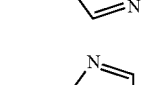 |
| 366 | 3-F | 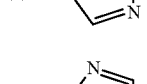 |
| 367 | 3-Cl | 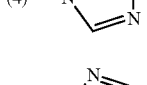 |
| 368 | 2-F | 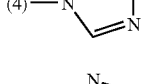 |
| 369 | 2-Cl | 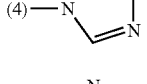 |
| 370 | H | 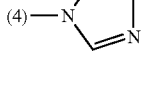 |

TABLE 1-continued
| | | | |
|---|---|---|---|
| 371 | H | 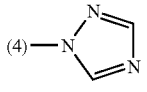 | |
| 372 | H | 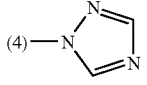 | |
| 373 | H | 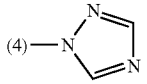 | |
| 374 | H | 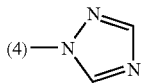 | |
| 375 | H | 4-COOCH$_3$ | 13-134 |
| 376 | H | 4-COOCH$_3$ | |
| 377 | H | 4-COOCH$_3$ | |
| 378 | H | 4-COC$_6$H$_5$ | solid |
| 379 | H | 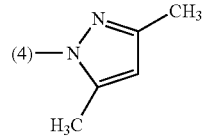 | oil |
| 380 | H | 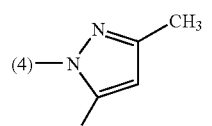 | |
| 381 | H | 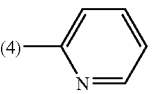 | 124-125 |
| 382 | H | 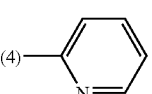 | |
| 383 | H | 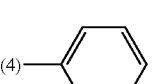 | |
| 384 | H | 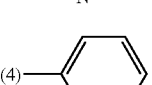 | |
| 385 | H | 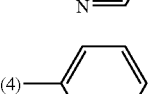 | |
| 386 | H | 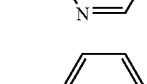 | |
| 387 | H | 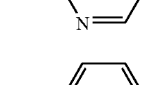 | |

TABLE 1-continued
| | | |
|---|---|---|
| 388 | H | 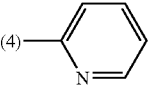 (4)- pyridine |
| 389 | H | 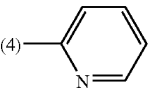 (4)- pyridine |
| 390 | H | 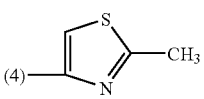 (4)- 2-methylthiazole |
| 391 | H | 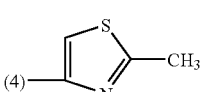 (4)- 2-methylthiazole |
| 392 | H | 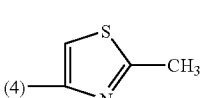 (4)- 2-methylthiazole |
| 393 | H | 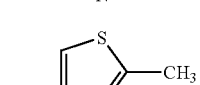 (4)- 2-methylthiazole |
| 394 | H | 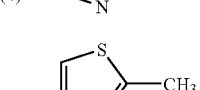 (4)- 2-methylthiazole |
| 395 | H | 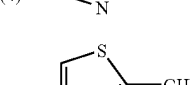 (4)- 2-methylthiazole |
| 396 | H | 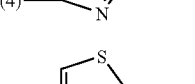 (4)- 2-methylthiazole |
| 397 | H | 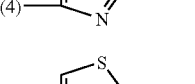 (4)- 2-methylthiazole |
| 398 | H | 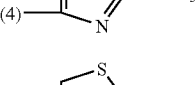 (4)- 2-methylthiazole |
| 399 | H | 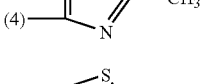 (4)- 2-methylthiazole |
| 400 | H | 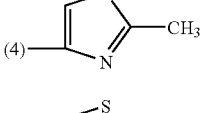 (4)- 2-methylthiazole |
| 401 | H | 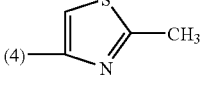 (4)- 2-methylthiazole |
| 402 | H | 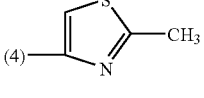 (4)- 2-methylthiazole |

TABLE 1-continued
| | | |
|---|---|---|
| 403 | H | 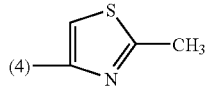 (4)- 2-methylthiazol-4-yl |
| 404 | H | 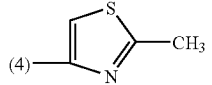 (4)- 2-methylthiazol-4-yl |
| 405 | H | 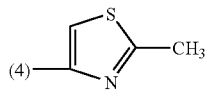 (4)- 2-methylthiazol-4-yl |
| 406 | H | 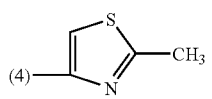 (4)- 2-methylthiazol-4-yl |
| 407 | 3-F | 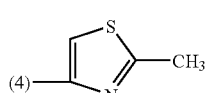 (4)- 2-methylthiazol-4-yl |
| 408 | 3-Cl | 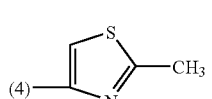 (4)- 2-methylthiazol-4-yl |
| 409 | 2-F | 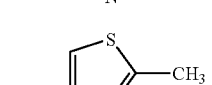 (4)- 2-methylthiazol-4-yl |
| 410 | 2-Cl | 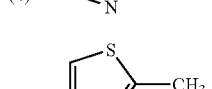 (4)- 2-methylthiazol-4-yl |
| 411 | 3-F | 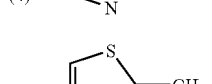 (4)- 2-methylthiazol-4-yl |
| 412 | 3-Cl | 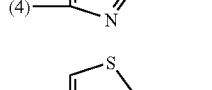 (4)- 2-methylthiazol-4-yl |
| 413 | 2-F | 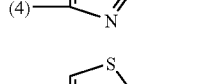 (4)- 2-methylthiazol-4-yl |
| 414 | 2-Cl | 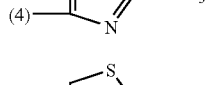 (4)- 2-methylthiazol-4-yl |
| 415 | H | 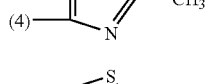 (4)- 2-methylthiazol-4-yl |
| 416 | H | 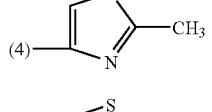 (4)- 2-methylthiazol-4-yl |
| 417 | H | 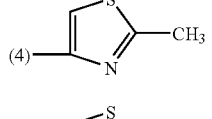 (4)- 2-methylthiazol-4-yl |

TABLE 1-continued
| 418 | H | 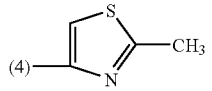 | |
| 419 | H | 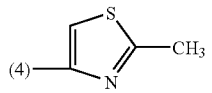 | |
| 420 | H | 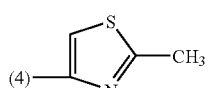 | |
| 421 | H | 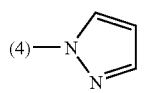 | solid |
| 422 | H | 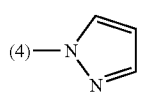 | solid |
| 423 | H | 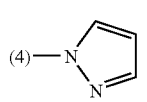 | |
| 424 | H | 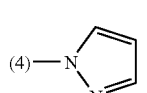 | |
| 425 | H | 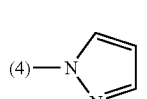 | |
| 426 | H | 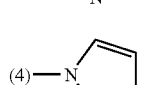 | |
| 427 | H | 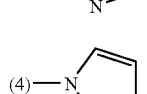 | |
| 428 | H | 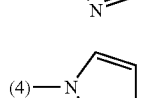 | |
| 429 | H | 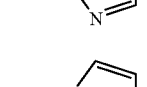 | |
| 430 | H | 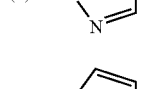 | |
| 431 | H | 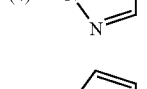 | |
| 432 | H | 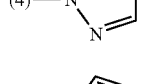 | |

TABLE 1-continued
| | | |
|---|---|---|
| 433 | H | (4)—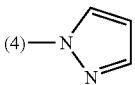 |
| 434 | H | (4)—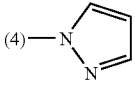 |
| 435 | H | (4)—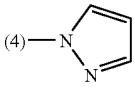 |
| 436 | H | (4)—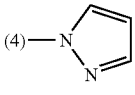 |
| 437 | 3-F | (4)—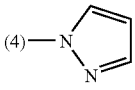 |
| 438 | 3-Cl | (4)—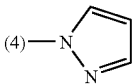 |
| 439 | 2-F | (4)—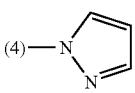 |
| 440 | 2-Cl | (4)—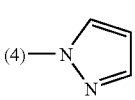 |
| 441 | 3-F | (4)—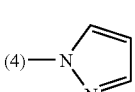 |
| 442 | 3-Cl | (4)—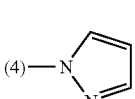 |
| 443 | 2-F | (4)—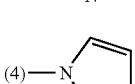 |
| 444 | 2-Cl | (4)—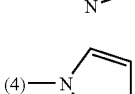 |
| 445 | H | (4)—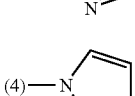 |
| 446 | H | (4)—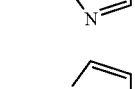 |
| 447 | H | (4)—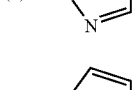 |

TABLE 1-continued
| | | | |
|---|---|---|---|
| 448 | H | (4)—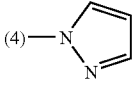 | |
| 449 | H | (4)—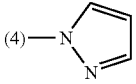 | |
| 450 | H | (4)—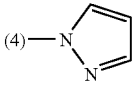 | |
| 451 | | 4-(COCH$_2$—CH$_2$—CH$_2$—CH$_2$)-3 | 159-160 |
| 452 | H | (4)—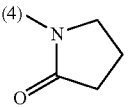 | 136-137 |
| 453 | | 4-(COCH$_2$—CH$_2$—CH$_2$—CH$_2$)-3 | 117-119 |
| 454 | H | 4-CON(CH$_3$)$_2$ | 148-149 |
| 455 | H | (4)—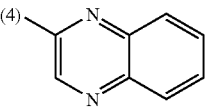 | 112-113 |
| 456 | 4-OCOCH$_3$ | H | 143-145 |
| 457 | 4-OH | H | 120-121 |
| 458 | 4-OH | H | resinous |
| 459 | 4-OH | H | |
| 460 | 4-OH | H | |
| 461 | 4-OH | H | |
| 462 | 4-OH | H | |
| 463 | 4-OH | H | |
| 464 | 4-OH | H | |
| 465 | 4-OH | H | |
| 466 | 4-OH | H | |
| 467 | | 4-(C(CH$_3$)=C—C(O)—O)-3 | 190-191 |
| 468 | | 4-(CH=CH—C(O)—O)-3 | 131-132 |
| 469 | 4-OCH(CH$_3$)$_2$ | H | 98-99 |
| 470 | 4-OCH(CH$_3$)$_2$ | H | |
| 471 | 4-OCH(CH$_3$)$_2$ | H | |
| 472 | 4-OCH(CH$_3$)$_2$ | H | |
| 473 | 4-OCH(CH$_3$)$_2$ | H | |
| 474 | 4-OCH(CH$_3$)$_2$ | H | |
| 475 | 4-OCH(CH$_3$)$_2$ | H | |
| 476 | 4-OCH(CH$_3$)$_2$ | H | |
| 477 | 4-OCH(CH$_3$)$_2$ | H | |
| 478 | 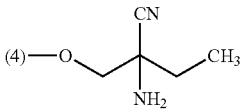 | H | 108-109 |
| 479 | 4-NO$_2$ | H | glass |
| 480 | 4-NH$_2$ | H | 153-154 |
| 481 | 4-NH$_2$ | H | |
| 482 | 4-NH$_2$ | H | |
| 483 | 4-NH$_2$ | H | |
| 484 | 4-NH$_2$ | H | |
| 485 | 4-NH$_2$ | H | |
| 486 | 4-NH$_2$ | H | |
| 487 | 4-NH$_2$ | H | |
| 488 | 4-NH$_2$ | H | |
| 489 | 4-I | H | resinous |
| 490 | 4-I | H | |
| 491 | 4-I | H | |
| 492 | 4-I | H | |
| 493 | 4-I | H | |
| 494 | 4-I | H | |

TABLE 1-continued

| | | | |
|---|---|---|---|
| 495 | 4-I | H | |
| 496 | 4-I | H | |
| 497 | 4-I | H | |
| 498 | 4-I | H | |
| 499 | 4-Br | H | |
| 500 | 4-Br | H | |
| 501 | 4-Br | H | |
| 502 | 4-Br | H | |
| 503 | 4-Br | H | |
| 504 | 4-Br | H | |
| 505 | 4-Br | H | |
| 506 | 4-Br | H | |
| 507 | 4-Br | H | |
| 508 | 4-Br | H | |
| 509 | 4-CH(CH$_3$)$_2$ | H | resinous |
| 510 | 4-OCH$_2$C$_6$H$_5$ | H | resinous |
| 511 | 4-OCH$_2$C$_6$H$_5$ | H | |
| 512 | 3-F | 4-COCH$_2$CH$_3$ | 103-104 |
| 513 | 3-F | 4-COCH$_2$CH$_3$ | 114-118 |
| 514 | H | 4-COCH$_2$CH$_3$ | oil |
| 515 | H | 4-COCH$_2$CH$_3$ | |
| 516 | H | 4-COCH$_2$CH$_3$ | |
| 517 | H | 4-COCH2CH3 | 124-126 |
| 518 | H | 4-COCH$_2$CH$_3$ | |
| 519 | H | 4-COCH$_2$CH$_3$ | |
| 520 | H | 4-COCH$_2$CH$_3$ | |
| 521 | H | 4-COCH$_2$CH$_3$ | |
| 522 | H | 4-COCH$_2$CH$_3$ | |
| 523 | H | 4-COCH$_2$CH$_3$ | |
| 524 | H | 4-COCH$_2$CH$_3$ | |
| 525 | H | 4-COCH$_2$CH$_3$ | |
| 526 | H | 4-COCH$_2$CH$_3$ | |
| 527 | H | 4-COCH$_2$CH$_3$ | |
| 528 | H | 4-COCH$_2$CH$_3$ | |
| 529 | H | 4-COCH$_2$CH$_3$ | |
| 530 | H | 4-COCH$_2$CH$_3$ | |
| 531 | H | 4-COCH$_2$CH$_3$ | |
| 532 | H | 4-COCH$_2$CH$_3$ | |
| 533 | H | 4-COCH$_2$CH$_3$ | |
| 534 | H | 4-COCH$_2$CH$_3$ | |
| 535 | H | 4-COCH$_2$CH$_3$ | |
| 536 | H | 4-COCH$_2$CH$_3$ | |
| 537 | H | 4-COCH$_2$CH$_3$ | |
| 538 | H | 4-COCH$_2$CH$_3$ | |
| 539 | H | 4-COCH$_2$CH$_3$ | |
| 540 | H | 4-COCH$_2$CH$_3$ | |
| 541 | H | 4-COCH$_2$CH$_3$ | |
| 542 | H | 4-COCH$_2$CH$_3$ | |
| 543 | H | 4-COCH$_2$CH$_3$ | |
| 544 | H | 4-COCH$_2$CH$_3$ | |
| 545 | 3-F | 4-COCH$_2$CH$_3$ | |
| 546 | 3-Cl | 4-COCH$_2$CH$_3$ | |
| 547 | 2-F | 4-COCH$_2$CH$_3$ | |
| 548 | 2-Cl | 4-COCH$_2$CH$_3$ | |
| 549 | 3-F | 4-COCH$_2$CH$_3$ | |
| 550 | 3-Cl | 4-COCH$_2$CH$_3$ | |
| 551 | 2-F | 4-COCH$_2$CH$_3$ | |
| 552 | 2-Cl | 4-COCH$_2$CH$_3$ | |
| 553 | H | 4-COCH$_2$CH$_3$ | |
| 554 | H | 4-COCH$_2$CH$_3$ | |
| 555 | H | 4-COCH$_2$CH$_3$ | |
| 556 | H | 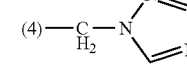 | |
| 557 | H | 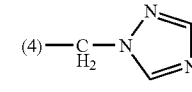 | solid |
| 558 | H | 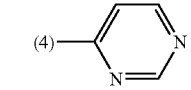 | solid |

TABLE 1-continued

| | | | |
|---|---|---|---|
| 559 | H | (4)-pyrimidin-4-yl | |
| 560 | H | (4)-pyrimidin-4-yl | |
| 561 | H | (4)-pyrimidin-4-yl | |
| 562 | H | (4)-pyrimidin-4-yl | |
| 563 | H | (4)-pyrimidin-4-yl | |
| 564 | H | 4-COCH3 | oil |
| 565 | H | 4-COCH$_3$ | oil |
| 566 | H | 4-COCH$_3$ | |
| 567 | H | 4-COCH$_3$ | |
| 568 | H | 4-COCH$_3$ | 143-144 |
| 569 | H | 4-COCH$_3$ | |
| 570 | H | 4-COCH$_3$ | |
| 571 | H | 4-COCH$_3$ | |
| 572 | H | 4-COCH$_3$ | |
| 573 | H | 4-COCH$_3$ | |
| 574 | H | 4-COCH$_3$ | |
| 575 | H | 4-COCH$_3$ | |
| 576 | H | 4-COCH$_3$ | |
| 577 | H | 4-COCH$_3$ | |
| 578 | H | 4-COCH$_3$ | |
| 579 | H | 4-COCH$_3$ | |
| 580 | H | 4-COCH$_3$ | |
| 581 | H | 4-COCH$_3$ | |
| 582 | H | 4-COCH$_3$ | |
| 583 | H | 4-COCH$_3$ | |
| 584 | H | 4-COCH$_3$ | |
| 585 | H | 4-COCH$_3$ | |
| 586 | H | 4-COCH$_3$ | |
| 587 | H | 4-COCH$_3$ | |
| 588 | H | 4-COCH$_3$ | |
| 589 | H | 4-COCH$_3$ | |
| 590 | H | 4-COCH$_3$ | |
| 591 | H | 4-COCH$_3$ | |
| 592 | H | 4-COCH$_3$ | |
| 593 | H | 4-COCH$_3$ | |
| 594 | H | 4-COCH$_3$ | |
| 595 | H | 4-COCH$_3$ | |
| 596 | 3-F | 4-COCH$_3$ | |
| 597 | 3-Cl | 4-COCH$_3$ | |
| 598 | 2-F | 4-COCH$_3$ | |
| 599 | 2-Cl | 4-COCH$_3$ | |
| 600 | 3-F | 4-COCH$_3$ | |
| 601 | 3-Cl | 4-COCH$_3$ | |
| 602 | 2-F | 4-COCH$_3$ | |
| 603 | 2-Cl | 4-COCH$_3$ | |
| 604 | H | 4-COCH$_3$ | |
| 605 | H | 4-COCH$_3$ | |
| 606 | H | 4-COCH$_3$ | |
| 607 | H | -4-COCH$_3$ | 152-153 $n_D^{20}$ = +10.7° (CHCl$_3$c 1, 34) |
| 608 | H | -4-COCH$_3$ | |
| 609 | H | -4-COCH$_3$ | |
| 610 | H | -4-COCH$_3$ | 152-153 $n_D^{20}$ = +10.7° (CHCl$_3$c 1, 34) |
| 611 | H | -4-COCH$_3$ | |
| 612 | H | -4-COCH$_3$ | |

TABLE 1-continued

| | | | |
|---|---|---|---|
| 613 | H | 4-COCH₃ | |
| 614 | 3,4-(OCH₃)₂ | H | |
| 615 | 3,4-(OCH₃)₂ | H | |
| 616 | 3,4-(OCH₃)₂ | H | |
| 617 | 3,4-(OCH₃)₂ | H | |
| 618 | 3,4-(OCH₃)₂ | H | |
| 619 | 3,4-(OCH₃)₂ | H | |
| 620 | 3,4-(OCH₃)₂ | H | |
| 621 | 3-OCH₃; 4-OCH₂CH=CH₂ | H | |
| 622 | 3-OCH₃; 4-OCH₂CH=CH₂ | H | |
| 623 | 3-OCH₃; 4-OCH₂CH=CH₂ | H | |
| 624 | 3-OCH₃; 4-OCH₂CH=CH₂ | H | |
| 625 | 3-OCH₃; 4-OCH₂CH=CH₂ | H | |
| 626 | 3-OCH₃; 4-OCH₂CH=CH₂ | H | |
| 627 | 3-OCH₃; 4-OCH₂CH=CH₂ | H | |
| 628 | 3-OCH₃; 4-OCH₂CH=CH₂ | H | |
| 629 | 3-OCH₃; 4-OCH₂CH=CH₂ | H | |
| 630 | 3-OCH₃; 4-OCH₂C≡CH | H | |
| 631 | 3-OCH₃; 4-OCH₂C≡CH | H | |
| 632 | 3-OCH₃; 4-OCH₂C≡CH | H | |
| 633 | 3-OCH₃; 4-OCH₂C≡CH | H | |
| 634 | 3-OCH₃; 4-OCH₂C≡CH | H | |
| 635 | 3-OCH₃; 4-OCH₂C≡CH | H | |
| 636 | 3-OCH₃; 4-OCH₂C≡CH | H | |
| 637 | 3-OCH₃; 4-OCH₂C≡CH | H | |
| 638 | 3-OCH₃; 4-OCH₂C≡CH | H | |
| 639 | 4-OCH₂C≡CH | H | |
| 640 | 4-OCH₂C≡CH | H | |
| 641 | 4-OCH₂C≡CH | H | |
| 642 | 4-OCH₂C≡CH | H | |
| 643 | 4-OCH₂C≡CH | H | |
| 644 | 4-OCH₂C≡CH | H | |
| 645 | 4-OCH₂C≡CH | H | |
| 646 | 4-OCH₂C≡CH | H | |
| 647 | 4-OCH₂C≡CH | H | |
| 648 | 4-OCH₂CH=CH₂ | H | |
| 649 | 4-OCH₂CH=CH₂ | H | |
| 650 | 4-OCH₂CH=CH₂ | H | |
| 651 | 4-OCH₂CH=CH₂ | H | |
| 652 | 4-OCH₂CH=CH₂ | H | |
| 653 | 4-OCH₂CH=CH₂ | H | |
| 654 | 4-OCH₂CH=CH₂ | H | |
| 655 | 4-OCH₂CH=CH₂ | H | |
| 656 | 4-OCH₂CH=CH₂ | H | |
| 657 | 2-Cl | 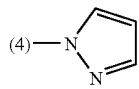 | (−) isomer |
| 658 | 3-F | 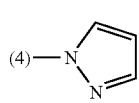 | (+)-isomer |
| 659 | H | 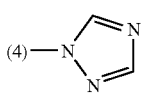 | (−) isomer |

TABLE 1-continued
| | | | |
|---|---|---|---|
| 660 | H | 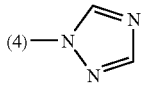 | (+)-isomer |
| 661 | H | 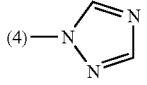 | (+)-isomer |
| 662 | H | 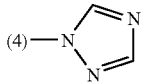 | (−) isomer |
| 663 | 4-OCH₂CH₃ | H | (−) isomer |
| 664 | 4-OCH₂CH₃ | H | (+)-isomer |
| 665 | 4-OCH₂CH₃ | H | (−)-isomer |
| 666 | 4-OCH₂CH₃ | H | (+)-isomer |
| 667 | H | 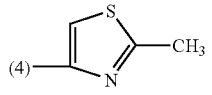 | (−)-isomer |
| 668 | H | 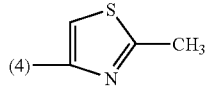 | (−)-isomer |
| 669 | H | 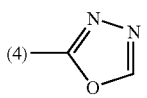 | (−)-isomer |
| 670 | 4-CN | H | (−)-isomer |
| 671 | 4-CN | H | (−)-isomer |
| 672 | 4-CN | H | (+)-isomer |
| 673 | 4-CN | H | (+)-isomer |
| 674 | 4-Cl | H | (−)-isomer |
| 675 | 4-Cl | H | (+)-isomer |
| 676 | H | 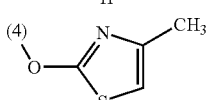 | |
| 677 | H | 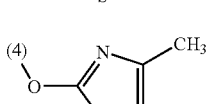 | |
| 678 | H | 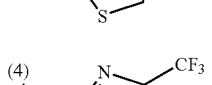 | |
| 679 | H | 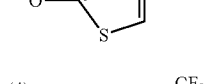 | |
| 680 | H | 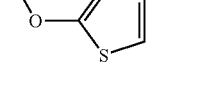 | |
| 681 | H | 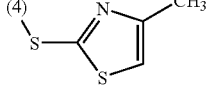 | |

TABLE 1-continued

| | | |
|---|---|---|
| 682 | H | (4)-S-[thiazole-4-CF3] |
| 683 | H | (4)-S-[thiazole-4-CF3] |
| 684 | H | (4)-NH-[thiazole-4-CH3] |
| 68 | H | (4)-NH-[thiazole-4-CH3] |
| 686 | H | (4)-NH-[thiazole-4-CF3] |
| 687 | H | (4)-NH-[thiazole-4-CF3] |
| 688 | H | (4)-N(CH3)-[thiazole-4-CH3] |
| 689 | H | (4)-N(CH3)-[thiazole-4-CH3] |
| 690 | H | (4)-N(CH3)-[thiazole-4-CF3] |
| 691 | H | (4)-N(CH3)-[thiazole-4-CF3] |
| 692 | H | (4)-[1,3,4-thiadiazole] |
| 693 | H | (4)-[1,3,4-thiadiazole] |
| 694 | H | (4)-[5-methyl-1,3,4-thiadiazole] |
| 695 | H | (4)-[5-methyl-1,3,4-thiadiazole] |

TABLE 1-continued
| 696 | H | 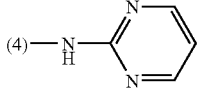 |
| 697 | H | 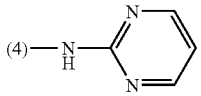 |
| 698 | H | 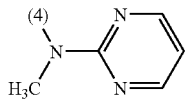 |
| 699 | H | 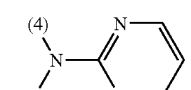 |
| 700 | H | 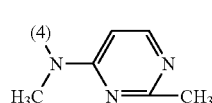 |
| 701 | H | 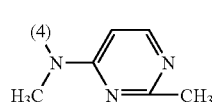 |
| 702 | H | 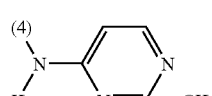 |
| 703 | H | 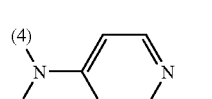 |
| 704 | H | 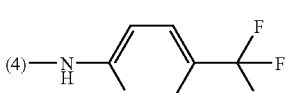 |
| 705 | H | 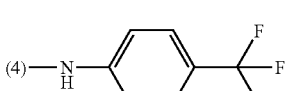 |
| 706 | H | 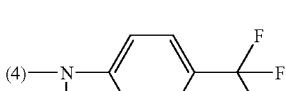 |
| 707 | H | 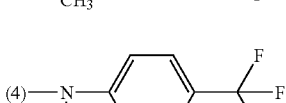 |
| 708 | H | 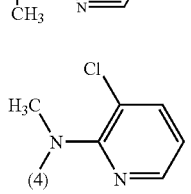 |

TABLE 1-continued

| | | |
|---|---|---|
| 709 | H | 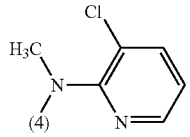 |
| 710 | H | 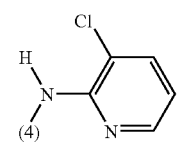 |
| 711 | H | 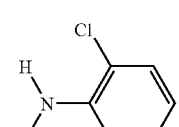 |

Formulations may be prepared analogously to those described in, for example, WO 95/30651.

BIOLOGICAL EXAMPLES

D-1: Action against *Plasmopara viticola* on Vines a) Residual-protective Action Vine seedlings are sprayed at the 4- to 5-leaf stage with a spray mixture (0.02% active ingredient) prepared from a wettable powder formulation of the test compound. After 24 hours, the treated plants are infected with a sporangia suspension of the fungus. Fungus infestation is evaluated after incubation for 6 days at 95-100% relative humidity and +20° C.

b) Residual-curative Action

Vine seedlings are infected at the 4- to 5-leaf stage with a sporangia suspension of the fungus. After incubation for 24 hours in a humidity chamber at 95-100% relative humidity and +20° C., the infected plants are dried and sprayed with a spray mixture (0.02% active ingredient) prepared from a wettable powder formulation of the test compound. After the spray coating has dried, the treated plants are placed in the humidity chamber again. Fungus infestation is evaluated 6 days after infection.

Compounds of Tables 1 exhibit a good fungicidal action against *Plasmopara viticola* on vines. Compounds No. 040, 052, 059, 071, 091, 101, 102, 104, 105, 157, 186, 197, 220, 228, 229, 271, 288, 289, 331, 332, 378, 381, 391, 421, 422, 452, 453, 469, 479, 489, 499, 512, 513, 514, 517, 464, 568, 607, 659 and 662 at 200 ppm inhibit fungal infestations in both tests D-1a) and D-1b) by 80-100%. At the same time untreated plants showed pathogen attack of 60-100%.

D-2: Action Against *Phytophthora* on Tomato Plants a) Residual-protective Action After a cultivation period of 3 weeks, tomato plants are sprayed with a spray mixture (0.02% active ingredient) prepared from a wettable powder formulation of the test compound. After 48 hours, the treated plants are infected with a sporangia suspension of the fungus. Fungus infestation is evaluated after incubation of the infected plants for 5 days at 90-100% relative humidity and +20° C.

b) Systemic Action

After a cultivation period of 3 weeks, tomato plants are watered with a spray mixture (0.02% active ingredient based on the volume of the soil) prepared from a wettable powder formulation of the test compound. Care is taken that the spray mixture does not come into contact with the parts of the plants that are above the ground. After 96 hours, the treated plants are infected with a sporangia suspension of the fungus. Fungus infestation is evaluated after incubation of the infected plants for 4 days at 90-100% relative humidity and +20° C. Compounds of Tables 1 exhibit a good fungicidal action against *Plasmopara viticola* on vines. Compounds No. 040, 052, 059, 071, 091, 101, 102, 104, 105, 157, 186, 197, 220, 228, 229, 271, 288, 289, 331, 332, 378, 381, 391, 421, 422, 452, 453, 469, 479, 489, 499, 512, 513, 514, 517, 464, 568, 607, 659 and 662 at 200 ppm inhibit fungal infestations in both tests D-1a) and D-1b) by 80-100%. At the same time untreated plants showed pathogen attack of 60-100%.

D-3: Action Against *Phytophthora* on Potato Plants a) Residual-protective Action 2-3 week old potato plants (Bintje variety) are sprayed with a spray mixture (0.02% active ingredient) prepared from a wettable powder formulation of the test compound. After 48 hours, the treated plants are infected with a sporangia suspension of the fungus. Fungus infestation is evaluated after incubation of the infected plants for 4 days at 90-100% relative humidity and +20° C.

b) Systemic Action 2-3 week old potato plants (Bintje variety) are watered with a spray mixture (0.02% active ingredient based on the volume of the soil) prepared from a wettable powder formulation of the test compound. Care is taken that the spray mixture does not come into contact with the parts of the plants that are above the ground. After 48 hours, the treated plants are infected with a sporangia suspension of the fungus. Fungus infestation is evaluated after incubation of the infected plants for 4 days at 90-100% relative humidity and +20° C. Fungal infestation is effectively controlled with compounds of Table 1.

Compounds 040, 052, 105, 157, 228, 229, 271, 288, 289, 332, 421, 422, 469, 479, 489, 514, 517, 564, 568, 607, 659 and 662 at 200 ppm inhibit fungal infestations in both tests D-3a) and D-3b) by 60-100%. At the same time untreated plants showed a pathogen attack of 60-100%.

The invention claimed is:
1. A compound of the general formula

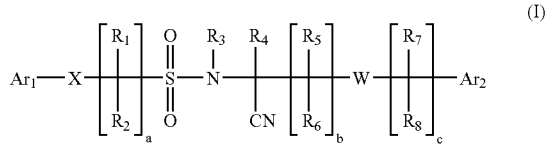

(I)

including the optical isomers thereof and mixtures of such isomers, wherein
$Ar_1$ and $Ar_2$ independently of each other stand for an optionally substituted phenyl group,
$R_1$ and $R_2$ stand independently of each other for hydrogen, optionally substituted $C_1$-$C_5$alkyl, optionally substituted $C_2$-$C_5$alkenyl, $C_2$-$C_5$alkynyl or optionally substituted $C_3$-$C_6$cycloalkyl;
$R_3$ designates hydrogen, $C_3$-$C_5$alkenyl, $C_3$-$C_5$alkynyl or optionally substituted $C_1$-$C_5$alkyl;
$R_4$ is optionally substituted $C_1$-$C_5$alkyl, optionally substituted $C_2$-$C_5$alkenyl, $C_2$-$C_5$alkynyl or optionally substituted $C_3$-$C_6$cycloalkyl;
$R_5$ and $R_6$ are independently of each other hydrogen or optionally substituted $C_1$-$C_5$alkyl, optionally substituted $C_2$-$C_5$alkenyl, $C_2$-$C_5$alkynyl or optionally substituted $C_3$-$C_6$cycloalkyl;
$R_7$ and $R_8$ are independently of each other hydrogen or optionally substituted $C_1$-$C_5$alkyl, optionally substituted $C_2$-$C_5$alkenyl, $C_2$-$C_5$alkynyl or optionally substituted $C_3$-$C_6$cycloalkyl;
W designates a bridge selected from —O—, —S(O)$_m$— or —NR$_3$—;
X designates a direct bond or a bridge selected from —O—, —S(O)$_m$— or —NR$_3$—;
a and b independently of each other stand for a number 1, 2 or 3; and
c and m independently of each other stand for a number zero, 1 or 2.

2. A compound according to claim 1 wherein $Ar_1$ stands for a phenyl group which is optionally substituted with n radicals independently selected from $R_9$; $Ar_2$ stands for a phenyl group which is optionally substituted with n radicals independently selected from $R'_9$ and from one radical $R_{10}$;
$R_1$ and $R_2$ stand independently of each other for hydrogen or $C_1$-$C_5$alkyl optionally substituted by halogen, $C_1$-$C_3$alkoxy or —NR$_{12}$R$_{13}$; or stand for $C_2$-$C_5$alkenyl optionally substituted by halogen or $C_1$-$C_3$alkoxy; or stand for $C_2$-$C_5$alkynyl; or stand for $C_3$-$C_6$cycloalkyl optionally substituted by halogen, $C_1$-$C_3$alkoxy; $C_1$-$C_3$alkyl or —NR$_{12}$R$_{13}$;
$R_3$ designates hydrogen, $C_3$-$C_5$alkenyl, $C_3$-$C_5$alkynyl or $C_1$-$C_3$alkyl optionally substituted by $C_1$-$C_3$alkoxy; $C_3$-$C_5$alkenyloxy or $C_3$-$C_5$alkynyloxy;
$R_4$ is $C_1$-$C_5$-alkyl optionally substituted by halogen, $C_1$-$C_3$alkoxy or —NR$_{12}$R$_{13}$; or is $C_2$-$C_5$alkenyl optionally substituted by halogen or $C_1$-$C_3$alkoxy; or is $C_2$-$C_5$alkynyl; or is $C_3$-$C_6$cycloalkyl optionally substituted by halogen, $C_1$-$C_3$alkoxy or $C_1$-$C_3$alkyl;
$R_5$ and $R_6$ are independently of each other hydrogen or $C_1$-$C_5$alkyl optionally substituted by halogen, $C_1$-$C_3$alkoxy or —NR$_{12}$R$_{13}$; or are $C_2$-$C_5$alkenyl optionally substituted by halogen or $C_1$-$C_3$alkoxy; or are $C_2$-$C_5$alkynyl; or are $C_3$-$C_6$cycloalkyl optionally substituted by halogen, $C_1$-$C_3$alkoxy; $C_1$-$C_3$alkyl or —NR$_{12}$R$_{13}$;
$R_7$ and $R_8$ are independently of each other hydrogen or $C_1$-$C_5$alkyl optionally substituted by halogen, $C_1$-$C_3$alkoxy or —NR$_{12}$R$_{13}$; or are $C_2$-$C_5$alkenyl optionally substituted by halogen or $C_1$-$C_3$alkoxy; or are $C_2$-$C_5$alkynyl; or are $C_3$-$C_6$cycloalkyl optionally substituted by halogen, $C_1$-$C_3$alkoxy; $C_1$-$C_3$alkyl or —NR$_{12}$R$_{13}$;
$R_9$ and $R'_9$ independently of each other stand for $C_1$-$C_5$alkyl optionally substituted by halogen, $C_1$-$C_4$alkoxy, —NR$_{12}$R$_{13}$, —CO—R$_{14}$ or the acyclic or cyclic ketals and acetals of —CO—R$_{14}$, by a —X-aryl which is optionally substituted by halogen, $C_1$-$C_4$alkyl, $C_1$-$C_4$haloalkyl, $C_1$-$C_4$alkoxy, —CN, —NO$_2$, —NR$_{12}$R$_{13}$, —CO—R$_{14}$ or the acyclic or cyclic ketals and acetals of —CO—R$_{14}$; by a —X-linked-5- or 6-ring-membered heteroaryl group optionally substituted by halogen, $C_1$-$C_4$alkyl, $C_1$-$C_4$haloalkyl, $C_1$-$C_4$alkoxy, —CN, —NO$_2$, —NR$_{12}$R—, —CO—R$_{14}$ or the acyclic or cyclic ketals and acetals of —CO—R$_{13}$; or stand for $C_3$-$C_6$cycloalkyl, optionally substituted by halogen, hydroxy, =O, $C_1$-$C_4$alkoxy, NR$_{12}$R$_{13}$; or stand for $C_1$-$C_4$alkoxy optionally substituted by halogen, $C_1$-$C_4$alkoxy, by —X-aryl which is optionally substituted by halogen, $C_1$-$C_4$alkyl, $C_1$-$C_4$haloalkyl, $C_1$-$C_4$alkoxy, —CN, —NO$_2$, —NR$_{12}$R$_{13}$, —CO—R$_{14}$ or the acyclic or cyclic ketals and acetals of —CO—R$_{14}$; by a X-linked-5- or 6-ring-membered heteroaryl group optionally substituted by halogen, $C_1$-$C_4$alkyl, $C_1$-$C_4$haloalkyl, $C_1$-$C_4$alkoxy, —CN, —NO$_2$, —NR$_{12}$R$_{13}$, —CO—R$_{14}$ or the acyclic or cyclic ketals and acetals of —CO—R$_{14}$; or stand for $C_2$-$C_5$alkenyl optionally substituted by halogen or aryl; or stand for $C_2$-$C_5$alkynyl optionally substituted by halogen, trialkyl-silyl or aryl; or stand for $C_2$-$C_5$alkenyloxy optionally substituted by halogen or aryl; or stand for $C_2$-$C_5$alkynyloxy optionally substituted by halogen, tri-alkyl-silyl or aryl; or stand for $C_3$-$C_6$cycloalkoxy optionally substituted by $C_1$-$C_3$alkyl, halogen or $C_1$-$C_4$alkoxy; or stand for halogen; or stand for —NR$_{12}$R$_{13}$, or stand for —NR$_2$—CO—R$_{12}$; or stand for —NR$_2$—CO—OR$_{12}$; or stand for —NR$_2$—CO—NR$_8$R$_9$; or stand for —NR$_2$—CO—SR$_{12}$; or stand for N R$_2$—CS—OR$_{12}$; or stand for —NR$_2$—CS—NR$_8$R$_9$; or stand for —NR$_2$—CS—SR$_{12}$; or stand for NR$_2$—C(=N—O—R$_{12}$)—S—OR$_{12}$; or stand for —NR$_2$—C(=N—O—R$_{12}$)—NR$_8$R$_9$; or stand for —NR$_2$—C(=N—O—R$_{12}$)—SR$_{12}$; or stand for —S(O)$_p$—C$_1$-C$_4$alkyl optionally substituted by halogen; or stand for —NR$_2$—SO$_2$—NR$_8$R$_9$; or stand for nitro, for cyano or for —CS—NH$_2$;
$R_{10}$ stands for hydrogen; or stands for —X-aryl which is optionally substituted by halogen, $C_1$-$C_4$alkyl, $C_1$-$C_4$haloalkyl, $C_1$-$C_4$alkoxy, —CN, —NO$_2$, —NR$_{12}$R$_{13}$, —CO—R$_{14}$ or the acyclic or cyclic ketals and acetals of —CO—R$_{14}$; or stands for a X-linked 5-membered aromatic or non-aromatic heterocyclic ring comprising nitrogen, oxygen or sulfur as ring members and being optionally substituted by halogen, $C_1$-$C_4$alkyl, $C_1$-$C_4$haloalkyl, $C_1$-$C_4$alkoxy, —CN, —NO$_2$, —NR$_{12}$R$_{13}$, —CO—R$_{14}$ or the acyclic or cyclic ketals and acetals of —CO—R$_{14}$; or stands for a X-linked 6-membered aromatic or non-aromatic heterocyclic ring comprising nitrogen, oxygen or sulfur as ring members and being optionally substituted by halogen, $C_1$-$C_4$alkyl, $C_1$-$C_4$haloalkyl, $C_1$-$C_4$alkoxy, —CN, —NO$_2$, —NR$_{12}$R$_{13}$, —CO—R$_{14}$ or the acyclic or cyclic ketals and acetals of —CO—R$_{14}$; or stands for —CO—R$_{14}$ or the acyclic or cyclic ketals and acetals of —CO—R$_{14}$; or stands for —O—CO—R$_{14}$; or stands for —C(=N—O—R$_{12}$)—R$_{14}$;

R$_{10}$ and one R'$_9$ together form a 3- or 4-membered non-aromatic bridge forming an annellated ring which may contain a carbonyl function or nitrogen, oxygen or sulfur as ring members and is optionally substituted by $C_1$-$C_3$alkyl;

W designates a bridge selected from —O—, —S(O)$_m$— or —NR$_3$—;

X designates a direct bond or a bridge selected from —O—, —S(O)$_m$— or —NR$_3$—;

a stands for a number 1, 2 or 3;
b stands for a number 1, 2 or 3;
c stands for a number zero, 1 or 2;
m stands for a number zero, 1 or 2;
n stands for a number 1 or 2;
p stands for a number 0, 1 or 2;

R$_{12}$ and R$_{13}$ independently of each other stand for hydrogen; $C_1$-$C_5$alkyl optionally substituted by halogen, $C_1$-$C_4$haloalkyl, $C_1$-$C_4$alkoxy, $C_1$-$C_4$alkylamino, di($C_1$-$C_4$alkyl)amino, or aryl which in turn is optionally substituted by halogen, $C_1$-$C_4$alkyl, $C_1$-$C_4$haloalkyl, $C_1$-$C_4$alkoxy or —CN; or stand for $C_3$-$C_5$alkenyl optionally substituted by halogen, $C_1$-$C_4$haloalkyl, $C_1$-$C_4$alkoxy, $C_1$-$C_4$alkylamino, di($C_1$-$C_4$alkyl)amino, or aryl which in turn is optionally substituted by halogen, $C_1$-$C_4$alkyl, $C_1$-$C_4$haloalkyl, $C_1$-$C_4$alkoxy or —CN; or stand for $C_3$-$C_5$alkynyl optionally substituted by halogen, $C_1$-$C_4$haloalkyl, $C_1$-$C_4$alkoxy, $C_1$-$C_4$alkylamino, di($C_1$-$C_4$alkyl)amino, or aryl which in turn is optionally substituted by halogen, $C_1$-$C_4$alkyl, $C_1$-$C_4$haloalkyl, $C_1$-$C_4$alkoxy or —CN; or together form a 5-ring-membered non-aromatic carbocyclic ring; or together form a 6-ring-membered non-aromatic carbocyclic ring which is interrupted by —O— or —N($C_1$-$C_4$alkyl)—;

R$_{14}$ stands for $C_1$-$C_5$alkyl optionally substituted by halogen, $C_1$-$C_4$alkoxy, $C_1$-$C_4$alkylamino, di($C_1$-$C_4$alkyl)amino; aryl which in turn is optionally substituted by halogen, $C_1$-$C_4$alkyl, $C_1$-$C_4$haloalkyl, $C_1$-$C_4$alkoxy, —CN, —NO$_2$, $C_1$-$C_4$alkylamino, di($C_1$-$C_4$alkyl)amino or $C_1$-$C_4$alkylcarbonyl, $C_1$-$C_4$alkoxycarbonyl, $C_1$-$C_4$alkylaminocarbonyl or di($C_1$-$C_4$alkyl)aminocarbonyl; or by a 5- or 6-ring hetero-aromatic ring which in turn is optionally substituted by halogen, $C_1$-$C_4$alkyl, $C_1$-$C_4$haloalkyl $C_1$-$C_4$alkoxy, —CN, —NO$_2$, $C_1$-$C_4$alkylamino, di($C_1$-$C_4$alkyl)amino, $C_1$-$C_4$alkylcarbonyl, $C_1$-$C_4$alkoxycarbonyl, $C_1$-$C_4$alkylaminocarbonyl or di-($C_1$-$C_4$alkyl)aminocarbonyl; or stands for $C_3$-$C_6$cycloalkyl optionally substituted by halogen, hydroxy, =O, $C_1$-$C_4$alkoxy or $C_1$-$C_4$alkylamino, di($C_1$-$C_4$alkyl)amino; or stands for $C_1$-$C_4$alkoxy optionally substituted by halogen, $C_1$-$C_4$alkoxy; $C_1$-$C_4$alkylamino, di($C_1$-$C_4$alkyl)amino; or stands for phenyl which is optionally substituted by halogen, $C_1$-$C_4$alkyl, $C_1$-$C_4$haloalkyl, $C_1$-$C_4$alkoxy, —CN, —NO$_2$, $C_1$-$C_4$alkylamino, di($C_1$-$C_4$alkyl)amino, $C_1$-$C_4$al-kylcarbonyl, $C_1$-$C_4$alkoxycarbonyl, $C_1$-$C_4$alkylaminocarbonyl or di-($C_1$-$C_4$alkyl)aminocarbonyl; or stands for a 5- or 6-ring membered heteroaryl comprising nitrogen, oxygen or sulfur as ring members and being optionally substituted by halogen, $C_1$-$C_4$alkyl, $C_1$-$C_4$haloalkyl; $C_1$-$C_4$alkoxy, —CN, —NO$_2$, $C_1$-$C_4$alkylamino, di($C_1$-$C_4$alkyl)amino, $C_1$-$C_4$alkylcarbonyl, $C_1$-$C_4$alkoxycarbonyl, $C_1$-$C_4$alkylaminocarbonyl or di-($C_1$-$C_4$alkyl)aminocarbonyl.

3. A compound according to claim 1, wherein Ar$_1$ and Ar$_2$ independently of each other stand for optionally substituted phenyl; and the optional substituents R$_9$ of Ar$_1$ are preferably selected from the group comprising halogen, $C_1$-$C_4$alkyl, $C_1$-$C_4$haloalkyl, $C_1$-$C_4$alkoxy, $C_1$-$C_4$haloalkoxy, $C_3$-$C_6$cycloalkyl, —CN and —CO—R$_{14}$; and the optional substituents R'$_9$ of Ar$_2$ are preferably selected from the group comprising halogen, $C_1$-$C_4$alkyl, $C_1$-$C_4$haloalkyl, $C_1$-$C_4$alkoxy, $C_1$-$C_4$haloalkoxy, $C_3$-$C_6$cycloalkyl, —CN, —CO—R$_{14}$, —NR$_{12}$R$_{13}$, —NR$_2$—CO—R$_{12}$, —NR$_3$—CO—OR$_{12}$, —NR$_2$—CO—NR$_8$R$_9$, —NR$_2$—CO—SR$_{12}$, —NR$_2$—CS—OR$_{12}$, —NR$_2$—CS—NR$_8$R$_9$, —NR$_2$—CS—SR$_{12}$, —S(O)$_p$—$C_1$-$C_4$alkyl, —S(O)$_p$—$C_1$-$C_4$haloalkyl, —NR$_2$—SO$_2$—NR$_8$R$_9$, nitro, cyano and —CS—NH$_2$; and the optional substituent R$_{10}$ on Ar$_2$ is selected from optionally substituted phenyl, optionally substituted imidazolyl, optionally substituted thiazolyloxy, optionally substituted pyridyloxy, optionally substituted pyridyl, optionally substituted pyrimidinyloxy, optionally substituted pyrimidinyl, optionally substituted oxadiazolyl, optionally substituted triazolyl, optionally substituted pyrazolyl, optionally substituted oxadiazolyloxy, optionally substituted triazolyloxy and optionally substituted pyrazolyloxy.

4. A compound of formula I according to claim 1 wherein Ar$_1$ and Ar$_2$ independently stand for optionally substituted phenyl groups; and the optional substituents R$_9$ of Ar$_1$ are preferably selected from the group comprising halogen, $C_1$-$C_4$alkyl, $C_1$-$C_4$haloalkyl, $C_1$-$C_4$alkoxy, $C_1$-$C_4$haloalkoxy, $C_3$-$C_6$cycloalkyl, —CN and —CO—R$_{14}$; and the optional substituents R'$_9$ of Ar$_2$ are preferably selected from the group comprising halogen, $C_1$-$C_4$alkyl, $C_1$-$C_4$haloalkyl, $C_1$-$C_4$alkoxy, $C_1$-$C_4$haloalkoxy, $C_3$-$C_6$cycloalkyl, —CN, —CO—R$_{14}$, —NR$_{12}$R$_{13}$, —NR$_2$—CO—R$_{12}$, —NR$_3$—CO—OR$_{12}$, —NR$_2$—CO—NR$_8$R$_9$, —NR$_2$—CO—SR$_{12}$, —NR$_2$—CS—OR$_{12}$, —NR$_2$—CS—NR$_8$R$_9$, —NR$_2$—CS—SR$_{12}$, —S(O)$_p$—$C_1$-$C_4$alkyl, —S(O)$_p$—$C_1$-$C_4$haloalkyl, —NR$_2$—SO$_2$—NR$_8$R$_9$, nitro, cyano and —CS—NH$_2$; and the optional substituent R$_{10}$ on Ar$_2$ is selected from halogen, $C_1$-$C_4$alkyl, $C_1$-$C_4$haloalkyl, $C_1$-$C_4$alkoxy, —CN, —NO$_2$, —NR$_{12}$R$_{13}$, —CO—R$_{14}$ and the acyclic or cyclic ketals and acetals of —CO—R$_{14}$; —O—CO—R$_{14}$, optionally substituted phenyl, optionally substituted imidazolyl, optionally substituted thiazolyloxy, optionally substituted pyridyloxy, optionally substituted pyridyl, optionally substituted pyrimidinyloxy, optionally substituted pyrimidinyl, optionally substituted oxadiazolyl, optionally substituted triazolyl, optionally substituted pyrazolyl, optionally substituted oxadiazolyloxy, optionally substituted triazolyloxy and optionally substituted pyrazolyloxy; and R$_1$, R$_2$, R$_5$, R$_6$, R$_7$ and R$_8$ independently of each other are hydrogen or methyl; and R$_3$ is hydrogen or $C_1$-$C_4$alkyl optionally substituted with $C_1$-$C_4$alkoxy, $C_3$-$C_4$alkenyloxy, or $C_3$-$C_4$alkynyloxy; and R$_4$ is hydrogen or $C_1$-$C_4$alkyl optionally substituted with halogen, $C_1$-$C_3$alkoxy, $C_1$-$C_3$alkylamino or di-$C_1$-$C_3$alkylamino; and

97

W is —O—; and

X is a direct bond; and the suffixes (a) and (b) designate the number 1; and the suffix (c) stands for the number zero.

5. A compound of formula I according to claim 1 wherein $Ar_1$ and $Ar_2$ independently of each other stand for optionally substituted phenyl; and the optional substituents $R_9$ and $R'_9$ of $Ar_1$ and $Ar_2$ are selected from the group comprising $C_1$-$C_4$alkyl, $C_1$-$C_4$haloalkyl, $C_1$-$C_4$alkoxy, $C_1$-$C_4$haloalkoxy and $C_3$-$C_6$cycloalkyl; and the optional substituent $R_{10}$ on $Ar_2$ is selected from —CO—$C_1$-$C_4$alkyl, —CO—$C_1$-$C_4$alkoxy, —O—CO—$C_1$-$C_4$alkyl, optionally substituted phenyl, optionally substituted phenoxy, optionally substituted imidazolyl, optionally substituted imidazolyloxy, optionally substituted thiazolyloxy, optionally substituted thiazolyl, optionally substituted thiadiazolyloxy, optionally substituted thiadiazolyl, optionally substituted pyridyloxy, optionally substituted pyridyl, optionally substituted pyrimidinyloxy, optionally substituted pyrimidinyl, optionally substituted oxadiazolyl, optionally substituted oxadiazolyloxy, optionally substituted triazolyl, optionally substituted pyrazolyl, optionally substituted triazolyloxy and optionally substituted pyrazolyloxy; and $R_1$ and $R_5$ are independently $C_1$-$C_4$alkyl and $R_2$ and $R_6$ are hydrogen; and $R_3$ is hydrogen, $C_1$-$C_4$alkyl or $C_1$-$C_4$alkoxy-$C_1$-$C_4$alkyl; and $R_4$ is $C_1$-$C_4$alkyl or $C_1$-$C_4$haloalkyl; and W is —O—; and X is a direct bond; and the suffixes (a) and (b) designate the number 1; and the suffix (c) stands for the number zero.

6. A compound of formula I according to claim 1, wherein $Ar_1$ and $Ar_2$ independently of each other stand for optionally substituted phenyl; and the optional substituents $R_9$ and $R'_9$ of $Ar_1$ and $Ar_2$ are selected from the group comprising bromo, chloro, fluoro, iodo, cyano, hydroxy, amino, nitro, methyl, ethyl, propyl, isopropyl, methoxy, ethoxy, propoxy, isopropoxy, allyloxy, propargyloxy, benzyloxy, trifluoromethyl, trifluoromethoxy, 2-cyano-2-methyl-butyloxy, methylsulfonyl, methylsulfinyl, methyithia, cyclopentyl, cyclohexyl, aminocarbonylmethyl, methoximinoethyl, aminocarbonyl, butylcarbonylamino, tert-butylcarbonylamino, triazol-1-ylmethyl, 1,2,4-triazol-1-ylmethyl, N-morpholinocarbonylamino, aminocarbonyloxy-ethoxy, morpholinocarbonyloxyethoxy and cyanopyridyloxyethoxy; and the optional substituent $R_{10}$ on $Ar_2$ is selected from aminocarbonyl, dimethylaminocarbonyl, acetyl, propionyl, acetoxy, methoxycarbonyl, ethoxycarbonyl, benzoyl, methoxi minoethyl, 1-imidazolyl, 5-(3-methyl-1,2,4-thiadiazolyloxy), 2-pyridyl, 2-pyridyloxy, 4-pyrimidinyl, 2-(3,5-dichloropyridyloxy), 2-(4,6-dichloropyridyloxy), 2-(4,6-dimethoxypyrimidinylthio), 2-oxadiazolyl, 2-(5-methyl-oxadazolyl), 2-(5-ethyl-oxadiazolyl), 1-triazolyl, 1-pyrazolyl, 1-(3,4-dimethylpyrazolyl), 4-(2-methylthiazolyl), 2-(1,3,4-oxydiazolyl), N-pyrrolidin-2-onyl, and 2-quinoxalinyl, and $R_1$ and $R_5$ are independently $C_1$-$C_4$alkyl and $R_2$ and $R_6$ are hydrogen; and $R_3$ is hydrogen, $C_1$-$C_4$alkyl or $C_1$-$C_4$alkoxy-$C_1$-$C_4$alkyl; and

98

$R_4$ is $C_1$-$C_4$alkyl or $C_1$-$C_4$haloalkyl; and

W is —O—; and

X is a direct bond; and the suffixes (a) and (b) designate the number 1; and the suffix (c) stands for the number zero.

7. A compound according to claim 1, wherein $Ar_1$ and $Ar_2$ independently of each other stand for optionally substituted phenyl; and the optional substituents $R_9$ and $R'_9$ of $Ar_1$ and $Ar_2$ are selected from the group comprising bromo, chloro, fluoro, methyl, ethyl, methoxy, ethoxy, trifluoromethyl and trifluoromethoxy; and the optional substituent $R_{10}$ on $Ar_2$ is selected from aminocarbonyl, acetyl, methoxycarbonyl, ethoxycarbonyl, 1-imidazolyl, 5-(3-methyl-1,2,4-thiadiazolyloxy), 2-pyridyl, 2-pyridyloxy, 4-pyrimidinyl, 2-(3,5-dichloropyridyloxy), 2-(4,6-dimethoxypyrimidinylthio), 2-oxadiazolyl, 2-(5-methyloxadazolyl), 2-(5-ethyl-oxadiazolyl), 1-triazolyl, 1-pyrazolyl, 4-(2-methylthiazolyl), 2-(1,3,4-oxydiazolyl), and N-pyrrolidin-2-onyl, and $R_1$ and $R_5$ are methyl and $R_2$ and $R_6$ are hydrogen; and $R_3$ is hydrogen, methyl, ethyl, propyl, ethoxymethyl or methoxymethyl, and $R_4$ is methyl, ethyl, propyl or fluoromethyl; and W is —O—; and X is a direct bond; and the suffixes (a) and (b) designate the number 1; and the suffix (c) stands for the number zero.

8. A compound of formula I according to claim 1 selected from the group consisting of 2-[(4-chlorophenoxy)-methyl]-2-benzylsulfonylamino-propionitrile, 2-[(4-chlorophenoxy)-methyl]-2-[(2-chlorophenyl)-methyl]-sulfonylamino-propionitrile, 2-[(4-chlorophenoxy)-methyl]-2-[(2-fluorophenyl)-methyl]-sulfonylamino-propionitrile, 2-[(4-trifluoromethoxyphenoxy)-methyl]-2-benzylsulfonylamino-propionitrile, 2-[(4-chloro-3-methylphenoxy)-methyl]-2-benzylsulfonylamino-propionitrile, 2-[(4-chlorophenoxy)-methyl]-2-benzylsulfonylamino-propionitrile, 2-[(4-chlorophenoxy)-methyl]-2-benzylsulfonylamino-propiontrile, 2-[(4-acetylphenoxy)-methyl]-2-benzylsulfonylamino-propionitrile, 2-[(4-methoxyphenoxy)-methyl]-2-benzylsulfonylamino-propionitrile, 2-[(4-acetylphenoxy)-methyl]-2-benzylsulfonylamino-butyronitrile, 2-[(4-cyanophenoxy)-methyl]-2-benzylsulfonylamino-propionitrile, (−)-2-[(4-cyanophenoxy)-methyl]-2-benzylsulfonylamino-propionitrile, 2-[(4-propionylphenoxy)-methyl]-2-benzylsulfonylamino-propionitrile, 2-[(4-ethoxyphenoxy)-methyl]-2-benzylsulfonylamino-propionitrile, 2-[(4-[1,2,4]triazol-1-yl-phenoxy)-methyl]-2-benzylsulfonylamino-propionitrile, 2-[(4-imidazol-1-yl-phenoxy)-methyl]-2-benzylsulfonylamino-propionitrile, 2-[(4-cyanophenoxy)-methyl]-2-benzylsulfonylamino-butyronitrile, 2-[(4-[1,3,4]oxadiazol-4-yl-phenoxy)-methyl]-2-benzylsulfonylamino-propionitrile, 2-[(4-methoxyphenoxy)-methyl]-2-benzylsulfonylamino-butyronitrile,
2-[(4-ethoxyphenoxy)-methyl]-2-benzylsulfonylamino-butyronitrile,
(−)2-[(4-ethoxyphenoxy)-methyl]-2-benzylsulfonylamino-butyronitrile,
2-[(4-[1,2,4]triazol-1-yl-phenoxy)-methyl]-2-benzylsulfonylamino-butyronitrile,
2-[(4-methoxycarbonylphenoxy)-methyl]-2-benzylsulfonylamino-propionitrile,
2-[(4-propionylphenoxy)-methyl]-2-benzylsulfonylamino-butyronitrile,
2-[(4-chlorophenoxy)-methyl]-2-benzylsulfonylamino-3-fluoro-propionitrile,
2-{[4-(2-methyl-thiazol-4-yl)-phenoxy]-methyl}-2-benzylsulfonylamino-butyronitrile,
2-[(4-pyrazol-1-yl-phenoxy)-methyl]-2-benzylsulfonylamino-butyronitrile,
2-[(4-chloro-phenoxy)-methyl]-2-benzylsulfonylamino-3-methyl-butyronitrile,
2-[(4-iso-propyl-phenoxy)-methyl]-2-benzylsulfonylamino-butyronitrile,
2-[(4-nitro-phenoxy)-methyl]-2-benzylsulfonylamino-butyronitrile,
2-[(4-cyano-phenoxy)-methyl]-2-benzylsulfonylamino-butyronitrile,
2-[(3-fluoro-4-propionyl-phenoxy)-methyl]-2-benzylsulfonylamino-propionitrile,
(−)-2-[(4-[1,2,4]triazol-1-yl-phenoxy)-methyl]-2-benzylsulfonylamino-butyronitrile, and
(−)-2-[(4-acetylphenoxy)-methyl]-2-benzylsulfonylamino-propionitrile.

9. A process for the preparation of a compound of formula I

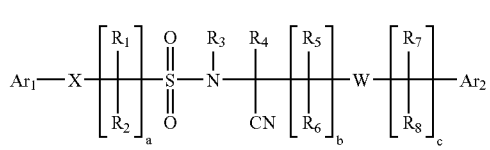

including the optical isomers thereof and mixtures of such isomers, wherein
$Ar_1$ and $Ar_2$ independently of each other stand for an optionally substituted phenyl group,
$R_1$ and $R_2$ stand independently of each other for hydrogen, optionally substituted $C_1$-$C_5$alkyl, optionally substituted $C_2$-$C_5$alkenyl, $C_2$-$C_5$alkynyl or optionally substituted $C_3$-$C_6$cycloalkyl;
$R_3$ designates hydrogen, $C_3$-$C_5$alkenyl, $C_3$-$C_5$alkynyl or optionally substituted $C_1$-$C_5$alkyl;
$R_4$ is optionally substituted $C_1$-$C_5$alkyl, optionally substituted $C_2$-$C_5$alkenyl, $C_2$-$C_5$alkynyl or optionally substituted $C_3$-$C_6$cycloalkyl;
$R_5$ and $R_6$ are independently of each other hydrogen or optionally substituted $C_1$-$C_5$alkyl, optionally substituted $C_2$-$C_5$alkenyl, $C_2$-$C_5$alkynyl or optionally substituted $C_3$-$C_6$cycloalkyl;
$R_7$ and $R_8$ are independently of each other hydrogen or optionally substituted $C_1$-$C_5$alkyl, optionally substituted $C_1$-5alkenyl, $C_2$-$C_5$alkynyl or optionally substituted $C_3$-$C_6$cycloalkyl;

W designates a bridge selected from —O—, —S(O)$_m$— or —NR$_3$—;
X designates a direct bond or a bridge selected from —O—, —S(O)$_m$— or —NR$_3$—;
a and b independently of each other stand for a number 1, 2 or 3; and
c and m independently of each other stand for a number zero, 1 or 2;
which comprises reacting
a) reacting the sulfonylating agent of formula II

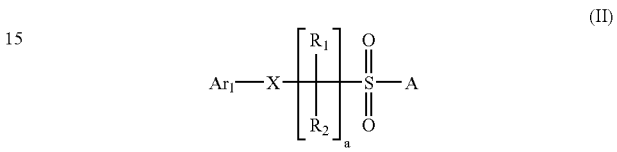

wherein A stands for a leaving group with an aminoacetonitrile of formula III

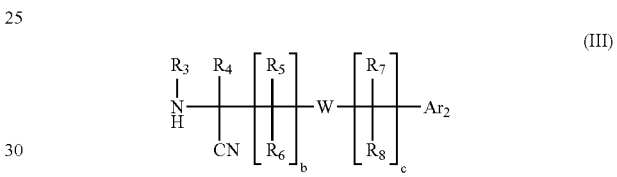

or b) coupling the reacting the compound of formula XIII

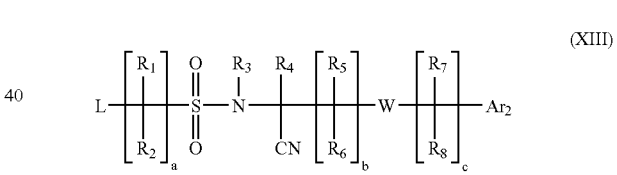

wherein L is a leaving group or a sulfonyloxy group is coupled with a compound of formula XIV $$Ar_1—X'$$ (XIV)

wherein X' is either an anionic radical species of X combined with an alkaline- or earthalkaline- metal cation as counterion or is defined as X—H if at the same time the reaction is generally carried out in the presence of a base or an agent capable of scavenging the formed acid.

10. A composition comprising a compound of formula I according to claim 1 as active ingredient together with a suitable carrier.

11. A method of controlling and preventing an infestation of crop plants by phytopathogenic fungi, which comprises the application of a compound of formula I according to claim 1 as active ingredient to the plant, to parts of plants or to the locus thereof.

* * * * *